(12) United States Patent
Mulder

(10) Patent No.: US 10,702,598 B2
(45) Date of Patent: Jul. 7, 2020

(54) FORMULATION OF A PEPTIDE VACCINE

(71) Applicant: ISA PHARMACEUTICALS B.V., Leiden (NL)

(72) Inventor: Gwenn Eveline Mulder, Utrecht (NL)

(73) Assignee: ISA PHARMACEUTICALS B.V., Leiden (NL)

( * ) Notice: Subject to any disclaimer, the term of this patent is extended or adjusted under 35 U.S.C. 154(b) by 0 days.

(21) Appl. No.: 16/311,629

(22) PCT Filed: Jun. 19, 2017

(86) PCT No.: PCT/EP2017/064882
§ 371 (c)(1),
(2) Date: Dec. 19, 2018

(87) PCT Pub. No.: WO2017/220463
PCT Pub. Date: Dec. 28, 2017

(65) Prior Publication Data
US 2019/0231863 A1 Aug. 1, 2019

(30) Foreign Application Priority Data

Jun. 20, 2016 (EP) .................................... 16175215

(51) Int. Cl.
| | | |
|---|---|---|
| *A61K 47/00* | (2006.01) | |
| *A61K 38/00* | (2006.01) | |
| *A61K 38/02* | (2006.01) | |
| *A61K 39/12* | (2006.01) | |
| *A61K 39/00* | (2006.01) | |
| *A61K 47/10* | (2017.01) | |
| *A61P 35/00* | (2006.01) | |
| *A61K 9/107* | (2006.01) | |
| *A61K 47/12* | (2006.01) | |
| *A61K 47/14* | (2017.01) | |
| *A61K 9/00* | (2006.01) | |

(52) U.S. Cl.
CPC .............. *A61K 39/12* (2013.01); *A61K 9/107* (2013.01); *A61K 39/0011* (2013.01); *A61K 47/10* (2013.01); *A61K 47/12* (2013.01); *A61K 47/14* (2013.01); *A61P 35/00* (2018.01); *A61K 9/0019* (2013.01); *A61K 9/1075* (2013.01); *A61K 2039/55566* (2013.01); *A61K 2039/585* (2013.01); *A61K 2039/70* (2013.01); *C12N 2710/20034* (2013.01)

(58) Field of Classification Search
None
See application file for complete search history.

(56) References Cited

U.S. PATENT DOCUMENTS

| | | | | |
|---|---|---|---|---|
| 7,202,034 B2* | 4/2007 | Van Der Burg | ....... | A61K 39/04 435/6.14 |
| 2007/0010424 A1* | 1/2007 | Pedersen | ................ | A61K 38/26 514/6.3 |
| 2009/0118354 A1* | 5/2009 | Liu | ...................... | A61K 9/0019 514/449 |

FOREIGN PATENT DOCUMENTS

WO   WO 2010/132867 A1   11/2010

OTHER PUBLICATIONS

Zhao et al. Stabilization of eptifibatide by cosolvents. International Journal of Pharmaceutics 218 (2001) 43-56.*
Anonymous, "A Guide to Handling and Storing Peptides", Peptides and Immunology, Mar. 8, 2006, pp. 1-3.
Anonymous, "Peptide Solubility Guidelines", ANASPEC, Dec. 28, 2011, pp. 1-2.
Bell et al., "Peptide Stability in Solids and Solutions", Biotechnology Progess, vol. 13, No. 4, 1997, pp. 342-346.
Nuijen et al., "Compatibility and stability of aplidine, a novel marine-deprived depsipeptide antitumor agent, in infusion devices, and its hemolytic and precipitation", Anti-Cancer Drugs, vol. 10, No. 10, Nov. 1, 1999, pp. 879-888.
Zhao et al., "Stabilization of eptifibatide by cosolvents", International Journal of Pharmaceutics, vol. 218, No. 1-2, May 1, 2001, pp. 43-56.
Strickley, "Solubilizing Excipients in Oral and Injectable Formulations", Pharmaceutical Research, vol. 21, No. 2, Feb. 1, 2004, pp. 201-230.
International Search Report issued in PCT/EP2017/064882, dated Oct. 9, 2017.
Written Opinion of the International Searching Authority issued in PCT/EP2017/064882, dated Oct. 9, 2017.
Melief et al., Therapeutic cancer vaccines, The Journal of Clinical Investigation, vol. 125, No. 9, Sep. 2015, 12 pages.

* cited by examiner

*Primary Examiner* — Nianxiang Zou
(74) *Attorney, Agent, or Firm* — Foley & Lardner LLP

(57) ABSTRACT

The invention relates to a novel reconstitution composition, a pharmaceutical composition and kit of parts comprising said reconstitution composition. The invention further relates to a method of treatment using said pharmaceutical composition and/or the pharmaceutical composition for use as a medicament. Also provided is a method for reconstituting dried peptides and a method for preparing a pharmaceutical composition using the reconstitution composition of the invention.

Figure 1A:
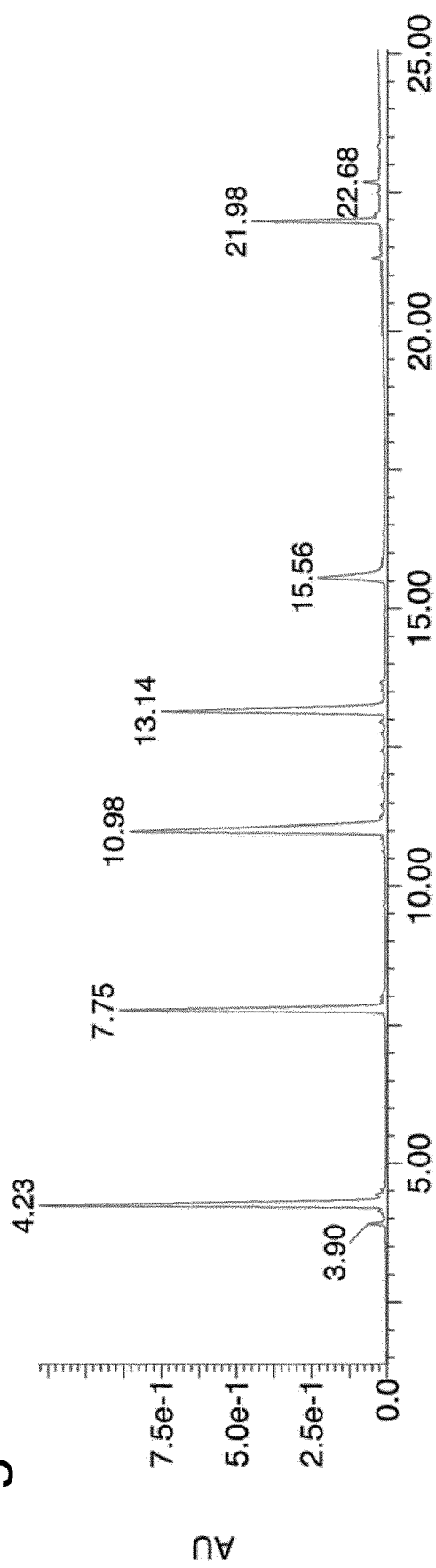

22 Claims, 17 Drawing Sheets
Specification includes a Sequence Listing.

FORMULATION OF A PEPTIDE VACCINE

CROSS-REFERENCE TO RELATED APPLICATIONS

This application is the National Phase of International Patent Application No. PCT/EP2017/064882, filed Jun. 19, 2017, published on Dec. 28, 2017 as WO 2017/220463 A1, which claims priority to European Application No. 16175215.9, filed Jun. 20, 2016. The contents of these applications are herein incorporated by reference in their entirety.

FIELD OF THE INVENTION

This invention is in the field of medicine and immunology. In particular, it relates to a novel composition for reconstituting peptides for vaccination. This composition is in particular suitable for preparing pharmaceutical peptide-based vaccines that further comprise an oil-based adjuvant.

BACKGROUND OF THE INVENTION

Clinical results have indicated that the era of successful therapeutic vaccination has arrived. Regression of lesions was shown for premalignant lesions caused by HPV and the clinical benefit of prolonged survival has been established. Vaccines based on synthetic long peptides are among the optimal vaccine platforms. Peptide vaccine or peptides-based vaccines are developed for the treatment of persistent infections and cancer, preferably targeting the immune system to clear cells that express viral antigens, cancer-antigens and/or neo-antigens. It is appreciated in the art that peptide-based vaccines capable of eliciting an effective cellular immune response ($CD4^+$ and $CD8^+$ T-cell response) targeting antigen-specific cytotoxic T cells capable of clearing the antigen-expressing cells. Antigens of choice include mutant sequences, selected cancer testis antigens and viral antigens (for review, see Melief et al. 2016 *Journal of Clinical Investigation*, Vol 125(9) pages 3401-3412).

One of the challenges of peptide-based vaccines is to provide for physically and chemically stable injectable solutions. This is in particular a challenge for peptide-based vaccine emulsions comprising more than one peptide and oil-based adjuvants. Injectable vaccine solutions are typically prepared on-site about 1 to 3 hours before administration to the patient using dried, mostly lyophilized peptides as a starting material. Therefore, there is a need for a suitable reconstitution composition that allows for the fast reconstitution of dried peptides, which can subsequently be admixed easily with oil-based adjuvants resulting in an emulsion that is physically and chemically stable for at least 2 to 3 hours storage at room temperature before being administered to the patient.

DETAILED DESCRIPTION OF THE INVENTION

Reconstitution Composition

Provided is a novel composition for reconstituting peptides for vaccination. This reconstitution composition comprises or consists of about 60-80% v/v aqueous solution comprising an organic acid, about 5-10% v/v propylene glycol (CAS no. 57-55-6), about 10-20% v/v lower alcohol and about 5-10% v/v non-ionic hydrophilic surfactant.

Preferably, the organic acid is a weak organic acid such as a carboxylic acid. A weak organic acid is to be understood herein as an organic acid having a $pK_a$ (logarithmic acid dissociation constant) of between −2 and 12. Preferably the weak organic acid has a $pK_a$ of between 1 and 10, or between 2 and 5 or even between 3 and 4. The weak organic acid may be, but is not limited to, any carboxylic acid selected from the group consisting of oxalic acid (ethanedioic acid), citric acid (2-hydroxypropane-1,2,3-tricarboxylic acid), malic acid (2-hydroxybutanedioic acid), carbonic acid (hydroxymethanoic acid), benzoic acid (benzenecarboxylic acid or phenylmethanoic acid), formic acid (methanoic acid), lactic acid (2-hydroxypropanoic acid), acetic acid (ethanoic acid), butyric acid (butanoic acid), valeric acid (pentanoic acid), caproic acid (hexanoic acid), and propionic acid (propanoic acid). Most preferably, the organic acid is citric acid.

The organic acid may be present in the aqueous solution at concentrations ranging from about 0.008 to 0.25M, or from about 0.01 to 0.2M, or from 0.05 to 0.1M. The reconstitution composition of the invention comprising 60-80%, or 65%-75% or 67%-72%, or about 70% of said aqueous solution preferably has a resulting concentration of said organic acid ranging from 0.05 to 0.2M, 0.006 to 0.16M, 0.008 to 0.12M, 0.03 to 0.08M, or preferably from 0.04 to 0.6M.

A lower alcohol is understood herein as an organic compound having a hydroxyl functional group bound to a saturated carbon atom of a lower alkyl or lower substituted alkyl group, wherein a lower alkyl or lower substituted alkyl group has at most 6 carbon atoms and preferably has the structure $CH_3$—$(CH_2)_n$—$OH$, wherein n=1, 2, 3, 4 or 5. Preferably, the lower alcohol is selected from the group consisting of methanol, ethanol, propanol, butanol and pentanol, most preferably the lower alcohol is ethanol.

The non-ionic hydrophilic surfactant preferably has a hydrophilic-lipophilic balance (HLB) value between 9 and 14, more preferably between 12 and 14. This surfactant may be, but is not limited to ethoxylated fatty acid mono- (in particular 5 ethoxyl groups), di- or tri- (in particular 20 ethoxyl groups) ester of sorbitan, wherein the fatty acid is preferably selected from the group consisting of oleate (e.g. ethoxylated sorbitan monooleate such as Tween 81® and/or ethoxylated sorbitan trioleate such as Tween 85®), palmitate, stearate (e.g. ethoxylated sorbitan tristearate such as Tween 65®), isostearate, laurate and the combinations thereof; ethoxylated fatty alcohols (in particular 5-10 ethoxyl groups) (e.g. Brij 76®, Brij 56®, Brij 96®), ethoxylated fatty acids (in particular 5-10 ethoxyl groups) (e.g. Simulsol 2599®, Myrj 45®), ethoxylated castor oil (in particular 25-35 ethoxyl groups) (e.g. Arlatone 650®, Arlatone G®, Cremophor EL®), and combinations thereof.

In one embodiment of the composition of the invention, the non-ionic hydrophilic surfactant:
a. is a mono-, di or triglyceride, preferably an ethoxylated triglyceride, and/or
b. has a hydrophilic-lipophilic balance (HLB) value between 9 and 14.

The HLB value is calculated using the formula $HLB=20(1-I_s/I_a)$, in which $I_s$ represents the saponification index or saponification value and $I_a$ represents the acid index or acid value of said surfactant or of said mixture of surfactants. These two indices, saponification and acid values, are determined by methods described in the European Pharmacopoeia (Edition 8.8, section 2.5.6 and 2.5.1, respectively).

In a preferred embodiment, the non-ionic hydrophilic surfactants is ethoxylated castor oil, more in particular polyoxyl 35 hydrogenated castor oil or polyoxyethyleneglyceroltriricinoleate 35 (CAS no. 61791-12-6) (e.g.

Cremophor EL®) which is a mixture of polyoxyethylated triglycerides obtained by reacting castor oil with ethylene oxide in a molar ration of 1:35.

Preferably, the reconstitution composition of the invention comprises or consists of about 75% v/v aqueous solution comprising about 0.1M citric acid in water, about 6.25% v/v propylene glycol (CAS no. 57-55-6), about 12.5% v/v ethanol and about 6.25% v/v polyoxyethyleneglyceroltriricinoleate 35 (CAS no. 61791-12-6). In other words, the reconstitution composition comprises or consist of about 0.075M citric acid, about 6.25% v/v propylene glycol (CAS no. 57-55-6), about 12.5% v/v ethanol and about 6.25% v/v polyoxyethyleneglyceroltriricinoleate 35 (CAS no. 61791-12-6) in water.

Also preferred is a reconstitution composition comprising or consisting of about 75% v/v aqueous solution comprising about 0.1M citric acid in water, about 6.25% v/v propylene glycol (CAS no. 57-55-6), about 12.5% v/v ethanol, about 6.25% v/v polyoxyethyleneglyceroltriricinoleate 35 (CAS no. 61791-12-6) and 20 µg/mL CpG ODN1826, or comprising or consisting of about 0.075M citric acid, about 6.25% v/v propylene glycol (CAS no. 57-55-6), about 12.5% v/v ethanol, about 6.25% v/v polyoxyethyleneglyceroltriricinoleate 35 (CAS no. 61791-12-6) and 20 µg/mL CpG ODN1826 in water.

The reconstitution composition is in particular suitable for reconstituting stored peptides as defined herein below under Pharmaceutical composition, i.e. preferably having a length of between 15 and 100 amino acids. The difficulty to form stable solutions upon reconstitution of peptides of the length defined above is appreciated in the art, especially in case of different peptides, i.e. peptides having different amino acid sequences and hence have different chemical properties and behave physically different. As a result, it is hard to reconstitute them in one and the same solution. On top of that, in case one or more of these peptides comprise cysteines, the tendency to form SS-bridges has to be dealt with. Although intramolecular disulfide bonds may be required in vaccine peptides in order to be immunogenic, intermolecular disulfide bridge formation is undesirable as it results in instable solutions.

The inventors now have identified that the reconstitution composition of the present invention is in particular suitable for forming highly stable reconstituted peptides compositions wherein the amount of intermolecular disulfide bridges is minimalized, without compromising on immunogenicity of the reconstituted peptides. Therefore, the reconstitution composition of the invention prevents intermolecular disulfide formation of the peptides to be reconstituted as further defined herein, without comprising on immunogenicity of these peptides.

Preferably, the reconstitution composition of the invention is a sterile and/or pharmaceutical-grade or clinical-grade composition, suitable for parental administration to a subject, i.e. a mammalian species or human being. Preferably, the reconstitution composition of the invention is manufactured using Good Manufacturing Practice (GMP) and has GMP quality as defined by both the European Medicines Agency and the Food and Drug Administration. The reconstitution composition of the invention may be packaged in a vial. The invention also provides for a vial comprising a volume of reconstitution composition suitable for reconstituting a single pharmaceutical dosage unit as further defined herein, or multiples thereof, i.e. a volume suitable for reconstituting a 2, 3, 4, 5, 6, 7, 8, 9, 10 or more pharmaceutical dosage units. Preferably, said vial is stored at a temperature at which the reconstitution composition is stable for at least 1 month, 2 months, 3 months, 6 months or 1 year or even 2 years. Preferably, said temperature is between −25° C. and 25° C., or between −23° C. and −18° C., or between 0° C. and 10° C., or between 2° C. and 8° C., or between 18° C. and 23° C.

Preferably, the volume of reconstitution composition of the invention present in the vial is at most 50 mL, preferably between 0.1 and 10 mL, preferably between 1 and 10 mL, such as, 0.5, 1, 2, 3, 4, 5 or 10 mL, or any value in between. A vial is to be understood herein as a container that can have any shape. Optionally, a vial is to be understood herein as a syringe.

Pharmaceutical Composition

The reconstitution composition of the invention is in particular suitable for reconstituting peptides for the preparation of a medicament or pharmaceutical composition. Such pharmaceutical composition may be a vaccine, preferably a peptide vaccine. A "vaccine" is to be understood herein as a composition comprising antigenic compounds, optionally complemented with further immune stimulating compounds, for generating immunity for the prophylaxis and/or treatment of diseases such as conditions associated with persistent infection and/or metaplasia and/or dysplasia and/or neoplasia. A "peptide-based vaccine" or "peptide vaccine" (these terms are used herein interchangeably) is to be understood herein as a vaccine wherein peptides constitute the active ingredients, i.e. the antigenic compounds. Preferably, such peptides are synthetic long peptides. More preferably, comprising Human Leukocyte Antigen (HLA)-epitopes capable of inducing CD4+ and/or CD8+ T cell responses.

Therefore, provided is a pharmaceutical composition comprising peptides reconstituted in the reconstitution composition of the invention. Preferably, the pharmaceutical composition of the invention is a vaccine, preferably a peptide-based vaccine. Such a peptide-based vaccine may be used for the treatment of persistent infections, pre-cancerous conditions and cancer, preferably activating the cellular immune system to clear infected, pre-cancerous and/or cancerous cells that express viral antigens, Tumor-Associated-Antigens, like cancer testis antigens and/or Tumor-Specific antigens, like oncogenic or non-oncogenic viral antigens and/or neo-antigens resulting from DNA mutations.

The pharmaceutical composition is preferably for, and therefore formulated to be suitable for, administration to a subject, preferably a human or animal subject. Preferably, the administration is parenteral, e.g. intravenous, subcutaneous, intramuscular, intradermal intracutaneous and/or intratumoral administration, i.e. by injection.

The inventors found that the reconstitution composition comprising reconstituted peptides is in particular suitable for admixing with an oil-based adjuvant, resulting in a chemically and physically stable peptide-vaccine solution.

"Chemically stable" is referred herein in the context of a peptide solution and/or peptide-vaccine composition and is to be understood herein as a solution or composition comprising peptides that do not chemically degrade or decompose, for instance because of the formation of intra- or intermolecular disulfide bridges, to an unacceptable degree; i.e. the amount of un-degraded, un-decomposed and/or unreacted peptides within the solution and/or composition is at least 90%, 91%, 92%, 93%, 94%, 95%, 96%, 97%, 98%, 99% or even 100% by weight as compared to its original, after storage of the solution or composition for at least about 0.5, 1, 1.5, 2 or at least 3 hours at room temperature. Chemical stability can be assessed using any suitable technique known in the art, for instance using UPLC/MS as exemplified herein. When using UPLC/MS, a solution/composition is defined as chemically stable if the total % area of new peaks appearing after storage of at least about 0.5, 1, 1.5, 2 or at least 3 hours at room temperature is at most 20%, 15%, 10%, 9%, 8%, 7%, 6%, 5%, 4%, 3%, 2%, 1%, or 0% as compared to its original, wherein new peaks are understood to be the peaks on a UPLC chromatograms of the stored solution that were not identified on the UPLC chromatograms of the original ("original" being understood herein as the freshly prepared solution directly after preparation), when measured under the same conditions. Preferably, the total % area of new peaks appearing after storage of 3 hours at room temperature is at most 20%, 15%, 10%, 9%, 8%, 7%, 6%, 5%, 4%, 3%, 2%, 1%, or 0%, preferably at most 10% as compared to its original, when measured under the same conditions.

"Physically stable" is referred herein in the context of a peptide solution and/or peptide-vaccine composition and is to be understood herein as a solution or composition comprising peptides that do not precipitate or re-disperse. Physical stability can be assessed using any suitable technique known in the art, for instance by visual inspection or by particle distribution using a Malvern Mastersizer as exemplified herein, wherein average particle size is expressed in D(0.5). When using Malvern Mastersizer for assessing physical stability as exemplified herein, a solution/composition is defined as physically stable if the average D (0.5) after storage of at least about 0.5, 1, 1.5, 2 or at least 3 hours at room temperature is increased at most 50%, 40%, 30%, 20%, 10% or 5% as compared to its original (i.e. the freshly prepared solution directly after preparation). Preferably, a solution/composition is defined as physically stable if the average D(0.5) after storage of 3 hours at room temperature is increased at most 50%, 40%, 30%, 20%, 10% or 5%, preferably at most 20%, as compared to its original.

Preferably, the pharmaceutical composition of the invention further comprises an adjuvant. The term "adjuvant" is used herein to refer to substances that have immune-potentiating effects and are added to or co-formulated with an antigenic agent in order to enhance, induce, elicit, and/or modulate the immunological response against the antigenic agent when administered to a subject. Oil-based adjuvants can be used to form emulsions (e.g. water-in-oil or oil-in-water emulsions) and are appreciated in the art to enhance and direct the immune response. The presence of such adjuvant in a therapeutic vaccine is highly beneficial. Therefore, the present invention also provides for a pharmaceutical composition or medicament comprising or consisting of the reconstitution composition of the invention, reconstituted peptides and an oil-based adjuvant, more in particular the invention provides for a pharmaceutical composition comprising about 0.5-10 mg/mL peptides in about 40-60% v/v of the reconstitution composition of the invention and about 40-60% v/v of an oil-based adjuvant.

The oil-based adjuvant may be any mineral or non-mineral oil-based adjuvant known in the art. Preferably the oil-based adjuvant is a mineral oil-based adjuvant. Non-limiting examples of oil-based adjuvants are bio-based oil adjuvants (based on vegetable oil/fish oil, etc.), squalene-based adjuvant (e.g. MF59), Syntex Adjuvant Formulation (SAF; Lidgate, Deborah M, *Preparation of the Syntex Adjuvant Formulation (SAF, SAF-m, and SAF-1)*, In: *Vaccine Adjuvants, Volume* 42 *of the series Methods in Molecular Medicine*™ p 229-237, ISSN1543-1894), Freund's Complete Adjuvant (FCA), Freund's Incomplete Adjuvant (FIA), adjuvants based on peanut oil (e.g. Adjuvant 65), Lipovant (Byars, N. E., Allison, A. C., 1990. *Immunologic adjuvants: general properties, advantages, and limitations*. In: Zola, H. (Ed.), *Laboratory Methods in Immunology*. p 39-51), ASO4 (A. Tagliabue, R. Rappuoli *Vaccine adjuvants: the dream becomes real Hum. Vaccine*, 4 (5), 2008, p 347-349), Montanide adjuvants, which are based on purified squalene and squalene emulsified with highly purified mannide monooleate (e.g. Montanide ISA 25 VG, 28 VG, 35 VG, 50 V, 50 V2, 51 VG, 61 VG, 70 VG, 70 M VG, 71 VG, 720 VG, 760 VG, 763 A VG, 775 VG, 780 VG, 201 VG, 206 VG, 207 VG). Preferably the oil-based adjuvant is a mineral oil-based adjuvant. More preferably, the oil-based adjuvant is Montanide ISA 51VG (Seppic), which is a mixture of Drakeol VR and mannide monooleate.

Preferably, the pharmaceutical composition comprises or consists of an amount of peptides that constitutes a pharmaceutical dosage unit. A pharmaceutical dosage unit is defined herein as the amount of active ingredients (i.e. the total amounts of peptides in a peptide-based vaccine) that is applied to a subject at a given time point. A pharmaceutical dosage unit may be applied to a subject in a single volume, i.e. a single shot, or may be applied in 2, 3, 4, 5 or more separate volumes or shots that are applied preferably at different locations of the body, for instance in the right and the left limb. Reasons for applying a single pharmaceutical dosage unit in separate volumes may be multiples, such as avoid negative side effects, avoiding antigenic competition and/or composition analytics considerations. It is to be understood herein that the separate volumes of a pharmaceutical dosage may differ in composition, i.e. may comprise different kinds or composition of active ingredients and/or adjuvants. It is to be understood that for all active ingredients (antigenic peptides) within the whole pharmaceutical dosage unit a single reconstitution composition is used, as one of the benefits of the invention is that the reconstitution composition of the invention is suitable for reconstituting, and subsequent emulsification using an oil-based adjuvant, of different peptide mixtures. A single reconstitution composition, and preferably a single oil-based adjuvant, minimizes the chance of human failure in reconstitution and emulsification.

A single injection volume or shot (i.e. volume applied on one location at a certain time point), comprising a total pharmaceutical dosage, or part thereof in case multiple shots applied at substantially the same time point, may between 100 μL and 2 mL, or between 100 μL and 1 mL. The single injection volume may be 100 μL, 200 μL, 300 μL, 400 μL, 500 μL, 600 μL, 700 μL, 800 μL, 900 μL, 1 mL, 1.1 mL, 1.2 mL, 1.3 mL, 1.4 mL, 1.5 mL, 1.6 mL, 1.7 mL, 1.8 mL, 1.9 mL, 2 mL, 3 mL or any value in between.

A pharmaceutical dosage unit may be an effective amount or part of an effective amount. An "effective amount" is to be understood herein as an amount or dose of active ingredients required to prevent and/or reduce the symptoms of a disease (e.g., chronic infection, pre-cancerous condition and/or cancer) relative to an untreated patient. The effective amount of active compound(s) used to practice the present invention for preventive and/or therapeutic treatment of a disease or condition varies depending upon the manner of administration, the age, body weight, and general health of the subject. Ultimately, the attending physician or veterinarian will decide the appropriate amount and dosage regimen. Such amount is referred to as an "effective" amount. This effective amount may also be the amount that is able to induce an effective cellular T cell response in the subject to be treated, or more preferably an effective systemic cellular T cell response.

Preferably, pharmaceutical dosage unit, or total amount of peptides applied to a subject at a given time point, either in a single or in multiple injections at a certain time point, comprises an amount of peptides in the range from 0.1 µg to 20 mg, such as about 0.1 µg, 0.5 µg, 1 µg, 5 µg, 10 µg, 15 µg, 20 µg, 30 µg, 40 µg, 50 µg, 60 µg, 70 µg, 80 µg, 90 µg, 100 µg, 150 µg, 200 µg, 250 µg, 300 µg, 350 µg, 400 µg, 450 µg, 500 µg, 650 µg, 700 µg, 750 µg, 800 µg, 850 µg, 900 µg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 15 mg or about 20 mg or any value in between. Preferred ranges of pharmaceutical dosage units are from 0.1 µg to 20 mg, 1 µg to 10 mg, 10 µg to 5 mg, 0.5 mg to 2 mg, 0.5 mg to 10 mg or 1 mg to 5 mg or 2 to 4 mg.

Preferably, the pharmaceutical composition comprises or consists of about 1-2 mg/mL peptides in 40-60% v/v of the reconstitution composition as defined above and 40-60% v/v of an oil-based adjuvant. The pharmaceutical composition may comprise or consist about 40%, 41%, 42%, 43%, 44%, 45%, 46%, 47%, 48%, 49%, 50%, 51%, 52%, 53%, 54%, 56%, 57%, 58%, 59% or 60% v/v of an oil-based adjuvant. Preferably, the pharmaceutical composition comprises or consists of about 1-2 mg/mL peptides in about 50% v/v of the reconstitution composition as defined above and about 50% v/v of an oil-based adjuvant, preferably Montanide ISA 51 VG (Seppic). In other words, preferably, the pharmaceutical composition comprises or consists of about 1-2 mg/mL peptide, 0.038M citric acid, about 3.13% v/v propylene glycol (CAS no. 57-55-6), about 6.25% v/v ethanol, about 3.13% v/v polyoxyethyleneglyceroltriricinoleate 35 (CAS no. 61791-12-6) and about 50% of an oil-based adjuvant, preferably Montanide ISA 51 VG (Seppic), in water.

The pharmaceutical composition of the invention may comprise one or more further immune response stimulating compounds or adjuvants. Advantageously, the medicament according to the invention may additionally comprise one or more synthetic adjuvants. Such a further immune response stimulating compound or adjuvant may be (i) admixed to the pharmaceutical composition according to the invention after reconstitution of the peptides and optional emulsification with an oil-based adjuvant as defined above, (ii) may be part of the reconstitution composition of the invention defined above, (iii) may be physically linked to the peptide(s) to be reconstituted or (iv) may be administered separately to the subject, mammal or human, to be treated. It is to be construed herein that when an immune response stimulating compound is admixed to the medicament according to the invention, it is depicted as an adjuvant; when administered separately, it is depicted as an immuno-modulatory agent, or an immuno-modulator, which terms are used herein interchangeably. Particularly preferred are adjuvants that are known to act via the Toll-like receptors and/or via a RIG-I (Retinoic acid-Inducible Gene-1) protein and/or via an endothelin receptor. Immune modifying compounds that are capable of activation of the innate immune system can be activated particularly well via Toll like receptors (TLRs), including TLRs 1-10. Compounds capable of activating TLR receptors and modifications and derivatives thereof are well documented in the art. TLR1 may be activated by bacterial lipoproteins and acetylated forms thereof, TLR2 may in addition be activated by Gram positive bacterial glycolipids, LPS, LPA, LTA, fimbriae, outer membrane proteins, heat shock proteins from bacteria or from the host, and Mycobacterial lipoarabinomannans. TLR3 may be activated by dsRNA, in particular of viral origin, or by the chemical compound poly(I:C). TLR4 may be activated by Gram negative LPS, LTA, Heat shock proteins from the host or from bacterial origin, viral coat or envelope proteins, taxol or derivatives thereof, hyaluronan containing oligosaccharides and fibronectins. TLR5 may be activated with bacterial flagellae or flagellin. TLR6 may be activated by mycobacterial lipoproteins and group B Streptococcus heat labile soluble factor (GBS-F) or *Staphylococcus modulins*. TLR7 may be activated by imidazoquinolines, such as imiquimod, resiquimod and derivatives imiquimod or resiquimod (e.g. 3M-052). TLR9 may be activated by unmethylated CpG DNA or chromatin—IgG complexes. In particular TLR3, TLR7 and TLR9 play an important role in mediating an innate immune response against viral infections, and compounds capable of activating these receptors are particularly preferred in a the compositions or medicaments according to the invention. Particularly preferred adjuvants comprise, but are not limited to, synthetically produced compounds comprising dsRNA, poly(I:C), poly I:CLC, unmethylated CpG DNA which trigger TLR3 and TLR9 receptors, IC31, a TLR 9 agonist, IMSAVAC, a TLR 4 agonist, Montanide ISA-51, Montanide ISA 720 (an adjuvant produced by Seppic, France). RIG-I protein is known to be activated by ds-RNA just like TLR3 (Kato et al, (2005) *Immunity*, 1: 19-28). A particularly preferred TLR ligand is a pam3cys and/or derivative thereof, preferably a pam3cys lipopeptide or variant or derivative thereof, preferably such as described in WO2013051936A1, more preferably U-Pam12 or U-Pam14 or AMPLIVANT®. Further preferred adjuvants are Cyclic dinucleotides (CDNs), Muramyl dipeptide (MDP) and poly-ICLC. In a preferred embodiment, the adjuvants of the invention are non-naturally occurring adjuvants such as the pam3cys lipopeptide derivative as described in WO2013051936A1, Poly-ICLC, imidazoquinoline such as imiquimod, resiquimod or derivatives thereof, CpG oligodeoxynucleotides (CpG-ODNs) having a non-naturally occurring sequence, and peptide-based adjuvants, such as muramyl dipeptide (MDP) or tetanus toxoid peptide, comprising non-naturally occurring amino acids. Further preferred are adjuvants selected from the group consisting of: 1018 ISS, aluminum salts, Amplivax, AS 15, BCG, CP-870,893, CpG7909, CyaA, dSLIM, GM-CSF, IC30, IC31, ImuFact EV1P321, IS Patch, ISS, ISCOMATRIX, JuvImmune, LipoVac, MF59, monophosphoryl lipid A, Montanide IMS 1312, Montanide ISA 206, Montanide ISA 50V, OK-432, OM-174, OM-197-MP-EC, ONTAK, PepTel®, vector system, PLGA microparticles, SRL172, Virosomes and other Virus-like particles, Pam3Cys-GDPKHPKSF, YF-17D, VEGF trap, R848, beta-glucan, Aquila's QS21 stimulon, vadimezan, AsA404 (DMXAA), STING (stimulator of IFN genes) agonist (e.g. c-di-GMP VacciGrade™), PCI, NKT (natural killer T cell) agonist (e.g. alpha-galactosylceramide or alpha-GalCer, RNAdjuvant® (Curevac), retinoic acid inducible protein I ligands (e.g. 3pRNA or 5'-triphosphate RNA).

As indicated above, an adjuvant may be physically linked to the peptide(s) to be reconstituted. Physical linkage of adjuvants and costimulatory compounds or functional groups to antigenic peptides as defined herein below provides an enhanced immune response by improved targeting to antigen-presenting cells, in particular dendritic cells, that internalize, metabolize and display antigen and by simultaneously stimulating such cells to up-regulate expression of a variety of co-stimulatory molecules, thereby becoming efficient T cell response inducing and enhancing cells. Another preferred immune modifying compound is an inhibitor of an endothelin receptor such as BQ-788 (Buckanovich R J et al., (2008) *Nature Medicine* 14: 28; Ishikawa K, (1994) *PNAS* 91: 4892), and/or derivatives thereof.

BQ-788 is N-cis-2,6-dimethylpiperidinocarbonyl-L-gamma-methylleucyl-D-1-methoxycarbonyltryptophanyl-D-norleucine. Another preferred immune response stimulating compound or adjuvant is Interferon alpha (IFNα), more preferably pegylated Interferon alpha. Furthermore, the use of antigen presenting cell (co)stimulatory molecules, as set out in WO99/61065 and in WO03/084999, in combination with the peptides and compositions of the invention is preferred. In particular the use of 4-1BB and/or CD40 ligands, agonistic antibodies, OX40 ligands, CD27 ligands or functional fragments and derivatives thereof, as well as synthetic compounds with similar agonistic activity are preferably administered separately or combined with the peptides of the invention to subjects to be treated in order to further stimulate the mounting of an optimal immune response in the subject.

The peptides to be reconstituted in the reconstitution composition of the invention and/or comprised within the pharmaceutical composition of the invention, preferably have a length from about 15 to about 100 amino acids. Preferably, the peptides to be reconstituted are between 15-100 amino acids in length, or 15-95 amino acids, or 15-90 amino acids, or 15-85 amino acids, or 15-70 amino acids, or 15-65 amino acids, or 15-60 amino acids, or 15-55 amino acids, or 15-50 amino acids, or 15-45 amino acids, or 15-40 amino acids, or 17-39 amino acids, or 19-43 amino acids, or 22-40 amino acids, or 22-45 amino acids, or 28-40 amino acids or 30-39 amino acids in length. Preferably, the peptides to be reconstituted are at most 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, or 30 amino acids. Preferably, the peptides to be reconstituted are at least 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 amino acids. Preferably, the peptides to be reconstituted are at least 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 amino acids and no more than 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, or 30 amino acids, or any combination of these lower and upper limits.

The peptides to be reconstituted in the reconstitution composition of the invention and/or comprised within the pharmaceutical composition of the invention, may be peptides derived from protein antigens. A "protein antigen" is to be understood herein as a protein or polypeptide that comprises antigenic regions capable of inducing an immune response in a host animal or human. Protein antigens that are specifically expressed by infected, pre-cancerous and/or cancerous cells are suitable targets for therapeutic vaccines. Such protein antigens may be viral or non-viral antigens. Examples of viral antigens that are targets for prophylactic and therapeutic vaccines are antigens derived from Epstein Bar virus induced lymphoma's (EBV), Human T lymphotrophic virus I, Hepatitis B virus (HBV), Human papilloma virus (HPV), Kaposi sarcoma herpes virus (KSHV), Hepatitis C virus (HVC), KSV and Merkel cell carcinoma virus. Non-limiting examples of viral protein antigens are protein antigens from EBV, e.g. LMP1 or late membrane protein 1 (e.g. UniprotKB P03230) and LMP2 or late membrane protein 2 (e.g. UniprotKB P13285); protein antigens from Human T lymphotrophic virus I, e.g. Tax protein (e.g. UniprotKB P14079; P0C213; P03409); protein antigens from HBV e.g. genotypes A, B, C or D, e.g. protein HBsAg (e.g. UniprotKB Q773S4), X-protein (e.g. UniprotKB Q8V1H6) Large envelope protein (e.g. UniprotKB P03138) and capsid protein (e.g. UniprotKB P03147); protein antigens from HCV, e.g. genome polyprotein (e.g. UniprotKB P26663; Q99IB8; A3EZI9) and HCV protein (e.g. UniprotKB Q99398); protein antigens from HPV e.g. oncogenic genotypes 6, 11, 16 or 18, e.g. E6 oncoprotein (e.g. UniprotKB P03126; P06463) and E7 oncoprotein (e.g. UniprotKB P03129; P06788) protein antigens from KSHV, e.g. protein ORF36 (e.g. UniprotKB F5HGH5), Core gene UL42 family protein (e.g. UniprotKB Q77ZG5), Virion egress protein UL31 homolog (e.g. UniprotKB F5H982), Triplex capsid protein VP19C homolog (e.g. UniprotKB F5H8Y5), Viral macrophage inflammatory protein 2 (e.g. UniprotKB Q98157), mRNA export factor ICP27 homolog (e.g. UniprotKB Q2HR75), ORF52 (e.g. UniprotKB F5HBL8), Viral IRF4-like protein (e.g. UniprotKB Q2HR73), Bcl-2 (e.g. UniprotKB Q76RI8), Large tegument protein deneddylase (e.g. UniprotKB Q2HR64), V-cyclin (e.g. UniprotKB O40946), VIRF-1 (e.g. UniprotKB F5HF68) and E3 ubiquitin-protein ligase MIR1 (e.g. UniprotKB P90495) and antigen protein Merkel cell carcinoma virus, e.g. large T protein (e.g. UniprotKB E2IPT4; K4P159), e.g. small T protein (e.g. UniprotKB B6DVX0; B6DVX6).

Non-viral antigens that are suitable targets for prophylactic and therapeutic vaccines may be tumor specific antigens and/or tumor associated antigen. Tumor specific antigens are antigens that are exclusively expressed by tumor cells and not by any other cell and are often mutated proteins, such as $Kras^{G12D}$ and mutant P53, or neo-antigens developed in due course by DNA mutations and malfunctioning DNA repair mechanisms. Tumor associated antigens are endogenous antigens present in both tumor and normal cells but are dysregulated in their expression or cellular localization, such as the HER-2/neu receptor. Non limiting examples of such non-viral antigens that may be targets for therapeutic vaccines are Her-2/neu (or ErbB-2, Human Epidermal growth factor Receptor 2 (e.g. UniprotKB P04626); WT-1 or Wilms tumor protein (e.g. UniprotKB P19544); NY-ESO-1 or cancer/testis antigen 1 (e.g. UniprotKB P78358); MAGE-A3 or melanoma-associated antigen-A3 (e.g. UniprotKB P43357); BAGE or B melanoma antigen (e.g UniProtKB Q13072); CEA or carcinoembryonic antigen (e.g UniProtKB Q13984); AFP or α-fetoprotein (e.g UniProtKB P02771); XAGE-1B or X antigen family member 1 (e.g UniProtKB Q9HD64); survivin or BIRC5, Baculoviral IAP repeat-containing protein 5 (e.g. UniprotKB O15392); P53 (e.g. UniprotKB P04637); h-TERT or Telomerase reverse transcriptase (e.g. UniprotKB O14746); mesothelin (e.g. UniProtKB H3BR90); PRAME or Melanoma antigen preferentially expressed in tumors (e.g. UniprotKB P78395); MUC-1 or mucin-1 (e.g. UniprotKB P15941); Mart-1/Melan-A or Melanoma antigen recognized by T-cells 1 (e.g. UniprotKB Q16655); GP-100 or Melanocyte protein PMEL (e.g. UniprotKB P40967); tyrosinase (e.g. UniprotKB U3M8N0); tyrosinase-related protein-1 (e.g. UniprotKB P17643); tyrosinase-related protein-2 (e.g. UniprotKB O75767); PAP or PAPOLA, Poly(A) polymerase alpha (e.g. UniprotKB P51003); PSA or Prostate-specific antigen (e.g. UniprotKB P07288); PSMA or prostate-specific membrane antigen, or Glutamate carboxypeptidase 2 (e.g. UniprotKB Q04609).

Preferred tumor specific antigen targets for peptide-vaccines are viral oncogenes and neo-antigens. "Neo-antigen"

is to be understood herein as a tumor antigen that arises from a tumor-specific mutation(s) which alters the amino acid sequence of genome-encoded proteins. Neo-antigens can be identified by whole-genome sequencing elucidating all, or nearly all, mutated neo-antigens that are uniquely present in a cancer (or neoplasia or tumor) of an individual patient. This collection of mutated neo-antigens may be analyzed to identify a specific, optimized subset of mutated neo-epitopes for use as an antigen source for the development of a personalized cancer vaccine for treatment of the patient's cancer. Methods to identify such neo-antigens are described in WO2014/168874, which is incorporated herein by reference.

Peptides "derived" from an antigen protein is to be understood herein as to comprise a contiguous amino acid sequence selected from the antigen protein, which may be modified by deletion or substitution of one or more amino acids, by extension at the N- and/or C-terminus with additional amino acids or functional groups, which may improve bio-availability, targeting to T-cells, or comprise or release immune modulating substances that provide adjuvant or (co)stimulatory functions.

The peptide to be reconstituted and/or comprised within the pharmaceutical composition may comprise or consist of a non-naturally occurring sequence as a result of the synthesis of non-natural lengths or as a result of comprising additional amino acids not originating from the protein antigen where the peptide is derived for and/or as a result of comprising a modified amino acid and/or a non-naturally occurring amino acid and/or a covalently linked functional group such as a fluorinated group, a fluorocarbon group, a human toll-like receptor ligand and/or agonist, an oligonucleotide conjugate, PSA, a sugar chains or glycan, a pam3cys and/or derivative thereof preferably such as described in WO2013051936A1, CpG oligodeoxynucleotides (CpG-ODNs), Cyclic dinucleotides (CDNs), a DC pulse cassette, a tetanus toxin derived peptide, a human HMGB1 derived peptide; either within the peptide or appended to the peptide, as indicated above. The peptide of the invention may comprise 2-aminoisobutyric acid (Abu, an isostere of cysteine). A cysteine of the peptide of the invention may be replaced by Abu.

Preferably, a peptide to be reconstituted and/or comprised within the pharmaceutical composition of the invention, is an isolated peptide, wherein "isolated" does not reflect the extent to which the peptide is purified, but indicates that the peptide has been removed from its natural milieu (i.e., that has been subject to human manipulation), and may be a recombinantly produced peptide or a synthetically produced peptide.

The use of relatively short peptides is highly preferred for medical purposes as these can be efficiently synthesized in vitro, which is not possible or uneconomical for native proteins larger than approximately 100, i.e. 95, 96, 97, 98, 99, 100, 101, 102, 103, 104, 105 amino acids. Chemical synthesis of peptides is routine practice and various suitable methods are known to the skilled person. Chemical synthesis of peptides also overcomes the problems associated with recombinant production of intact proteins, which is difficult to standardize and requires extensive purification and quality control measures. Peptides with a length that exceeds the length of human leukocyte antigen (HLA) class I and class II epitopes (e.g. having a length as specified herein for peptides to be reconstituted and/or comprised within the pharmaceutical composition of the invention) are particularly advantageous for use as vaccine component because they are large enough to be taken up by professional antigen presenting cells (APC), in particular Dendritic cell (DC), as explained in WO02/070006, and processed in the DC before cell surface presentation of the contained HLA class I-presented and HLA class II-presented epitopes takes place. Therefore, the disadvantageous induction of T cell tolerance by the systemic presentation of minimal HLA class I-presented epitopes on non-antigen presenting cells (as shown in Toes et al., $Proc\ Natl\ Acad\ Sci$ (1996) USA 93(15):7855, and Toes et al., $Immunol$ (1996) 156(10):3911), is prevented by the application of peptides exceeding the length of human leukocyte antigen (HLA) class I and class II epitopes (as shown in Zwaveling et al., $J.\ Immunol.$ (2002) 169:350-358). As compared to vaccination with the peptides having a length as specified herein for peptides to be reconstituted and/or comprised within the pharmaceutical composition of the invention, therapeutic vaccination with full length proteins are likely to be less potent (Rosalia et al. $Eur.\ J.\ Immunol$ (2013) 43: 2554-2565).

Peptides to be reconstituted and/or comprised in a pharmaceutical composition of the invention are preferably peptides of about 15 to about 100 amino acids in length, also denominated herein as long peptides, that each exceed the length of human leukocyte antigen (HLA) class I and class II presented epitopes and that either on its own or mixed induce a combined CD4+ and CD8+ T cell response that is therapeutically successful and inducing cure in a high percentage of patients. Preferably, the long peptides of the invention are synthetic peptides, denominated herein as synthetic long peptides (SLPs).

A "CTL epitope" is understood herein as a linear fragment of a polypeptide antigen that is liberated from the source protein by proteasome mediated proteolytic cleavage and subsequently presented by an HLA class I molecule on the cell surface of an antigen presenting cell (APC), preferably a human antigen presenting cell. A CTL epitope of the invention is preferably capable of activating a $CD8^+$ T cell response. A CTL epitope typically comprises at least 8 up to 12, or exceptionally up to 13 or 14 amino acids. Preferably a CTL epitope consists of 8-14 amino acids, i.e. has a length of at least 8 up to 14 amino acids.

A "Th-cell epitope" is understood herein to be a linear peptide fragment that is recognized by an HLA class II molecule. A Th-cell epitope is capable of inducing a $CD4^+$ T cell response. An HLA class II-restricted $CD4^+$ T-helper cell (Th-cell) epitope typically comprises 15 up to 20, or exceptionally even more, amino acids. Preferably, an HLA class II-restricted T-helper cell epitope comprises 10-20 or 10-15 amino acids.

Most preferably, the Th-cell epitope of the peptide to be reconstituted and/or comprises in the pharmaceutical composition of the invention, is capable of activating a $CD4^+$ T-helper memory and/or $CD4^+$ T-helper effector response, i.e. activation of a CD45RO-positive $CD4^+$ T-helper cell. This will lead, by virtue of the 'license to kill' signal through CD40-triggering of DC (Lanzavecchia (1998) $Nature$, 393: 413) to a more robust $CD8^+$ effector and memory cytotoxic T cell response. In another setting the activated $CD4^+$ T-helper cells may activate non-HLA restricted killer cells of the immune system.

Within the context of the present invention "a peptide which comprises at most 100 consecutive amino acids from a protein antigen" means that the number of consecutive amino acids originating from the protein antigen and present in a peptide as defined herein, is 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, or 30 amino acids or less. Within the context of the present invention "a peptide which comprises at least 15 consecutive amino acids from a protein antigen" means that the number of consecutive amino acids originating from the protein antigen and present in a peptide as defined herein, is at least 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45 or more amino acids. Within the context of the present invention "a peptide which comprises 15-100 consecutive amino acids from a protein antigen" means that the number of consecutive amino acids originating from the protein antigen and present in a peptide as defined herein, is at least 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 amino acids and no more than 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, or 30 amino acids. More preferably, the length of the contiguous amino acid sequence from the protein antigen comprised within the peptide to be reconstituted is 15-100 amino acids, or preferably 15-95 amino acids, or 15-90 amino acids, or 15-85 amino acids, or 15-70 amino acids, or 15-25 amino acids, or 15-60 amino acids, or 15-55 amino acids, or 15-50 amino acids, even more preferably 15-45 amino acids, even more preferably, 15-40 amino acids, even more preferably 17-39, even more preferably 19-43 amino acids, even more preferably 22-40 amino acids, even more preferably 28-40 and even more preferably 30-39 amino acids.

Preferably, the pharmaceutical composition according to the invention does not comprise any peptides which fulfill both of the following properties:

a. the percentage of basic amino acid residues equals the percentage of acidic amino acid residues, and b. the percentage of hydrophobic amino acid residues is 48% or higher.

For the purposes of this embodiment, amino acid residues are classified as "acidic", "basic", "hydrophobic" or "neutral" as follows:

| Amino acid | Category |
|---|---|
| Asp | Acidic |
| Glu | Acidic |
| Arg | Basic |
| Lys | Basic |
| His | Basic |
| Ala | Hydrophobic |
| Phe | Hydrophobic |
| Leu | Hydrophobic |
| Ile | Hydrophobic |
| Val | Hydrophobic |
| Tyr | Hydrophobic |
| Trp | Hydrophobic |
| Cys | Neutral |
| Gly | Neutral |
| Met | Neutral |
| Pro | Neutral |
| Asn | Neutral |
| Gln | Neutral |
| Ser | Neutral |
| Thr | Neutral |

The peptides to be reconstituted and/or comprised within the pharmaceutical composition of the invention are preferably antigenic peptides. "Antigenic peptides" are to be understood herein as (highly) immunogenic and capable of inducing a potent combined antigen-directed CD4+ T helper and CD8+ cytotoxic T cell response, when administered as a vaccine composition to a subject, preferably a human or animal subject. The peptide may be predicted to be immunogenic and/or may be proven to be immunogenic using in vitro or ex vivo assays or by doing in vivo tests appreciated in the art to establish immunogenicity. Preferably, the peptide can be used effectively in the prevention, partial clearance and/or treatment or full clearance of an antigen related disease or condition in a subject, preferably as detectable by:

activation or an induction of the immune system and/or an increase in antigen specific activated CD4+ and/or CD8+ T-cells in peripheral blood or in tissues as established by Elispot assay or by tetramer staining of CD4+ or CD8+ T cells or an increase of the cytokines produced by these T-cells as established by intracellular cytokine staining of CD4+ and CD8+ T cells in flow cytometry after at least one week of treatment; and/or inhibition of proliferation of antigen related infection or a detectable decrease of antigen expressing cells or a decrease in cell viability of antigen expressing cells; and/or induction or increased induction of cell death of antigen expressing cells; and/or inhibition or prevention of the increase of antigen expressing cells.

In a preferred embodiment, a vaccine composition of the invention comprises a combination of peptides wherein said combination of peptides covers at least 70%, 80%, 90%, 92%, 94%, 95%, 96%, 97%, 98%, 99% or 100% of the HLA class I molecules that are encoded by HLA alleles predominant in the population of human subjects to be treated. HLA alleles that are predominant in the population of human subjects to be treated. Preferred HLA class I epitopes in peptides according to the invention are epitopes capable of binding to: HLA-A0101; HLA-A0201; HLA-A0206; HLA-A0301; HLA-A1101; HLAA2301; HLA-A2402; HLA-A2501; HLA-A2601; HLA-A2902; HLA-A3001; HLAA3002; HLA-A3101; HLA-A3201; HLA-A3303; HLA-A6801; HLA-A6802; HLAA7401; HLA-B0702; HLA-B0801; HLA-B1301; HLA-B1302; HLA-B1402; HLAB1501; HLA-B1502; HLA-B1525; HLA-B1801; HLA-B2702; HLA-B2705; HLAB3501; HLA-B3503; HLA-B3701; HLA-B3801; HLA-B3901; HLA-B4001; HLAB4002; HLA-B4402; HLA-B4403; HLA-B4601; HLA-B4801; HLA-B4901; HLAB5001; HLA-B5101; HLA-B5201; HLA-B5301; HLA-B5501; HLA-B5601; HLAB5701; HLA-B5801 and HLA-B5802. In a preferred embodiment, a peptide of the invention, covers at least 10%, 20%, 30%, 40%, 50%, 60%, 70%, 80%, 90%, or 100% of the HLA class I molecules that are encoded by HLA alleles predominant in the population of human subjects to be treated, wherein "Cover an HLA class I molecule" is understood herein as comprising a CTL epitope that shows binding affinity, preferably intermediate binding affinity, more preferably high binding affinity to said HLA class I molecule. Preferably, a peptide of the invention covers at least 10%, 20%, 30%, 40%, 50%, 60%, 70%, 80%, 90%, or 100% of group of HLA class I molecules consisting of: HLA-A0101; HLA-A0201; HLA-A0206; HLA-A0301; HLA-A1101; HLA-A2301; HLA-A2402; HLA-A2501; HLA-A2601; HLA-A2902; HLA-A3001; HLA-A3002; HLA-A3101; HLA-A3201; HLA-A3303; HLA-A6801; HLA-A6802; HLA-A7401; HLA-B0702; HLA-B0801; HLA-B1301; HLA-B1302; HLA-B1402; HLA-B1501; HLA-B1502; HLA-B1525; HLA-B1801; HLA-B2702; HLA-B2705; HLA-B3501; HLA-B3503; HLA-B3701; HLA-B3801; HLA-B3901; HLA-B4001; HLA-B4002;

HLA-B4402; HLA-B4403; HLA-B4601; HLA-B4801; HLA-B4901; HLA-B5001; HLA-B5101; HLA-B5201; HLA-B5301; HLA-B5501; HLA-B5601; HLA-B5701; HLA-B5801 and HLA-B5802.

The reconstitution composition can be used for reconstituting a single type of peptides (i.e. all having substantially the same, or the same amino acid sequence) or for mixtures of different peptides having different amino acid sequences. A pharmaceutical composition of the invention preferably comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 and up to 33 different peptides. "Different peptides" are to be understood herein as having a different amino acid sequences, preferably having less than 60%, 50%, 40%, or preferably less than 30% sequence identity, as determined over their whole length. The different peptides to be reconstituted and/or comprised within the pharmaceutical composition of the invention may be peptides having a length as defined herein above that together overlap the entire amino acid sequence of the protein antigen from which these peptides are derived. However, in some instances, immunization with the complete set of overlapping (synthetic) long peptides spanning the full length protein antigens is not feasible, and a selection needs to be made. To narrow the number of peptides in a vaccine, preferably the most immunogenic long peptides are selected and incorporated that are recognized by the highest percentage of patients.

At least one of the peptides to be reconstituted and/or comprised within the pharmaceutical composition of the invention may have at least one cysteine residue that is capable of intermolecular disulfide bridging, or may have at least two cysteine residues that are capable of intra- and inter-molecular disulfide bridge formation. Preferably, a vaccine composition according to the invention comprises a combination of peptides wherein said combination of peptides covers at least 70%, 80%, 90%, 92%, 94%, 95%, 96%, 97%, 98%, 99% or 100% of the HLA class I molecules that are encoded by HLA alleles predominant in the population of human subjects to be treated as defined herein above.

The amount of peptides to be reconstituted in the reconstitution composition of the invention preferably is a pharmaceutical dosage unit and/or amount to be injected in a single volume, as defined herein above.

Dried peptides may be peptides free of further constituents but may also comprise buffer components such as Trifluor acetic acid (TFA), salts such as sodium, potassium or phosphate salts (e.g. NaCl, KCl and NaPO$_4$). The amount of further constituents is preferably less than 30%, more preferably less than 25%, of the total weight of the dry peptides to be reconstituted. Dried peptides to be reconstituted may be in a physical dried state as can be obtained by processes such as, but not limited to, rotor evaporation, lyophilization (freeze drying) and spray drying.

Preferred protein antigens, from which the peptides to be reconstituted and/or comprised within the pharmaceutical composition of the invention are derived, are defined herein below.

HPV-Derived Peptides

The peptides to be reconstituted and/or comprised within the pharmaceutical composition of the invention may be (mixes of) peptides derived from the early HPV antigen proteins E2, E6 or E7. Preferably, the contiguous amino acid sequence is selected from the full length amino acid sequences of the HPV E6 and E7 proteins from a high risk HPV serotype, such as serotypes 16, 18, 31, 33 or 45, more preferably from the amino acid sequences of the HPV E6 and E7 serotypes 16, 18, 31 or 33, most preferably from serotypes 16 or 18, of which 16 is most preferred. The amino acid sequence of the HPV serotype 16 E2 (UniProtKB-P03120), E6 (UniProtKB-P03126) and E7 (UniProtKB-P03129) proteins are depicted in SEQ ID NO: 14-16, respectively. The amino acid sequence of the HPV serotype 18 E2 (UniProtKB-P06790), E6 (UniProtKB-P06463) and E7 (UniProtKB-P06788) proteins are depicted in SEQ ID NO: 17-19, respectively.

Preferred peptides and peptide mixes to be reconstituted and/or comprised within the pharmaceutical composition of the invention and derived from HPV E6 and E7 proteins are as defined in WO00/75336 A2. Preferred peptides are peptides comprising or consisting of a contiguous sequence within an immunogenic region represented by any one of SEQ ID NO: 20-26.

Preferably, one or more peptides to be reconstituted and/or comprised within the pharmaceutical composition of the invention comprises a CTL epitope selected from the group represented by SEQ ID NO: 27-67.

Preferred peptides and peptide mixes to be reconstituted and/or comprised within the pharmaceutical composition of the invention and derived from HPV E2, E6 and E7 proteins are as defined in WO2002/070006 A2 and WO2002/090382, which is incorporated herein by reference. Preferred peptides are peptides comprising or consisting of a contiguous sequence within the following HPV immunogenic regions E2 (31-120); E2 (151-195); E2 (271-365); E6 (81-158); E7 (31-77), preferably of the HPV16 serotype and defined herein by SEQ ID NO: 68-72, respectively.

Preferably, one or more peptides to be reconstituted and/or comprised within the pharmaceutical composition of the invention comprises a Th epitope that is selected from DR1/E2 351-365, DR2/E2 316-330, DR2/E2 346-355, DR4/E2 51-70, E2 61-76, DQ6/E2 311-325, DR15/E7 50-62, DR3/E7 43-77, DQ2/E7 35-50 and DR1/E6 127-142 (represented herein by SEQ ID NO: 73-82, respectively).

Preferably, the peptides to be reconstituted and/or comprised within the pharmaceutical composition of the invention comprise at least one T cell epitope that is recognized by a T cell that infiltrates a cervical neoplastic lesion or by a T cell that is present in or isolated from a lymph node from the pelvic region, that is draining from the cervical neoplastic lesion. Preferably, the T cell epitope is present in or isolated from a draining lymph node comprising metastatic tumor cells. Such epitopes are disclosed in e.g., WO2008/147187 A1, US20060182762A1, WO2006013336A1, WO2009148230A2, WO2009148229A2, WO2002044384A2 which is incorporated herein by reference.

In yet a preferred peptide to be reconstituted and/or comprised within the pharmaceutical composition of the invention, the contiguous amino acid sequence comprises an epitope that is selected from the group consisting of a contiguous amino acid sequence selected from the group consisting of the amino acid sequences represented by SEQ ID NO: 83-104, which have been proven to be T-cell epitopes that are recognized by a T cells that infiltrates a cervical neoplastic lesion or by a T cell from a draining lymph node.

A preferred class II CD4$^+$ Th cell epitope comprised in a peptide to be reconstituted and/or comprised within the pharmaceutical composition of the invention is selected from the group consisting a contiguous amino acid sequence selected from the group consisting of the amino acid sequences represented by SEQ ID NO: 83-99.

A preferred class I CD8$^+$ CTL cell epitope comprised in a peptide to be reconstituted and/or comprised within the pharmaceutical composition of the invention is selected from the group consisting a contiguous amino acid sequence selected from the group consisting of the amino acid sequences represented by SEQ ID NO: 85, 82, 100-104.

Preferred peptides to be reconstituted and/or comprised within the pharmaceutical composition of the invention comprise or consist of a contiguous amino acid sequence selected from the group consisting of the amino acid sequences represented by SEQ ID NO: 1-13.

Preferred mixes of peptides to be reconstituted and/or comprised within a vaccine composition of the invention are mixes of peptides that have at least 1, 2, 3, 4 or 5 of the peptides comprising or consisting of the sequences selected from SEQ ID NO: 1-5; at least 1, 2, 3, 4, 5 or 6 of the peptides comprising or consisting of a contiguous amino acid sequence selected from the group consisting of the amino acid sequences represented by SEQ ID NO: 1-6; and at least 1, 2, 3, 4, 5, 6 or 7 of the peptides comprising or consisting of a contiguous amino acid sequence selected from the group consisting of the amino acid sequences represented by SEQ ID NO: 7-13. Preferably, the pharmaceutical composition comprises a mixture of peptides having sequence SEQ ID NO: 1-5 or SEQ ID NO: 1-6 or SEQ ID NO: 7-13. Preferably, the different peptides in the mixture are present in the pharmaceutical composition in substantially equal ratios.

HBV-Derived Peptides

The peptides to be reconstituted and/or comprised within the pharmaceutical composition of the invention may be (mixes of) peptides derived from the various genotypes, e.g. from the HBV-A proteins, HBV polymerase (UniProtKB-P03159), HBV core protein (UniProtKB-POC625), HBV X protein, and HBV large surface protein (UniProtKB-P03141), which are represented herein by SEQ ID NO: 105-108. Preferred peptides, peptides mixes and epitopes present within these peptides have been disclosed in e.g. WO2015/187009, WO2014/102540 A1, WO 93/03753, WO 95/03777, US2010/0068228A1, US2009/0311283 A1, which are incorporated herein by reference.

Preferred, one or more peptides to be reconstituted and/or comprised within the pharmaceutical composition of the invention comprise or consist of an amino acid sequence selected from the group consisting of SEQ ID NO: 109-146.

Preferably, the peptide to be reconstituted and/or comprised within the pharmaceutical composition of the invention comprises or consist of a peptide selected from the group consisting of SEQ ID NO: 109, 113, 118, 121, 122, 126, 129, 132, 133, 134, 135, 138 and 142, more preferably selected from the group consisting of SEQ ID NO: 109, 113, 118, 121, 122, 126, 129, 132, 133, 135, 138 and 142, even more preferably selected from the group consisting of SEQ ID NO: 113, 118, 121, 122, 126, 129, 132, 133, 134, 135 and 142, even more preferably selected from the group consisting of SEQ ID NO: 113, 118, 121, 122, 126, 129, 132, 133, 135 and 142, even more preferably selected from the group consisting of SEQ ID NO: 118, 121, 129, 132, 133 and 142, most preferably selected from the group of SEQ ID NO: 133, 142 and 121. Preferably, the one or more peptides to be reconstituted and/or comprised within the pharmaceutical composition of the invention comprises or consists of a peptide selected from the group consisting of SEQ ID NO: 109, 118, 121, 122, 126, 129, 132-135. Preferably, the one or more peptides to be reconstituted and/or comprised within the pharmaceutical composition of the invention comprises or consists of a peptide selected from the group consisting of SEQ ID NO: 122, 129 and 133.

Preferred mixes of peptides to be reconstituted and/or comprised within a vaccine composition of the invention are mixes of peptides at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 and up to 33 different peptides of the peptides consisting of or comprising of a peptide selected from the group consisting of SEQ ID NO: 109-146, more preferably selected from the group consisting of SEQ ID NO: 109, 113, 118, 121, 122, 126, 129, 132, 133, 134, 135, 138 and 142, more preferably selected from the group consisting of SEQ ID NO: 109, 113, 118, 121, 122, 126, 129, 132, 133, 135, 138 and 142, even more preferably selected from the group consisting of SEQ ID NO: 113, 118, 121, 122, 126, 129, 132, 133, 134, 135 and 142, even more preferably selected from the group consisting of SEQ ID NO: 113, 118, 121, 122, 126, 129, 132, 133, 135 and 142, even more preferably selected from the group consisting of SEQ ID NO: 118, 121, 129, 132, 133 and 142, most preferably selected from the group of SEQ ID NO: 133, 142 and 121. Further preferred is a composition that comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 and up to 33 different peptides of the peptides consisting of or comprising of a peptide selected from the group consisting of SEQ ID NO: 109, 118, 121, 122, 126, 129, 132-135, more preferably selected from the group consisting of SEQ ID NO: 121, 129 and 133. Further preferred mixes to be reconstituted and/or comprised within the pharmaceutical composition of the invention are a mix comprising a peptide that comprises or consists of a peptide of SEQ ID NO: 121 in combination with a peptide that comprises or consists of at least one of SEQ ID NO: 139, 140, 133, 139, 142, 118, 129; and a mix comprising a peptide that comprises or consists of a peptide of SEQ ID NO: 133 in combination with a peptide that comprises or consists of at least one of SEQ ID NO: 139, 140, 63, 139, 142, 118, 129. Preferably, the different peptides in the mixture are present in the pharmaceutical composition in substantially equal ratios.

PRAME-Derived Peptides

The peptides to be reconstituted and/or comprised within the pharmaceutical composition of the invention may be (mixes of) peptides derived from PRAME (UniProtKB-P78395), which is represented herein by SEQ ID NO: 147. Preferred peptides, peptides mixes and epitopes present within these peptides have been disclosed in e.g., WO 2008/118017 A2 which is incorporated herein by reference. Preferably, one or more of the peptides to be reconstituted comprise or consist a peptide selected from the group consisting of the amino acid sequence defined by SEQ ID NO: 148-167. Preferred mixes of peptides to be reconstituted and/or comprised within a vaccine composition of the invention are mixes at least 2, 3, 4, 5, 6, 7, 8, 9, 10, 11, 12, 13, 14, 15, 16, 17, 18, 19 or 20 different peptides selected from SEQ ID NO: 148-167.

Preferably, the one or more peptides to be reconstituted and/or comprised within the pharmaceutical composition of the invention comprises a Th epitope that is selected from SEQ ID NO: 168-169.

P53-Derived Peptides

The peptides to be reconstituted and/or comprised within the pharmaceutical composition of the invention may be (mixes of) peptides derived from P53 (e.g. UniprotKB P04637), which is represented by SEQ ID NO: 190. Preferred peptides, peptides mixes and epitopes present within these peptides have been disclosed in e.g., WO 2008/147186 A2, which is incorporated herein by reference. Preferably, one or more of the peptides to be reconstituted comprise or consist a peptide selected from the group consisting of the amino acid sequence defined by SEQ ID NO: 191-211, more preferably selected from the group consisting of the amino acid sequence defined by SEQ ID NO: 191-204.

Preferred mixes of peptides to be reconstituted and/or comprised within a vaccine composition of the invention are mixes at least 2, 3, 4, 5, 6, 7, 8, 9, 10, 11, 12, 13, 14, 15, 16, 17, 18, 19 or 20 different peptides selected from SEQ ID NO: 191-211.

PSMA-Derived Peptides

The peptides to be reconstituted and/or comprised within the pharmaceutical composition of the invention may be (mixes of) peptides derived from PSMA (e.g. UniprotKB Q04609), which is represented herein by SEQ ID NO: 212. Preferred peptides, peptides mixes and epitopes present within these peptides have been disclosed in e.g., WO 2013/006050 A1, which is incorporated herein by reference. Preferably, one or more of the peptides to be reconstituted comprise or consist a peptide selected from the group consisting of the amino acid sequence defined by SEQ ID NO: 213-232.

Preferred mixes of peptides to be reconstituted and/or comprised within a vaccine composition of the invention are mixes at least 2, 3, 4, 5, 6, 7, 8, 9, 10, 11, 12, 13, 14, 15, 16, 17, 18, 19 or 20 different peptides selected from SEQ ID NO: 213-232.

Also comprised within the preferred antigen proteins, peptides to be reconstituted and epitopes within these peptides are antigen proteins, peptides and epitopes that show substantial identity to any of the specific antigen proteins, peptides and epitopes defined herein. Sequence identity is herein defined as a relationship between two or more amino acid sequences (polypeptide or protein), as determined by comparing the sequences. In the art, "identity" also means the degree of sequence relatedness between amino acid sequences as determined by the match between strings of such sequences. Sequence identity can be determined by alignment of two peptide sequences using global or local alignment algorithms, depending on the length of the two sequences. Sequences of similar lengths are preferably aligned using a global alignment algorithms (e.g. Needleman Wunsch) which aligns the sequences optimally over the entire length, while sequences of substantially different lengths are preferably aligned using a local alignment algorithm (e.g. Smith Waterman). Sequences may then be referred to as "substantially identical" when they (when optimally aligned by for example the programs GAP or BESTFIT using default parameters) share at least a certain minimal percentage of sequence identity (as defined below). GAP uses the Needleman and Wunsch global alignment algorithm to align two sequences over their entire length (full length), maximizing the number of matches and minimizing the number of gaps. A global alignment is suitably used to determine sequence identity when the two sequences have similar lengths. Generally, the GAP default parameters are used, with a gap creation penalty=50 (nucleotides)/8 (proteins) and gap extension penalty=3 (nucleotides)/2 (proteins). For proteins the default scoring matrix is Blosum62 (Henikoff & Henikoff, 1992, PNAS 89, 915-919). Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA, or using open source software, such as the program "needle" (using the global Needleman Wunsch algorithm) or "water" (using the local Smith Waterman algorithm) in EmbossWIN version 2.10.0, using the same parameters as for GAP above, or using the default settings (both for 'needle' and for 'water', the default Gap opening penalty is 10.0 and the default gap extension penalty is 0.5; default scoring matrices are Blossum62 for proteins). When sequences have a substantially different overall length, local alignments, such as those using the Smith Waterman algorithm, are preferred.

Alternatively, percentage identity may be determined by searching against public databases, using algorithms such as FASTA, BLAST, etc. Thus, the protein sequences of the present invention can further be used as a "query sequence" to perform a search against public databases to, for example, identify other family members or related sequences. Such searches can be performed using the BLASTp and BLASTx programs (version 2.0) of Altschul, et al. (1990) *J. Mol. Biol.* 215:403-10. BLAST protein searches can be performed with the BLASTx program, score=50, wordlength=3 to obtain amino acid sequences homologous to protein molecules of the invention. To obtain gapped alignments for comparison purposes, Gapped BLAST can be utilized as described in Altschul et al., (1997) *Nucleic Acids Res.* 25(17): 3389-3402. When utilizing BLAST and Gapped BLAST programs, the default parameters of the respective programs (e.g., BLASTx and BLASTp) can be used. See the homepage of the National Center for Biotechnology Information at http://www.ncbi.nlm.nih.gov/.

An antigen protein, peptide or epitope that show substantial identity to its related antigen protein, peptide or epitope defined herein is to be understood herein to have at least 70%, 75%, 80%, 85%, 90%, 91%, 92%, 93%, 94%, 95%, 96%, 97%, 98%, or 99% identity to any one of the specific sequences referred to herein, based on the full length of said specific sequence (i.e. over its whole length or as a whole).

Medical Use

Provided is a method for preventing or treating a persistent or chronic infection, pre-cancerous disorder and/or cancer. In other words, provided is the pharmaceutical composition of the invention as defined herein above for use as a medicament, preferably for the prevention or treatment of a persistent or chronic infection, pre-cancerous disorder and/or cancer. Such method or use comprises the step of administrating the pharmaceutical composition of the invention to a subject that is in need of such prevention and/or treatment. A subject in need of prevention and/or treatment may also be referred to as a patient, and may refer to an animal such as a mammal, including, but not limited to, a human or a non-human mammal, such as a non-human primate, bovine, equine, canine, ovine, or feline.

Preferably, a pharmaceutical dosage unit as defined herein above is provided. As also indicated herein above, this pharmaceutical dosage unit may be given once in a single shot or as multiple volumes administered at different locations. For example, a pharmaceutical dosage unit may be divided over two shots each administered in one of the two legs or arms of the subject to be treated. The two shots may comprise the same or different peptides mixes. For instance, a first shot may comprise SEQ ID NO 1-5 or SEQ ID NO: 1-6 and a second shot may comprise SEQ ID NOs 7-13, wherein both shots are administered at a single or substantially single time point, wherein substantially single time point is to be understood as within at most about 15 minutes, preferably, within at most 2 minutes.

The administration of the single or multiple shot may be carried out once or alternatively may be repeated subsequently, such as, but not limited to, daily, bi-weekly, weekly, once every two weeks, once every three weeks, once every four weeks, once every five weeks, once every six weeks, monthly, once per 2 months, once per 3 months, once per 4 months, once per 5 months, once per 6 months, once per 7 months, once per 8 months, once a year, once per 2 years, once per 5 years or once per 10 years.

Preferably, the pharmaceutical composition is administered in an effective amount as defined herein above. Preferably, the pharmaceutical composition of the invention is for intravenous or subcutaneous, or intramuscular administration, although other administration routes can be envisaged, such as mucosal administration or intradermal and/or intracutaneous administration or intratumoral administration, e.g., by injection. The pharmaceutical composition of the invention may be administered by a single administration. Alternatively, the administration may be repeated if needed and/or distinct peptides or peptide mixes or composition comprising different peptides or peptide mixes may be sequentially administered, wherein sequentially may be in time and/or location.

Preferably, the pharmaceutical composition is a vaccine composition for inducing a T cell response against at least one epitope comprised in a peptide. Preferably, the vaccine is for the prevention, partial clearance and/or treatment or full clearance of a antigen associated disease or condition in a subject, e.g. a persistent infection, cancerous (neoplasia) or precancerous disorder, preferably as detectable by:

activation or an induction of the immune system and/or an increase in antigen specific activated CD4+ and/or CD8+ T-cells in peripheral blood or in tissues as established by Elispot assay or by tetramer staining of CD4+ or CD8+ T cells or an increase of the cytokines produced by these T-cells as established by intracellular cytokine staining of CD4+ and CD8+ T cells in flow cytometry after at least one week of treatment; and/or inhibition of proliferation of antigen related infection or a detectable decrease of antigen expressing cells or a decrease in cell viability of antigen expressing cells; and/or induction or increased induction of cell death of antigen expressing cells; and/or inhibition or prevention of the increase of antigen expressing cells.

Examples of cancers to be prevented and/or treated via a method of the invention include, without limitation, cervical intraepithelial neoplasia (CIN), Vulvar intraepithelial neoplasia (VIN), vaginal intraepithelial neoplasia (VaIN), anal intraepithelial neoplasia (AIN), and penal intraepithelial neoplasia (PIN), as well as cancer of the cervix, vulva, vagina, anus, penis, aerodigestive track, and head & neck; liver cancer, leukemia (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, uterine cancer, testicular cancer, lung carcinoma, small cell lung carcinoma, non-small cell lung carcinoma, bladder carcinoma, multiple myeloma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma).

The method of the invention may be part of a combination therapy, which may be provided as a separate treatment or added to the pharmaceutical composition of the invention. The method of the invention may be combined with checkpoint control blockers, monoclonal antibodies (mAbs) targeting selected TNF receptor family members (e.g. CD40, 4-1 BB/CD137, OX-40/CD134, and CD27), immunosuppressive cytokines (e.g. IL-10, TGF-β and IL-6) and/or γC cytokines (e.g. IL-7, IL-15, and IL-21 or IL-2), IDO (indoleamine 2,3-dioxygenase) inhibitors, thalidomide and/or derivatives thereof, further immunomodulators (e.g. compounds that are known to deplete immunosuppressive Tregs and/or MDSCs), standard of care treatment, e.g. chemotherapy, radiotherapy, surgery, IFN-α conditioning, antiviral therapy, antibacterial therapy, UV therapy, anti-inflammatory therapy, etc. In case of the treatment or prevention of a pre-cancerous disorder or a cancer, the peptide-based vaccine may be combined with radiotherapy and/or chemotherapy such as treatment with carboplatin, paclitaxel, CarboTaxol (a combination of carboplatin, paclitaxel) and/or cisplatin. For example, the method of the invention may be part of a chemotherapy regimen wherein chemotherapy is applied once every three weeks. Preferably, a first pharmaceutical dosage unit of a pharmaceutical composition of the invention is administered 2 weeks after the second or third cycle of chemotherapy.

Method for Reconstitution

Also provided is a method for reconstituting dried, preferably lyophilized, peptides, comprising the following subsequent steps:

a) providing a vial comprising dried, preferably lyophilized, peptides;
b) thawing the peptides, preferably for about 5-30 min;
c) adding the reconstitution composition of the invention to the vial comprising the peptides, preferably without swirling the vial;
d) allowing to admix, preferably for about 0.5-5 minutes; and
e) swirling until a clear solution is obtained, preferably for about 1-3 minutes.

Preferably, steps b) to e) are performed at room temperature.

Further provided is a method for preparing a pharmaceutical composition, comprising the subsequent steps of:

(i) collect reconstituted peptides obtainable by the method for reconstituting dried peptides as defined above in a first syringe;
(ii) connect the first syringe of step (i) to a second syringe comprising the oil-based adjuvant using a connector;
(iii) push the content of the first syringe into the second syringe and backwards
(iv) repeat step (iii) about 10-50 times in a total in about 10-50 seconds.

Preferably, steps (i) to (iv) are performed at room temperature.

The clear solution obtained in step e) in the method for reconstituting dried peptides is to be understood herein as a reconstitution composition comprising reconstituted peptides, which can be used as starting material, i.e. as "reconstituted peptides" in step (i) of a method for preparing a pharmaceutical composition.

Preferably, the dried, preferably lyophilized, peptides in the vial and used as starting material in step a) in the method for reconstituting dried peptides, are peptides as defined herein above as peptides to be reconstituted and/or peptide to be comprised in the pharmaceutical composition of the invention. Preferably, said vial comprises peptides in an amount for injection as a single volume in a method for prevention and/or treatment, preferably a method of treatment and/or prevention as defined herein, i.e. a single pharmaceutical dosage unit, or part thereof in case of multiple injections at difference locations of the subjects body at substantially the same time point. Alternatively, the amount of dried peptides in the vial in step a) is exceeding the amount for injection as a single volume in said method. For instance, the amount of peptides within the vial may be twice the amount for injection as a single volume. In the latter case, half of the amount of reconstituted volume may be admixed with an amount of oil-based adjuvant in a method for preparing a pharmaceutical composition such as the pharmaceutical composition of the invention, in order to end up with a single volume of pharmaceutical composition for injection in a method or treatment or prevention, or, alternatively, the total amount of reconstituted volume may be admixed with an amount of oil-based adjuvant in order to end up with two volumes of pharmaceutical composition for injection.

Preferably, the peptides in step b) of the method to reconstitute peptides, are thawed at room temperature for about 5-30 min, or 10-30 min, such as for 5, 10, 15, 20, 25 or 30 minutes, or any value in between.

Preferably, the admixing in step d) of the method to reconstitute peptides, is without substantially swirling or stirring the vial preferably for about 0.5-2 minutes at room temperature, such as for 0.5, 1, 1.5 or 2 minutes. In other words, preferably the peptides in step d) is allowed to admix with the reconstitution composition while standing still.

The swirling in step e) of the method to reconstitute peptides, is performed by swirling until a clear solution is obtained. As indicated, this is performed preferably for about 1-3 minutes. However, for some peptides longer or shorter swirling time is required. However, a clear solution should preferably be obtainable within 20 minutes. Therefore, the swirling may be performed in a range from 1 to 20 min, from 1 to 10 min, from 1 to 5 minutes or from 1 to 3 minutes, such as 1, 2, 3, 4, 5, 6, 7, 8, 9, 10, 15 or 20 minutes, or any value in between, preferably until a clear solution is obtained upon visual inspection.

The reconstitution composition of step c) of the method for reconstituting peptides, and the oil-based adjuvant of step (ii) of the method for preparing a pharmaceutical composition, are as defined earlier herein. Preferably, the amount of reconstitution composition in step c) is in a range of from about 0.5 and 2 mL, preferably 1 mL. Preferably, the amount of reconstituted peptides in step (i) is the total amount of reconstituted peptides as obtained after step e), i.e. within the clear solution obtained after step e). However, optionally less is used, as exemplified above. Preferably, the volume of this reconstitution composition is admixed with oil-based adjuvant in step (ii) to (iv) in a ratio of about 2:1 to about 1:2, such as 2:1, 1.9:1, 1.8:1, 1.7:1, 1.6:1, 1.5:1, 1.4:1, 1.1:1, 1:1, 1:1.9, 1:1.8, 1:1.7, 1:1.6, 1:1.5, 1:1.4, 1:1.3, 1:1.2, or 1:1.1, preferably 1:1 of reconstitution composition: oil-based adjuvant.

The connector in (ii) may be any connector suitable in the art to connect two syringes that allow fluids to be exchanged between the two syringes, such as but not limited to, T and I connectors. The repeats (iv) may be about 10-50 times, such as, but are not limited to, 10, 15, 20, 25, 30, 45, 50 times, or any value in between.

Kit of Parts

Further, provided is a kit of parts comprising a:
1. a first vial containing dried, preferably lyophilized, peptides, wherein preferably the peptides are peptides as defined herein above;
2. a second vial containing a reconstitution composition of the invention; and, optionally,
3. a third vial containing an oil-based adjuvant, preferably as defined herein above.

Preferably, the all components, i.e. dried peptides, reconstitution composition and oil-based adjuvant, are sterile and/or pharmaceutical-grade or clinical-grade. Preferably, these components are manufactured using Good manufacturing practice (GMP) and have GMP quality as defined by both the European Medicines Agency and the Food and Drug Administration.

Preferably, the first vial is stored at a temperature at which the reconstitution composition is stable for at least 1 month, 2 months, 3 months, 6 months or 1 year or even 2 years. Preferably, said temperature is between $-25°$ C. and $25°$ C., or between $-23°$ C. and $-18°$ C., or between $0°$ C. and $10°$ C., or between $2°$ C. and $8°$ C., or between $18°$ C. and $23°$ C. Preferably, the second vial is stored at a temperature at which the reconstitution composition is stable for at least 1 month, 2 months, 3 months, 6 months or 1 year or even 2 years. Preferably, said temperature is between $-25°$ C. and $25°$ C., or between $-23°$ C. and $-18°$ C., or between $0°$ C. and $10°$ C., or between $2°$ C. and $8°$ C., or between $18°$ C. and $23°$ C. . . . Preferably, the third vial is stored at a temperature at which the reconstitution composition is stable for at least 1 month, 2 months, 3 months, 6 months or 1 year or even 2 years. Preferably, said temperature is between $-25°$ C. and $25°$ C., or between $-23°$ C. and $-18°$ C., or between $0°$ C. and $10°$ C., or between $2°$ C. and $8°$ C., or between $18°$ C. and $23°$ C. Preferably, the first, second and third vial are stored at the same temperature.

Optionally, said kit of parts further comprises a manual describing the method for reconstituting dried peptides as defined herein above, storage conditions, a method for preparing a pharmaceutical composition as defined herein above and/or a manual for storing the first, second and/or third vial. In addition, the kit of parts may comprise a manual for administering the pharmaceutical composition to be prepared. Preferably, the volume of the first, second and/or third vial is at most 50 mL, preferably between 0.1 and 10 mL, preferably between 1 and 10 mL, such as, 0.5, 1, 2, 3, 4, 5 or 10 mL, or any value in between. A vial is to be understood herein as a container that can have any shape. Optionally a vial is to be understood herein as a syringe. Optionally, the first vial can be connected via a connector by an active handling process to the second vial to allow the reconstitution composition to contact and dissolute the peptides. Optionally, the second vial can subsequently be connected to the third vial to allow the reconstitution composition comprising the peptides to be admixed with the oil-based adjuvant. Optionally, the kit of parts further comprises one or more connectors, such as a T-connector, and/or an injection unit, such as a needle. Preferably, the amount of peptides in the first file, the amount of reconstitution composition in the second file and/or the amount or oil-based adjuvant in the third file are as defined in the method for reconstituting peptides and/or the method for preparing a pharmaceutical composition as defined earlier herein.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

The word "about" or "approximately" when used in association with a numerical value (e.g. about 10) preferably means that the value may be the given value (of 10) more or less 0.1% of the value.

The sequence information as provided herein should not be so narrowly construed as to require inclusion of erroneously identified bases. The skilled person is capable of identifying such erroneously identified bases and knows how to correct for such errors.

All patent and literature references cited in the present specification are hereby incorporated by reference in their entirety.

LEGENDS TO THE FIGURES

Figure 1B:
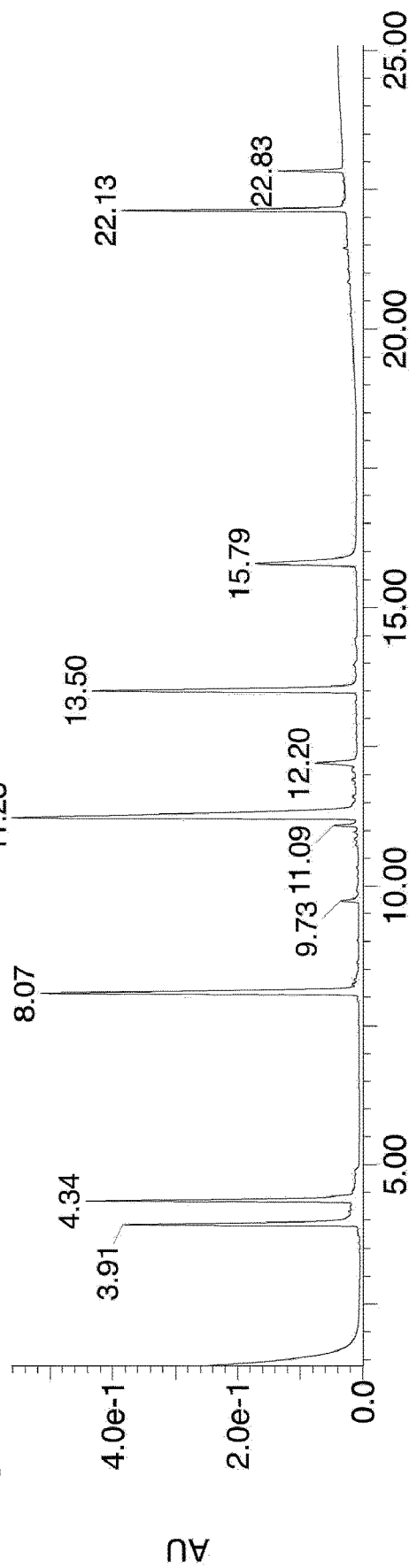
Figure 1C:
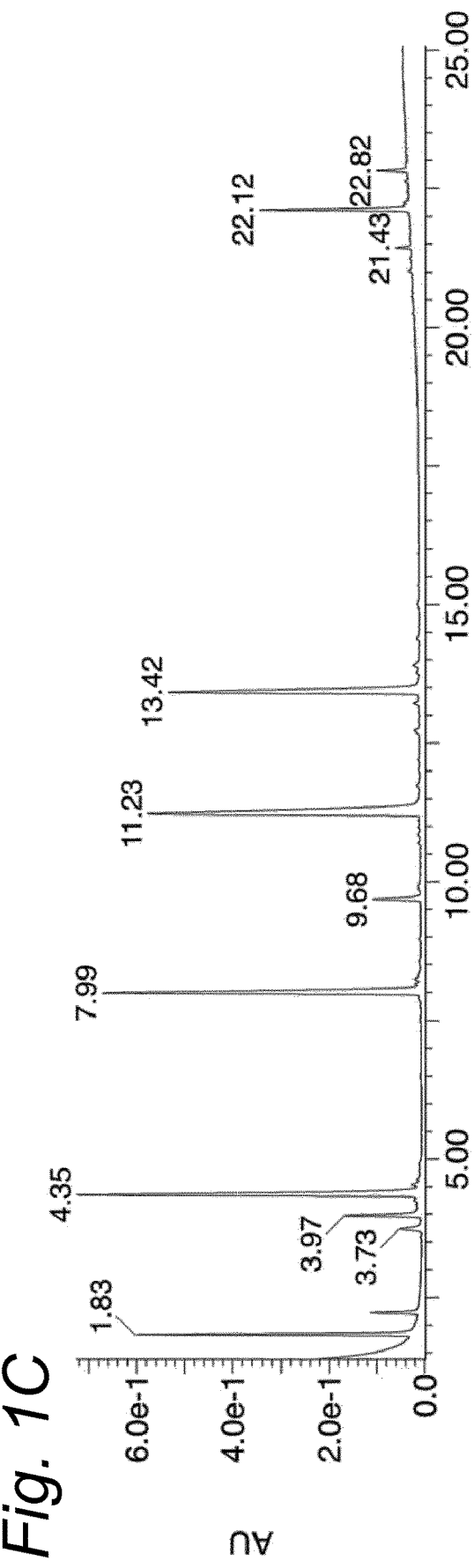
Figure 2A:
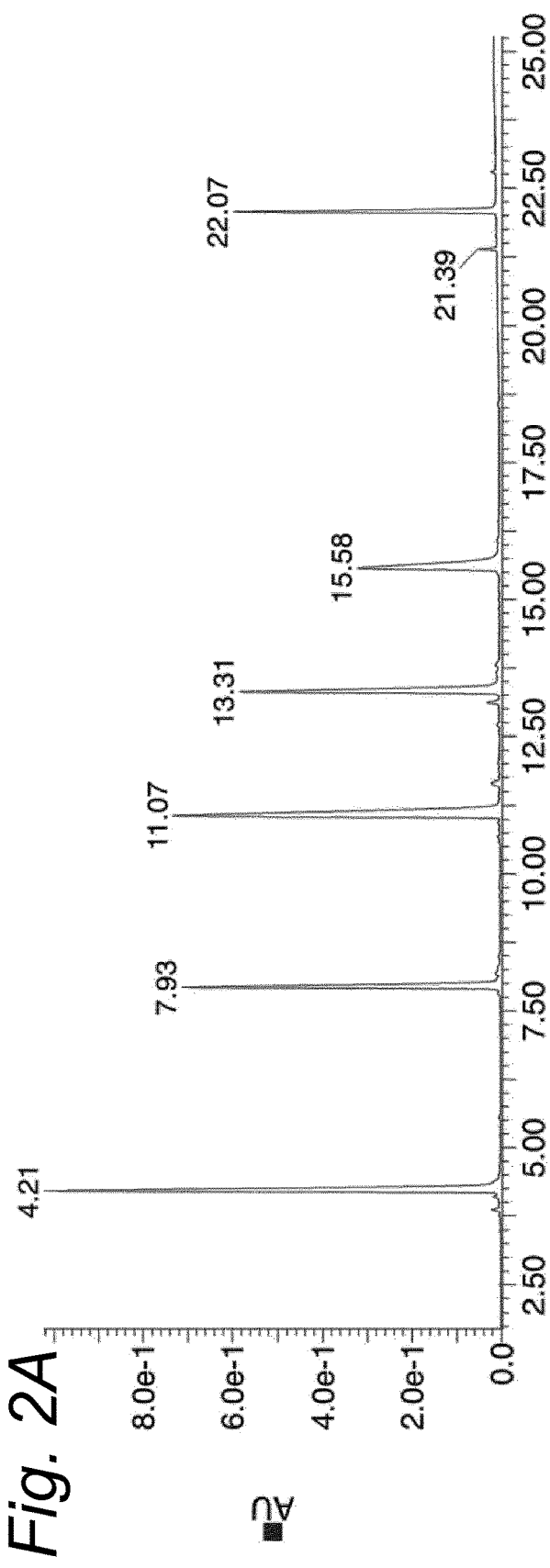
Figure 2B:
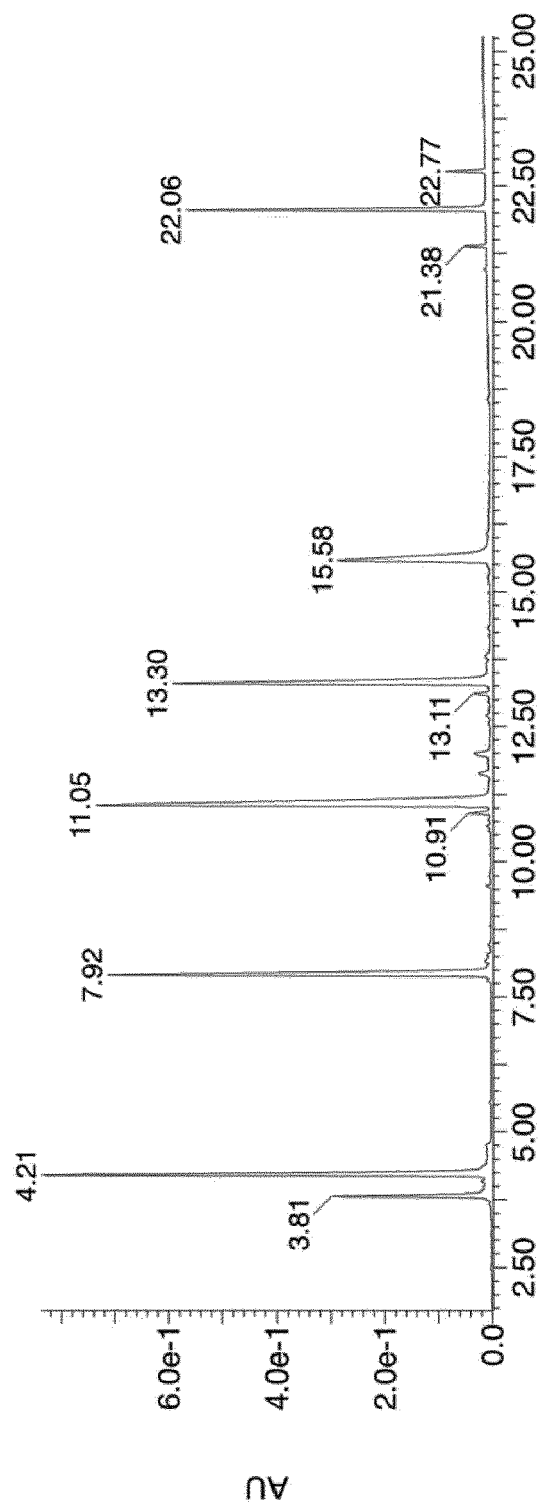
Figure 2C:
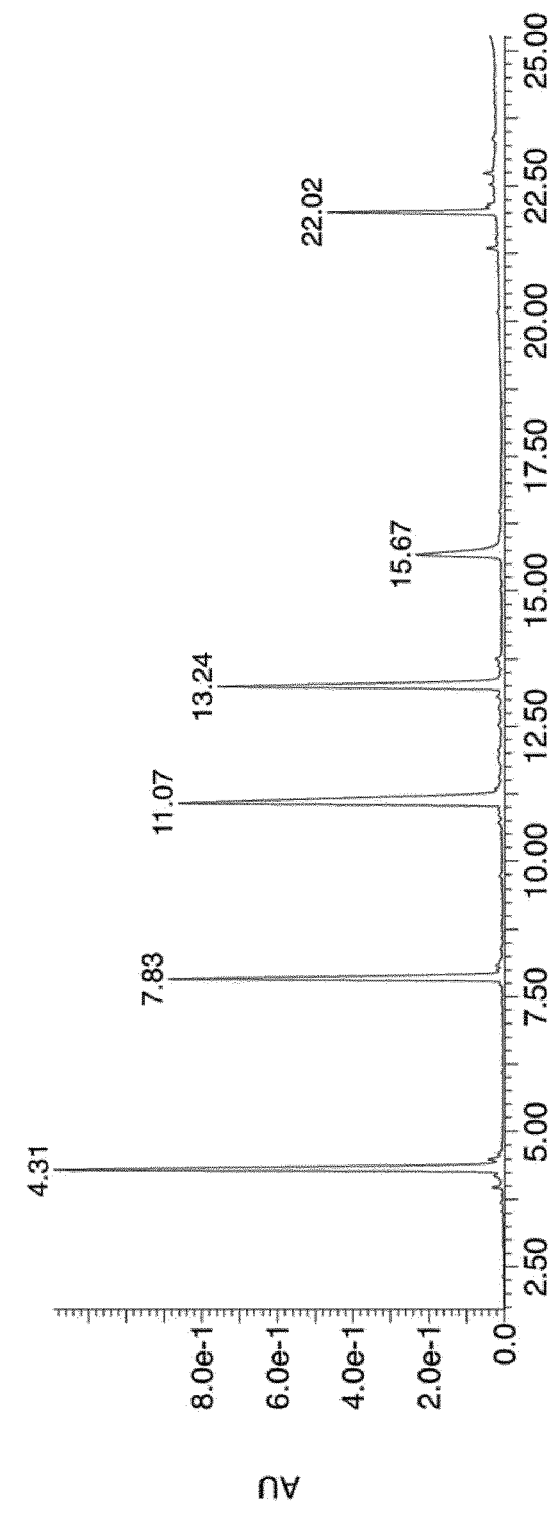
Figure 2D:
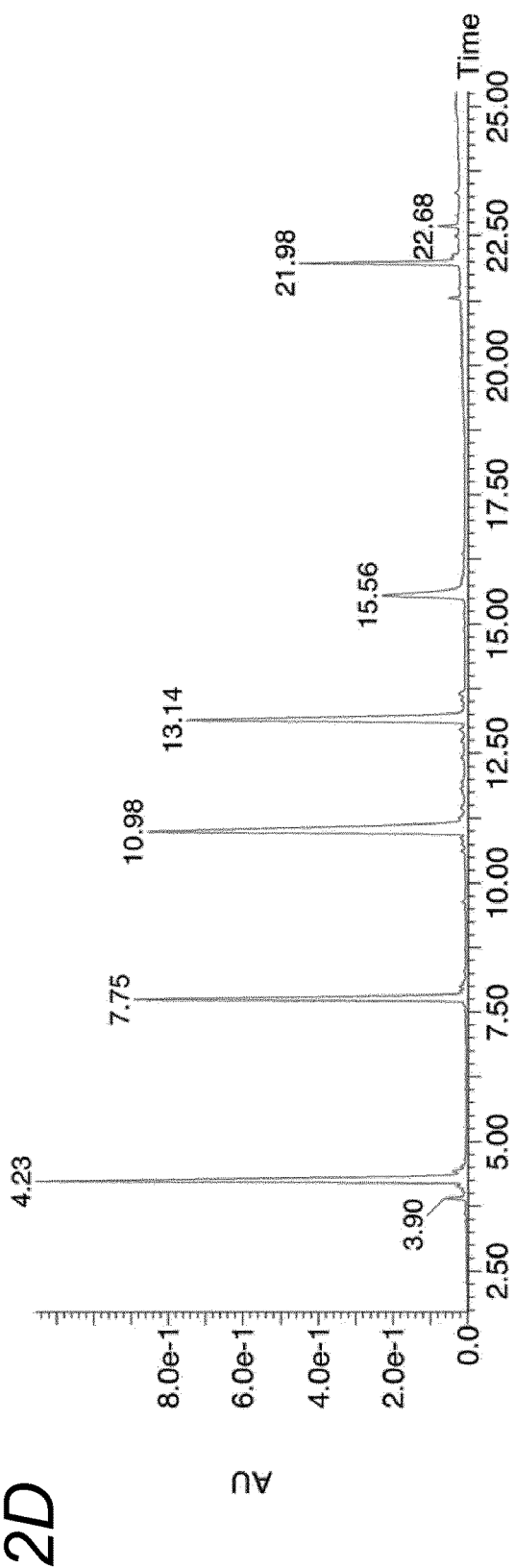
Figure 3A:
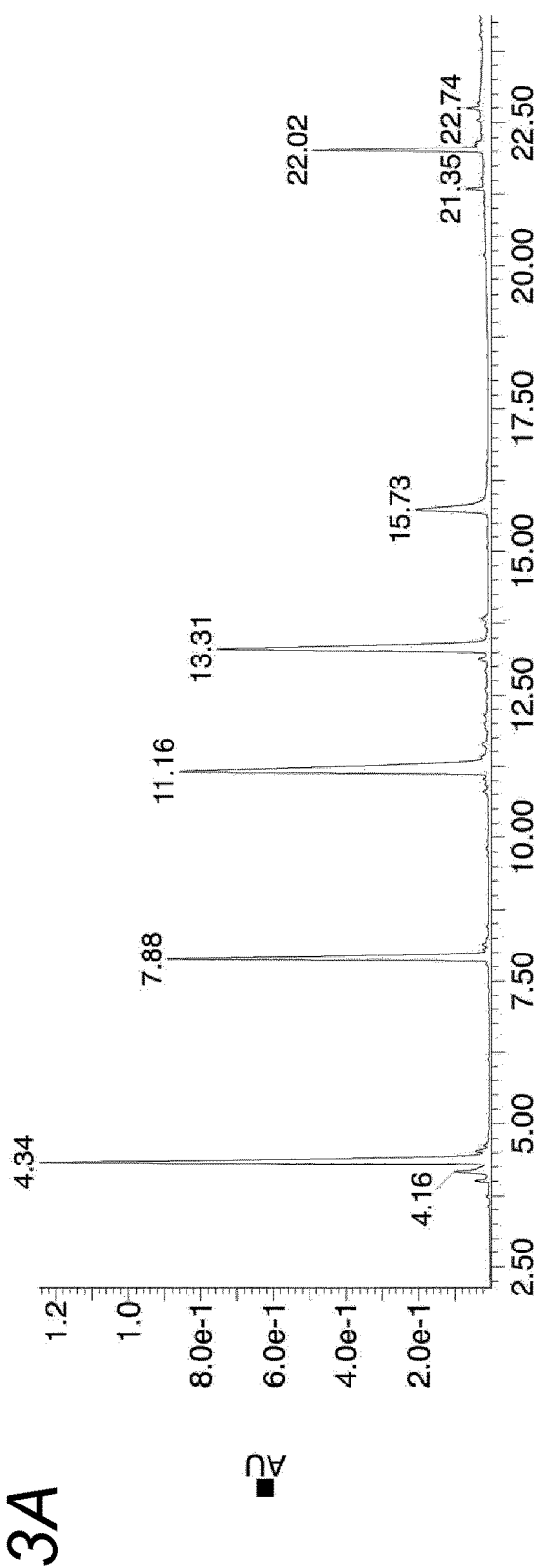
Figure 3B:
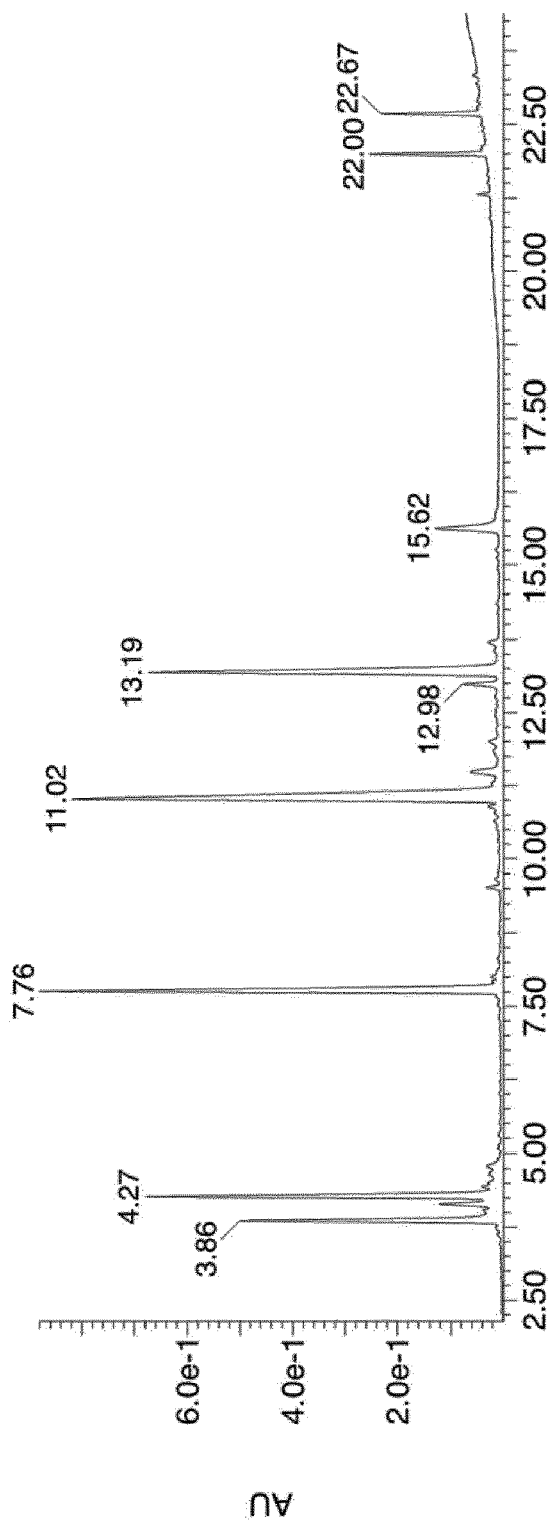
Figure 3C:
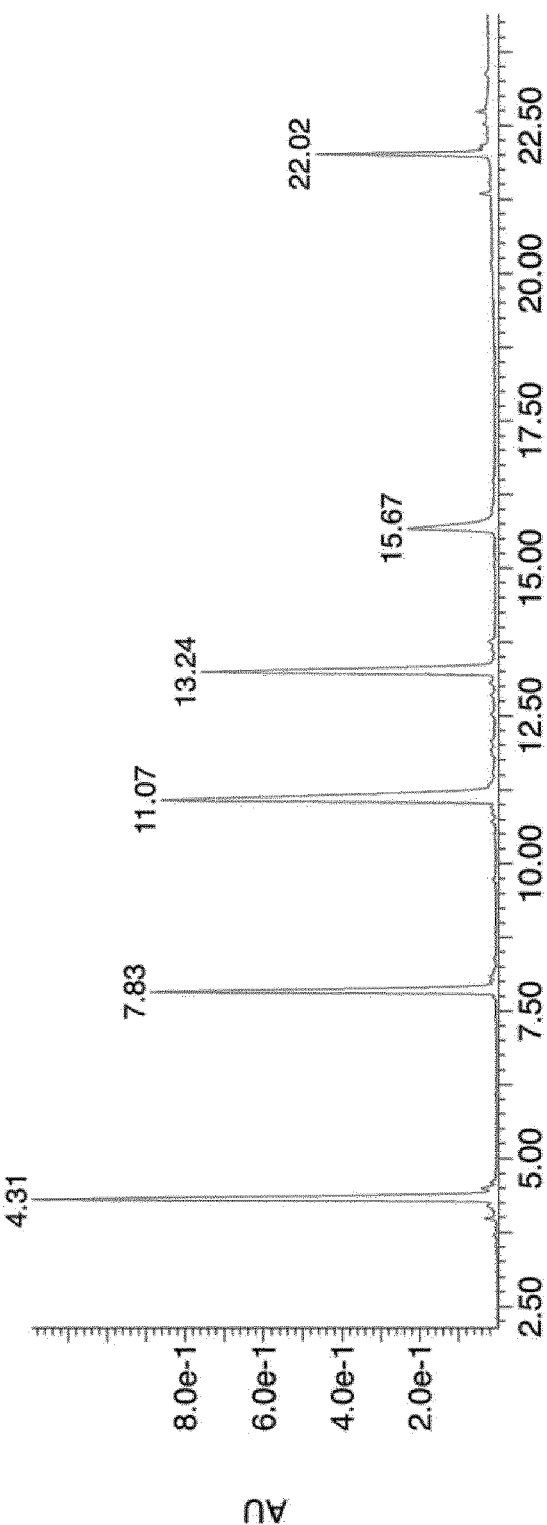
Figure 3D:
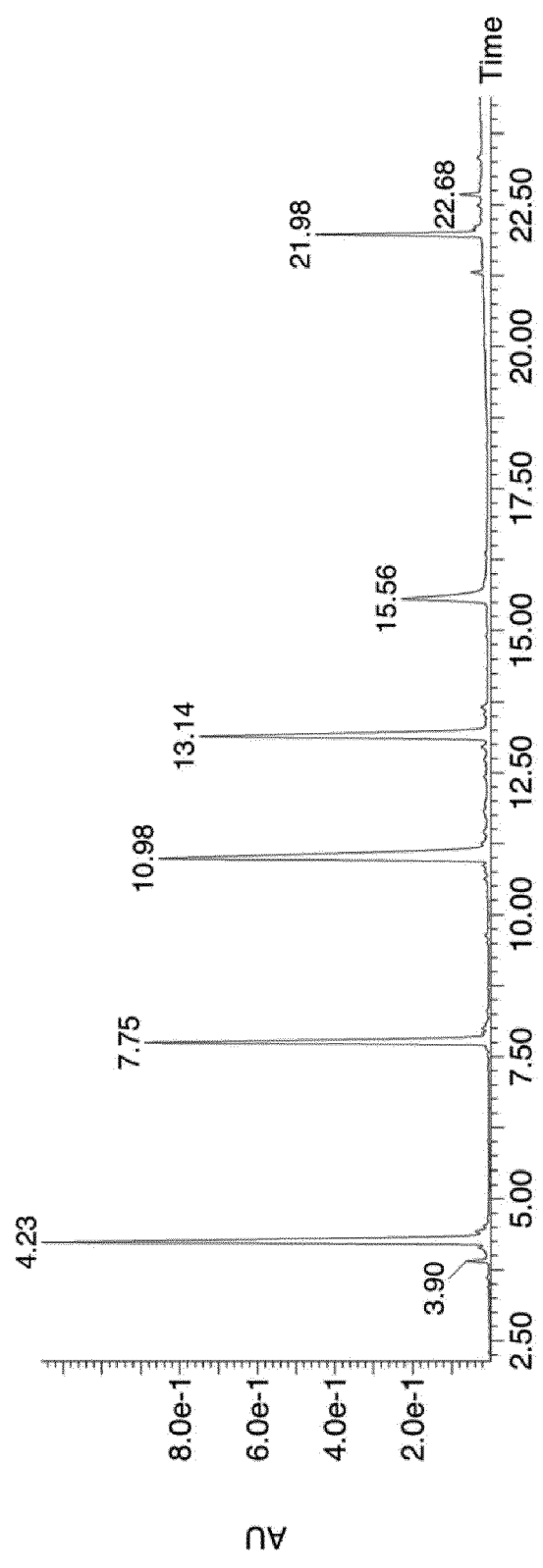
Figure 4A:
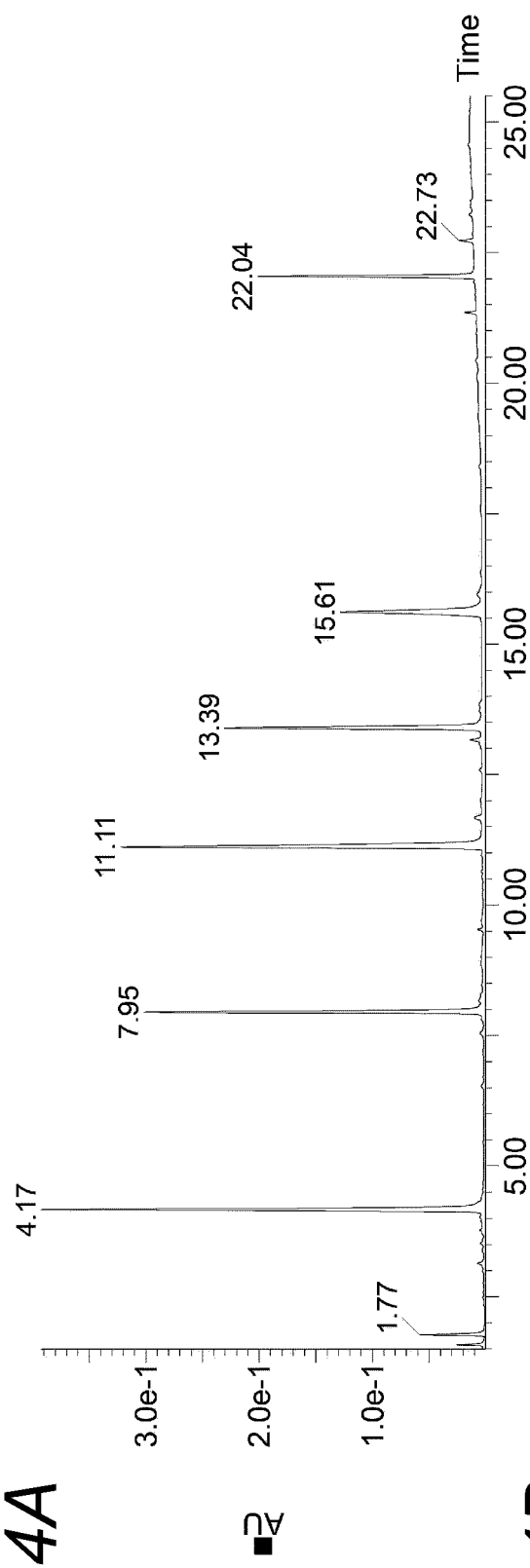
Figure 4B:
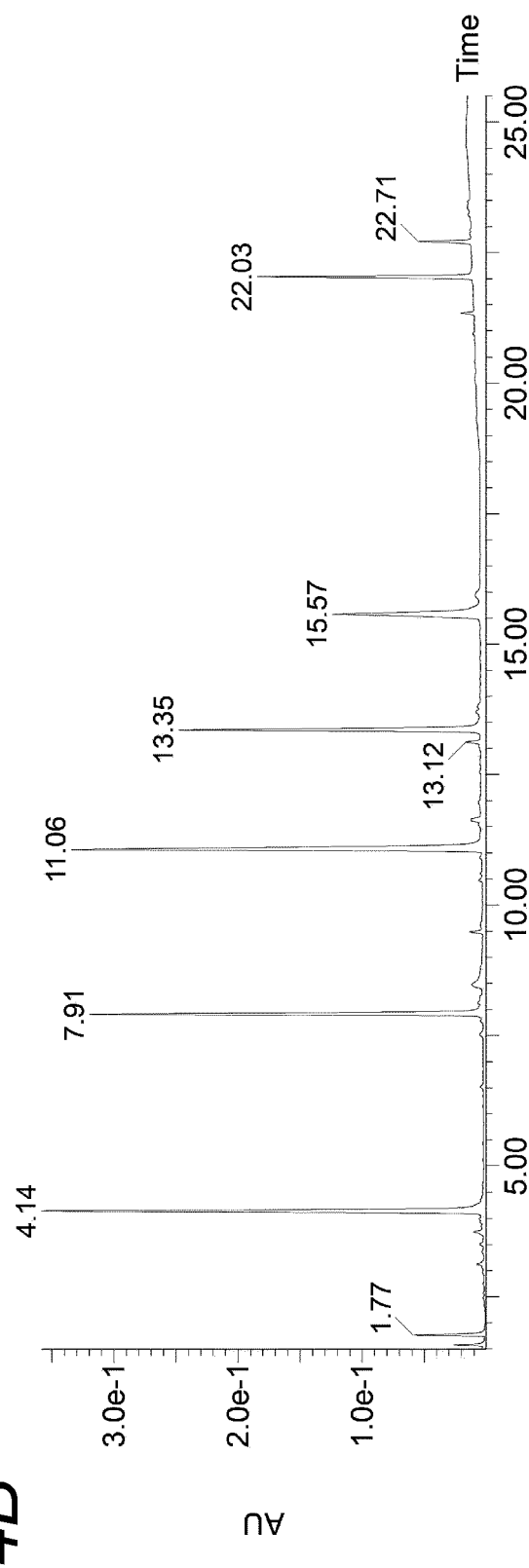
Figure 4C:
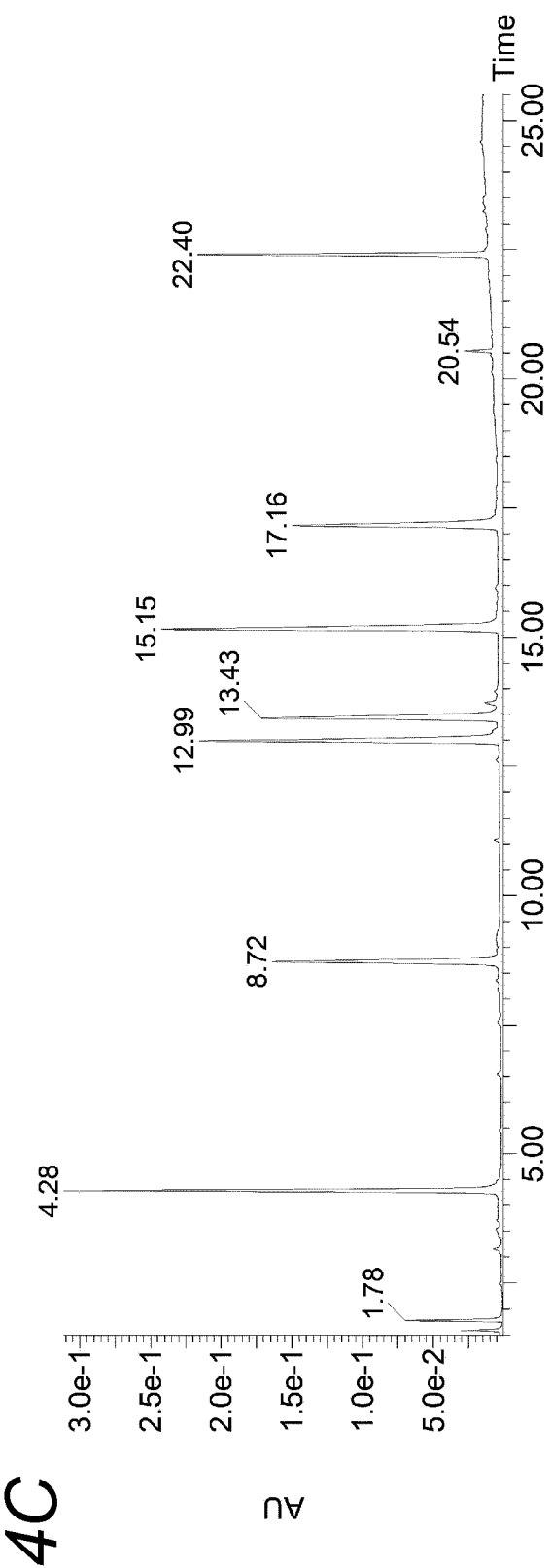
Figure 4D:
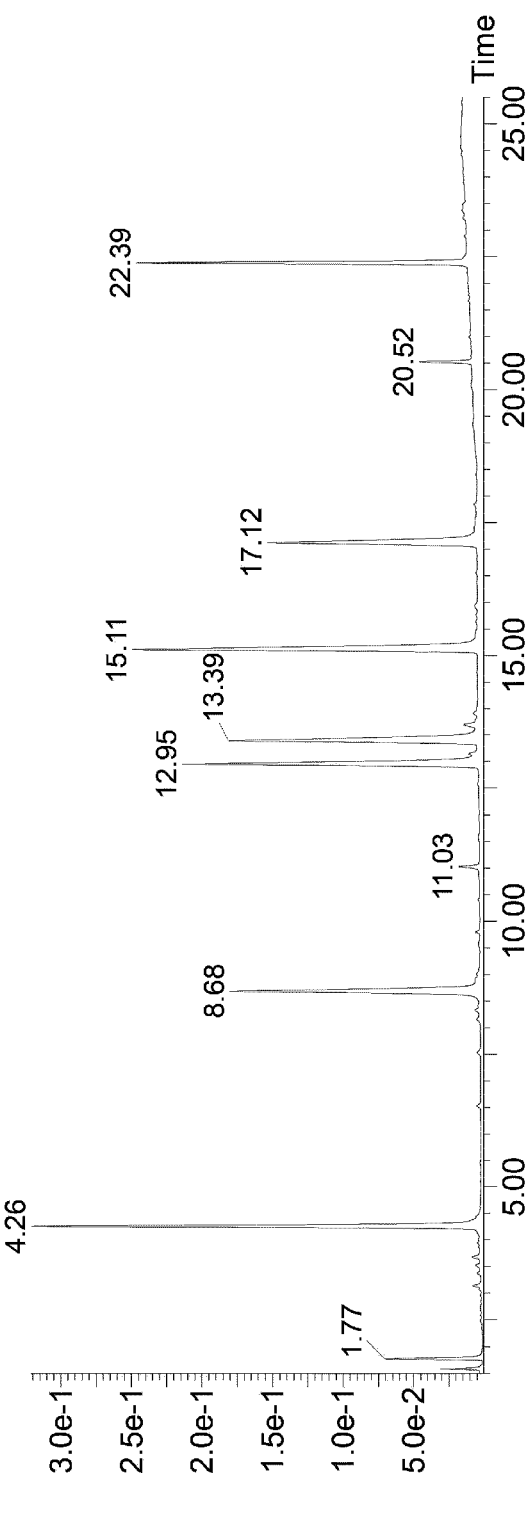

FIG. 1: UPLC chromatograms of DP-6P (comprising SLPs represented by SEQ ID NOs: 1-6) in three different solvent mixtures, two hours after dissolution and storage at room temperature. A) DP-6P (2.40 mg total peptide) dissolved in a mixture of 750 µL 0.1M Citric acid in water, 62.5 µL Propylene Glycol, 125 µL Ethanol and 62.5 µL Cremophor EL; B) DP-6P (2.40 mg total peptide) dissolved in 20% v/v DMSO/water; C) DP-6P (2.40 mg total peptide) dissolved in 20% v/v DMSO/water with 10 mM DTT.

FIG. 2: UPLC chromatograms of DP-6P (comprising SLPs represented by SEQ ID NOs: 1-6) in two different solvent mixtures and at two time points after dissolution (t=0 and t=2 h). Both solvent mixtures contain Propylene Glycol, Ethanol, water and stabilizing or reducing agents. A) DP-6P (2.40 mg total peptide) dissolved in a mixture of 600 µL water, 267 µL Propylene Glycol, 133 µL Ethanol and 1 mg/mL Ascorbic acid at t=0 B) DP-6P (2.40 mg total peptide) dissolved in a mixture of 600 µL WFI, 267 µL Propylene Glycol, 133 µL Ethanol and 1 mg/mL Ascorbic acid at t=2 h; C) DP-6P (2.40 mg total peptide) dissolved in a mixture of 750 µL 0.1M Citric acid in water, 62.5 µL Propylene Glycol, 125 µL Ethanol and 62.5 µL Cremophor EL at t=0; D) DP-6P (2.40 mg total peptide) dissolved in a mixture of 750 µL 0.1M Citric acid in water, 62.5 µL Propylene Glycol, 125 µL Ethanol and 62.5 µL Cremophor EL at t=2 h.

FIG. 3: UPLC chromatograms of DP-6P (comprising SLPs represented by SEQ ID NOs: 1-6) in two different solvent mixtures. All solvent mixtures contain per mL 750 µL 0.1M Citric acid in water, 62.5 µL Propylene Glycol, 125 µL Ethanol and either Tween20 or Cremophor EL (62.5 µL). A) DP-6P (2.40 mg total peptide) dissolved in the solvent mixture comprising Tween20 at t=0; B) DP-6P (2.40 mg total peptide) dissolved in the solvent mixture comprising Tween20 at t=2 h; C) DP-6P (2.40 mg total peptide) dissolved in the solvent mixture comprising Cremophor EL at t=0; D) DP-6P (2.40 mg total peptide) dissolved in the solvent mixture comprising Cremophor EL at t=2 h.

FIG. 4: UPLC chromatograms of DP-6P (comprising SLPs represented by SEQ ID NOs: 1-6) and DP-7P (comprising SLPs represented by SEQ ID NOs: 7-13) after reconstitution and emulsification with Montanide ISA 51 VG. The solvent mixture for reconstitution contains per mL 750 µL 0.1M Citric acid in water, 62.5 µL Propylene Glycol, 125 µL Ethanol and Cremophor EL (62.5 µL). Prior to analysis, peptides were extracted from the emulsion by adding an excess of the solvent mixture and forcing phase separation by centrifugation. A) DP-6P (2.4 mg total peptide) dissolved in 1 mL solvent mixture comprising Cremophor EL at t=0 (immediately after vaccine preparation and extraction); B) DP-6P (2.4 mg total peptide) dissolved in 1 mL solvent mixture comprising Cremophor EL at t=2 h (after 2 hours storage of the vaccine product, followed by extraction). C) DP-7P (2.8 mg total peptide) dissolved in 1 mL solvent mixture comprising Cremophor EL at t=0 (immediately after vaccine preparation and extraction); D) DP-7P (2.8 mg total peptide) dissolved in 1 mL solvent mixture comprising Cremophor EL at t=2 h (after 2 hours storage of the vaccine product, followed by extraction).

Figure 5:
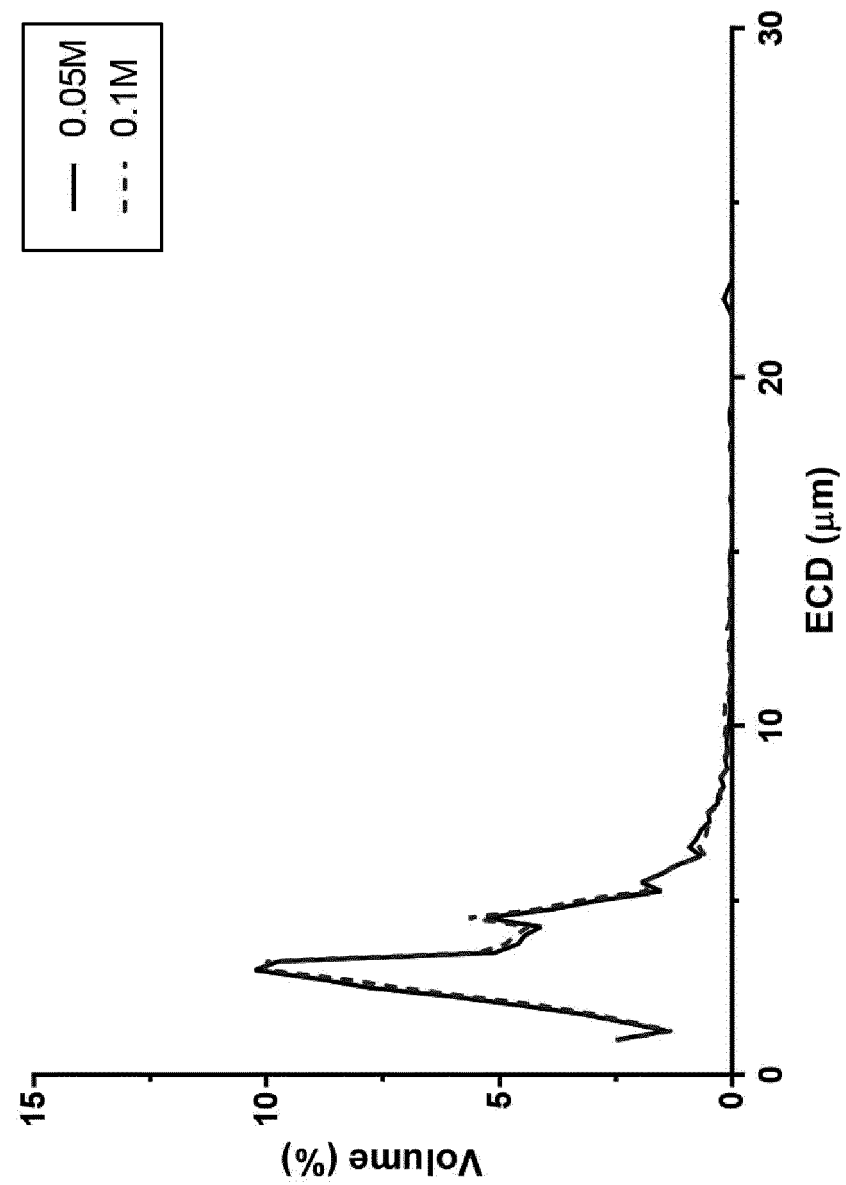

FIG. 5: Particle size distribution comparison (overlay) between DP-6P emulsions using two different citric acid concentrations. DP-6P (2.40 mg total peptide) dissolved in a mixture of 750 µL 0.05M or 0.1M Citric acid in water, 62.5 µL Propylene Glycol, 125 µL Ethanol and 62.5 µL Cremophor EL, and subsequently emulsified with 1 mL Montanide ISA51 VG.

Figure 6A:
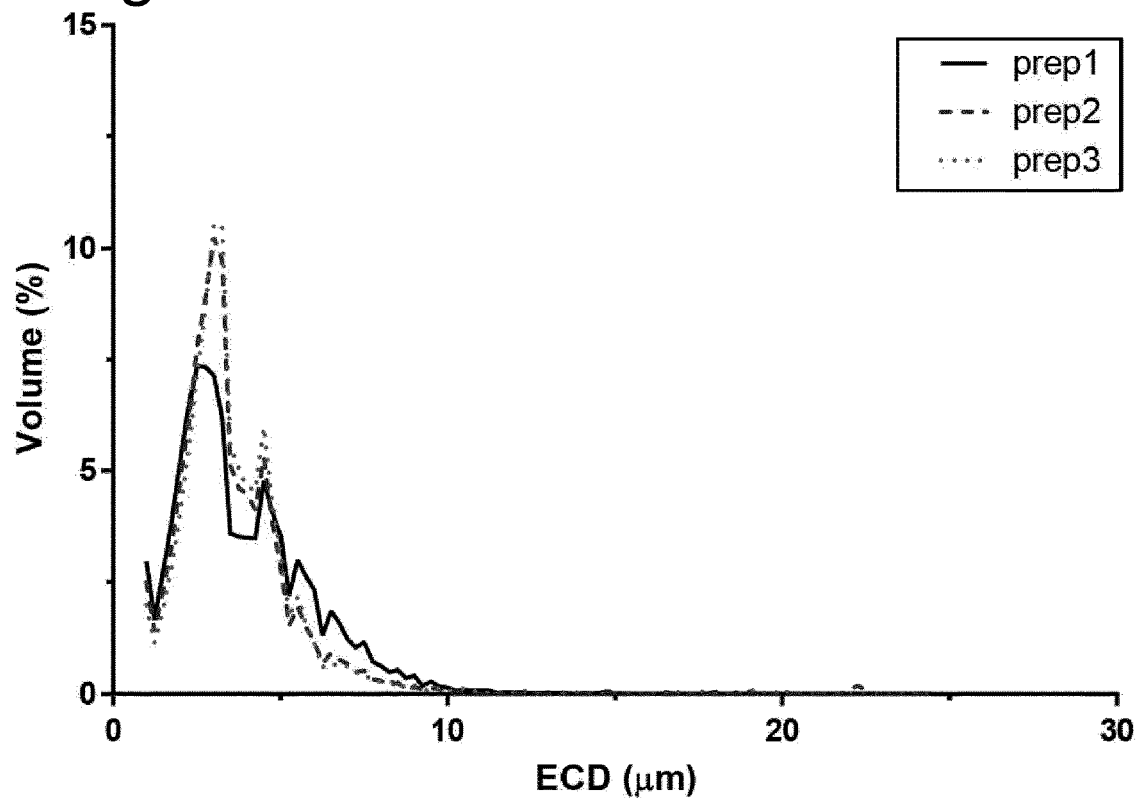
Figure 6B:
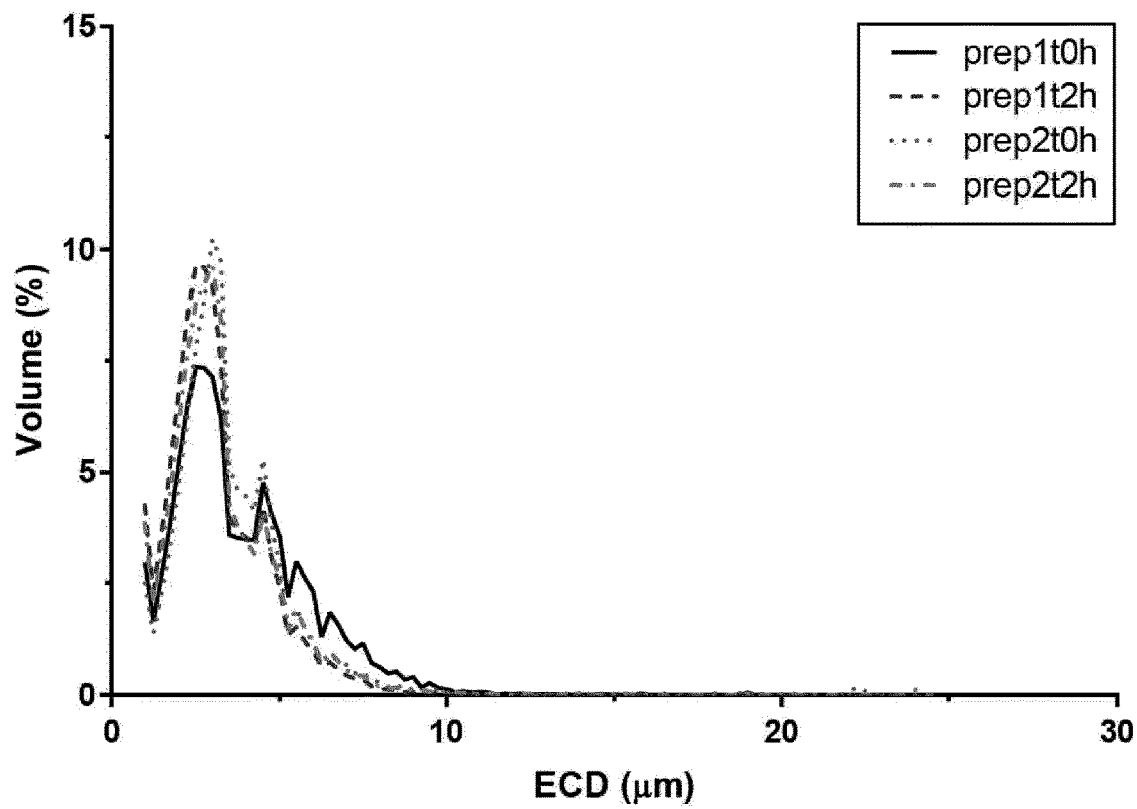

FIG. 6: Particle size distribution comparison (overlay) between DP-6P emulsions (comprising SLPs represented by SEQ ID NOs: 1-6). DP-6P (2.40 mg total peptide) was dissolved in a mixture of 750 µL 0.1M Citric acid in water, 62.5 µL Propylene Glycol, 125 µL Ethanol and 62.5 µL Cremophor EL and subsequently emulsified with 1 mL Montanide ISA51 VG. A) Three independent (repeated) preparations (prep1, prep2 and prep3) at t=0, indicating the robustness of the emulsification method. B) Two independent (repeated) preparations at t=0 (prep1t0 h and prep1t2 h) and t=2 h (prep2t0 h and prep2t2 h), demonstrating both robustness of the emulsification method as well as in-use physical stability of the emulsion for at least 2 hours at room temperature.

Figure 7:
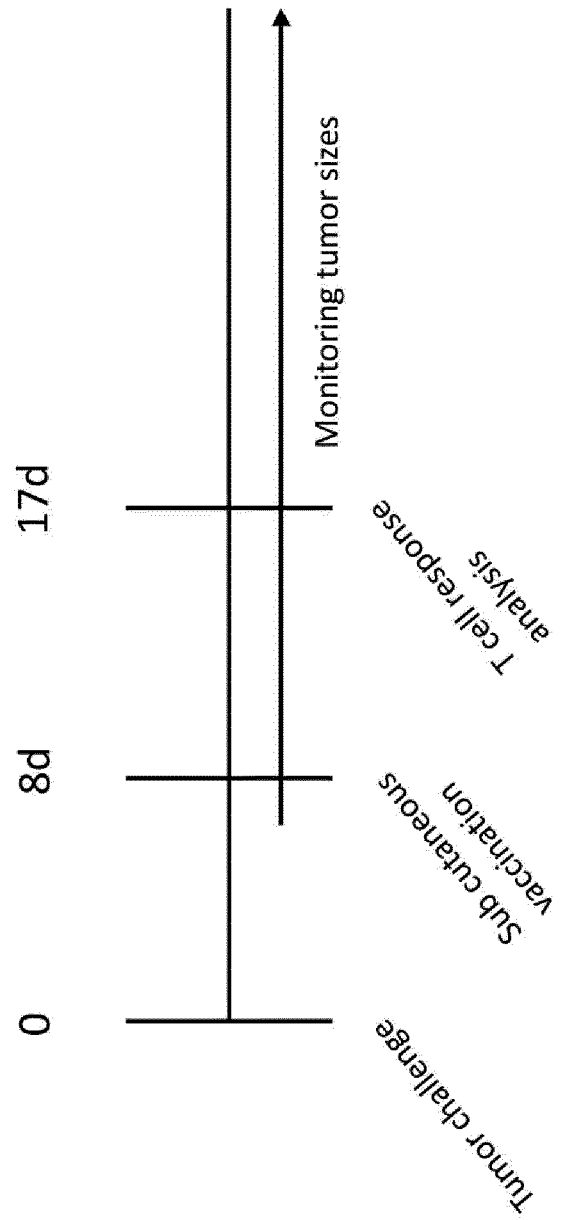
Figure 8A:
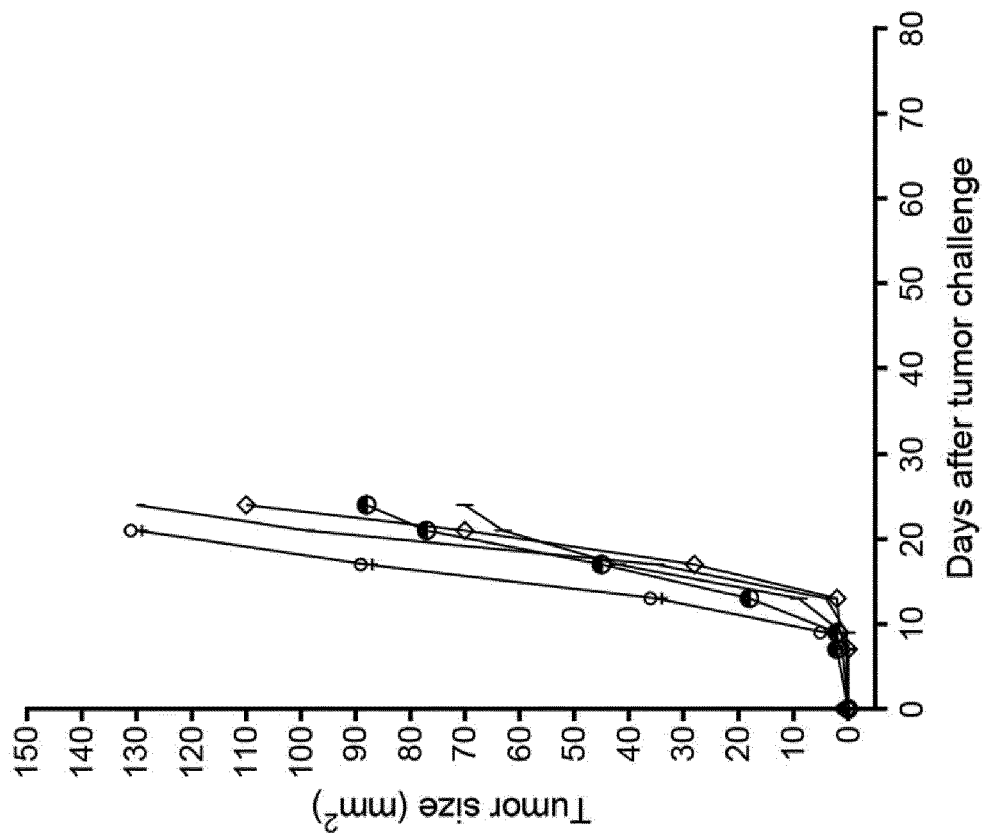
Figure 8B:
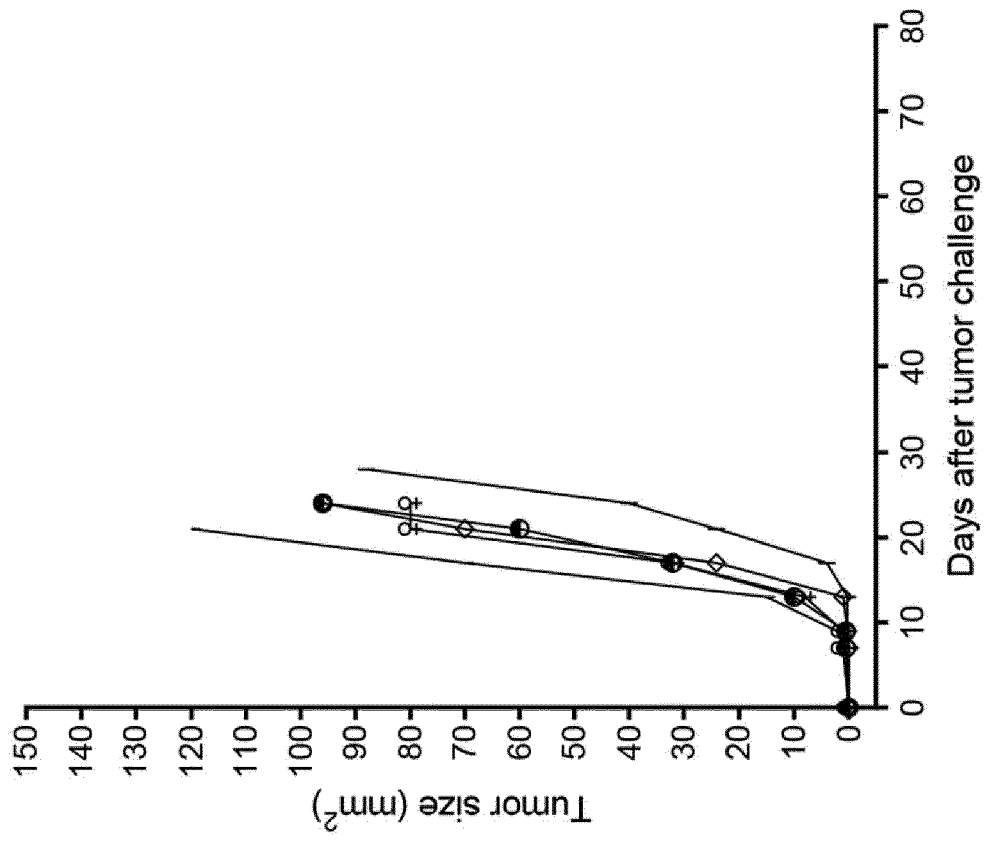
Figure 8C:
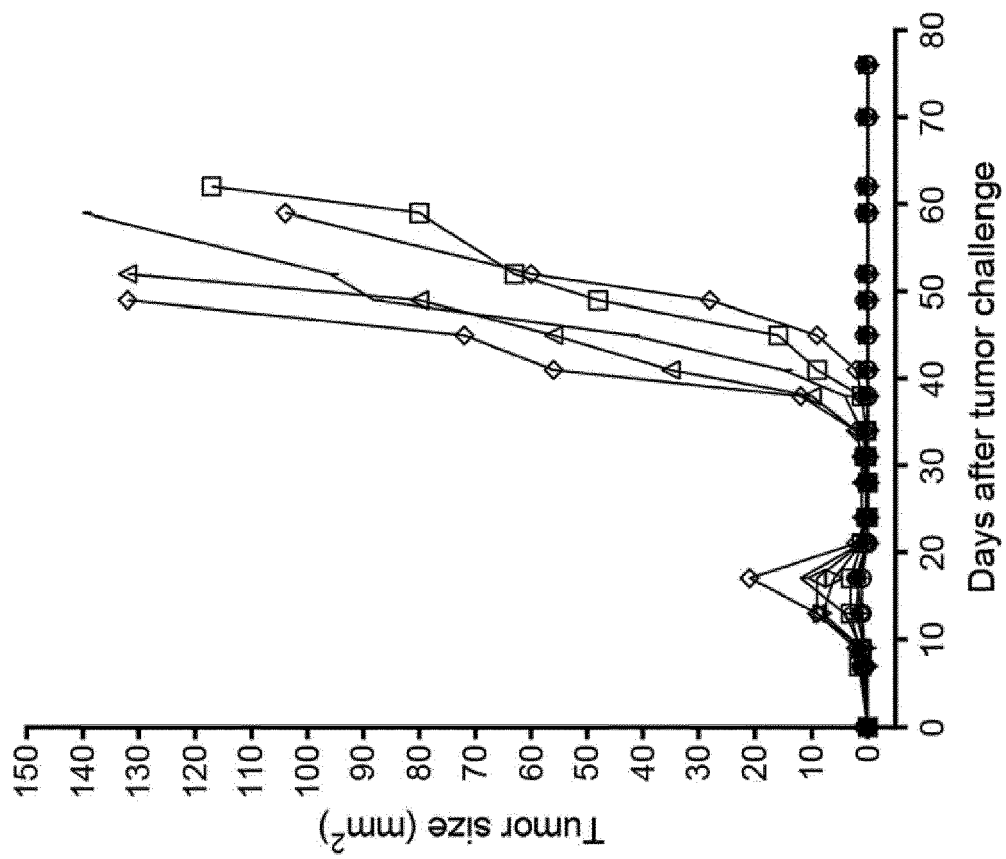
Figure 8D:
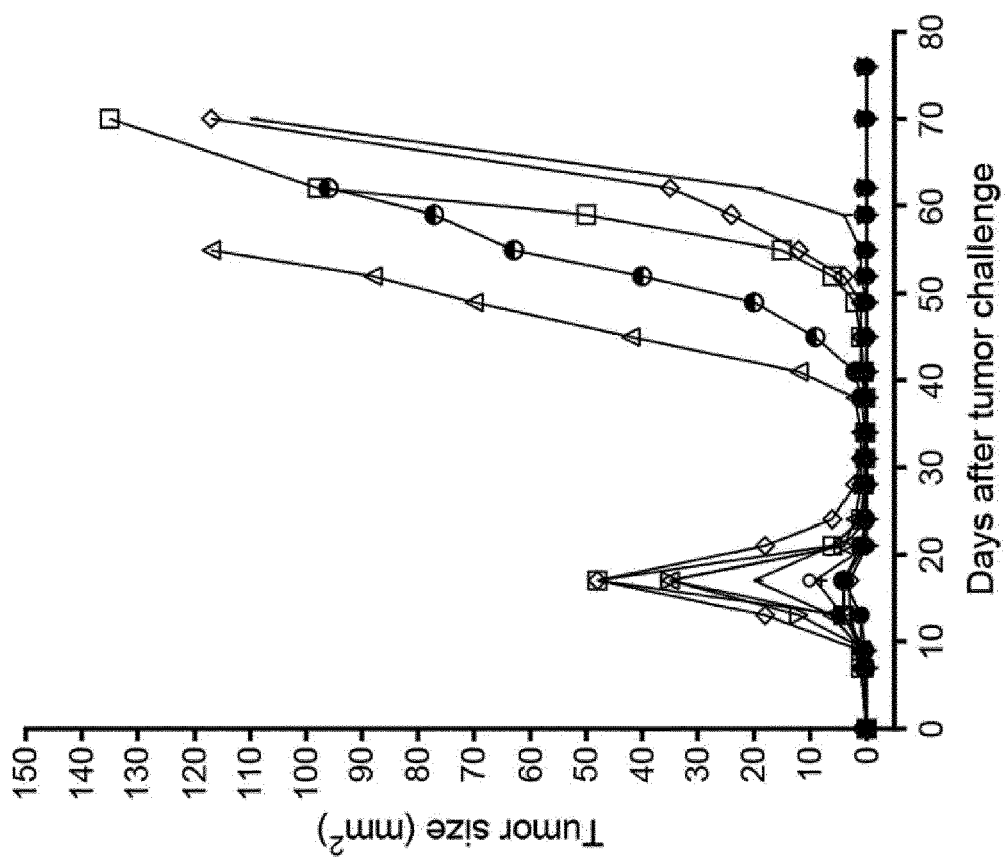

FIG. 7: Timeline for TC-1 tumor experiment.

FIG. 8: Outgrowth of TC-1 tumors in mice vaccinated with either (A) 40% v/v DMSO/WFI emulsified 1:1 with Montanide only (DMSO), (B) Reconstitution (Rec.) composition (750 µL 0.1M Citric acid in water, 62.5 µL Propylene Glycol, 125 µL Ethanol and 62.5 µL Cremophor EL) emulsified 1:1 Montanide only (Rec. composition), or with (C) SLP represented by SEQ ID NO: 6 and CpG ODN1826 dissolved in 40% v/v DMSO/WFI emulsified 1:1 with Montanide (DMSO+SLP) or (D) SLP represented by SEQ ID NO: 6 and CpG ODN1826 dissolved in Reconstitution (Rec.) composition (750 µL 0.1M Citric acid in water, 62.5 µL Propylene Glycol, 125 µL Ethanol and 62.5 µL Cremophor EL) emulsified with 1:1 Montanide (Rec. composition+ SLP).

Figure 9A:
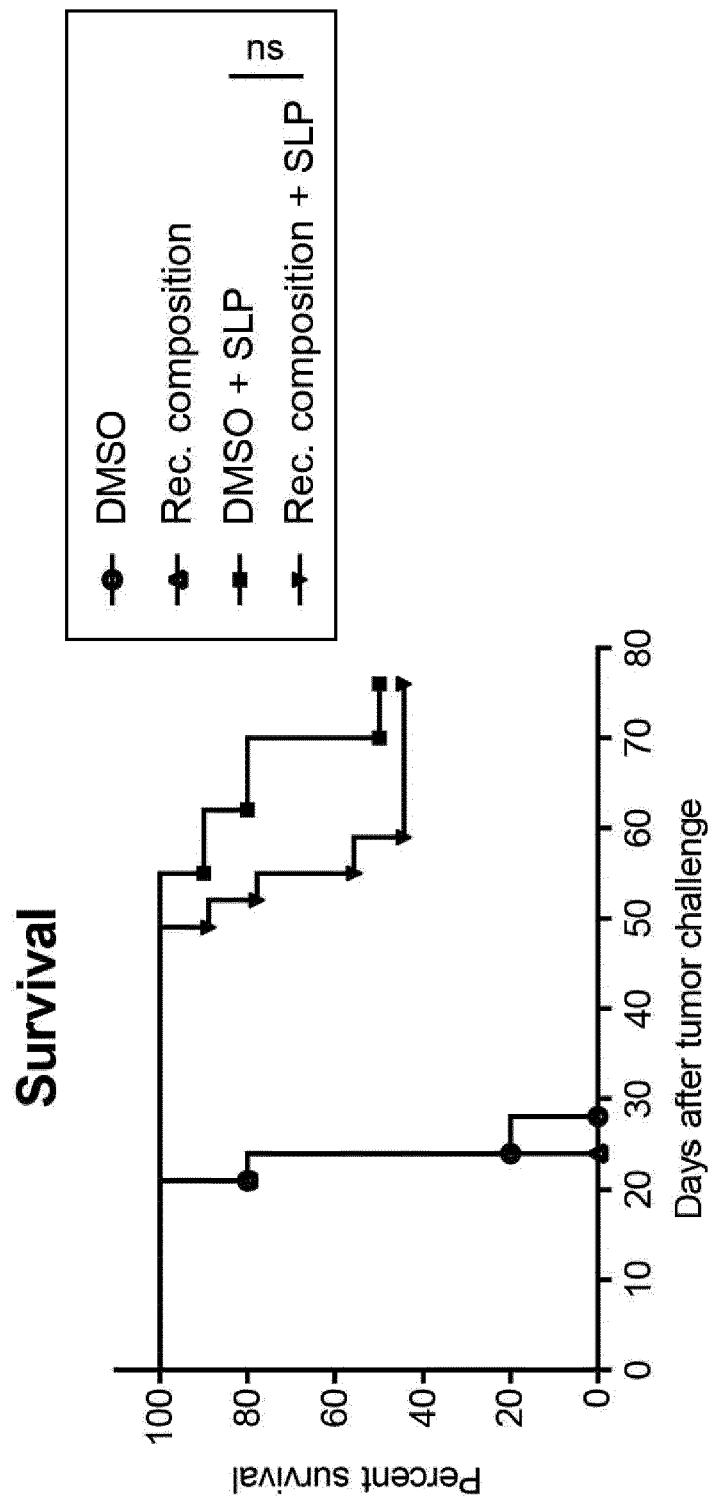

FIG. 9: Kaplan-Meier plot (survival) (A) and percentage of induced $D^b$-RAYNIVTF (tetramer) positive CD8$^+$ T cells (B) of Group 1 mice challenged with TC-1 tumors and subsequently vaccinated with 40% v/v DMSO/WFI emulsified 1:1 with Montanide only (DMSO), Group 2 mice challenged with TC-1 tumors and subsequently vaccinated with Reconstitution composition (750 µL 0.1M Citric acid in water, 62.5 µL Propylene Glycol, 125 µL Ethanol and 62.5 µL Cremophor EL) emulsified 1:1 with Montanide only (Rec. composition), Group 3 mice challenged with TC-1 tumors and subsequently vaccinated with SLP represented by SEQ ID NO: 6 and CpG ODN1826 dissolved in 40% v/v DMSO/WFI emulsified 1:1 with Montanide (DMSO+SLP)

and Group 4 mice challenged with TC-1 tumors and subsequently vaccinated with SLP represented by SEQ ID NO: 6 and CpG ODN1826 dissolved in Reconstitution composition (750 µL 0.1M Citric acid in water, 62.5 µL Propylene Glycol, 125 µL Ethanol and 62.5 µL Cremophor EL) emulsified 1:1 with Montanide (Rec. composition+SLP). Asterisk indicates significant difference (unpaired t-test, p=0.022); ns indicates non-significant difference (p=0.21).

Figure 10A:
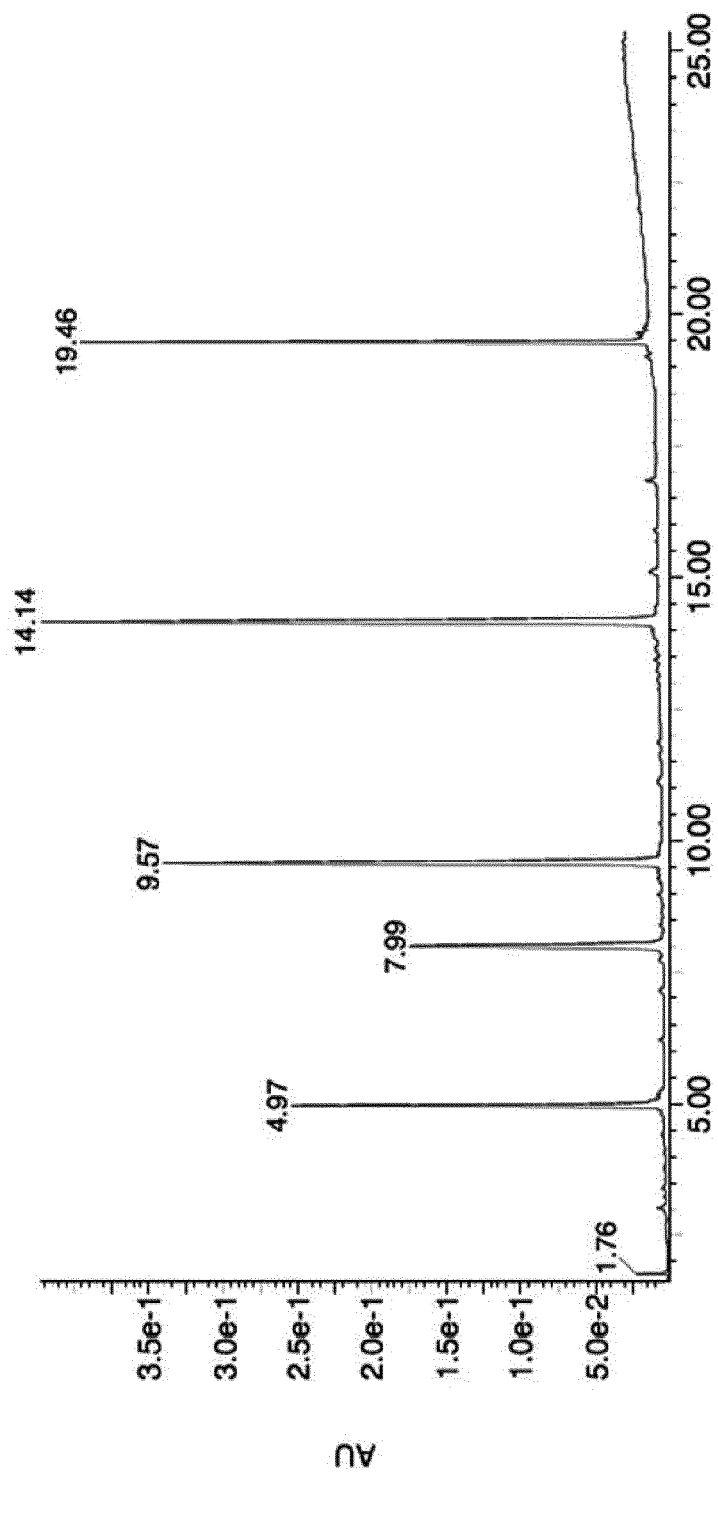
Figure 10B:
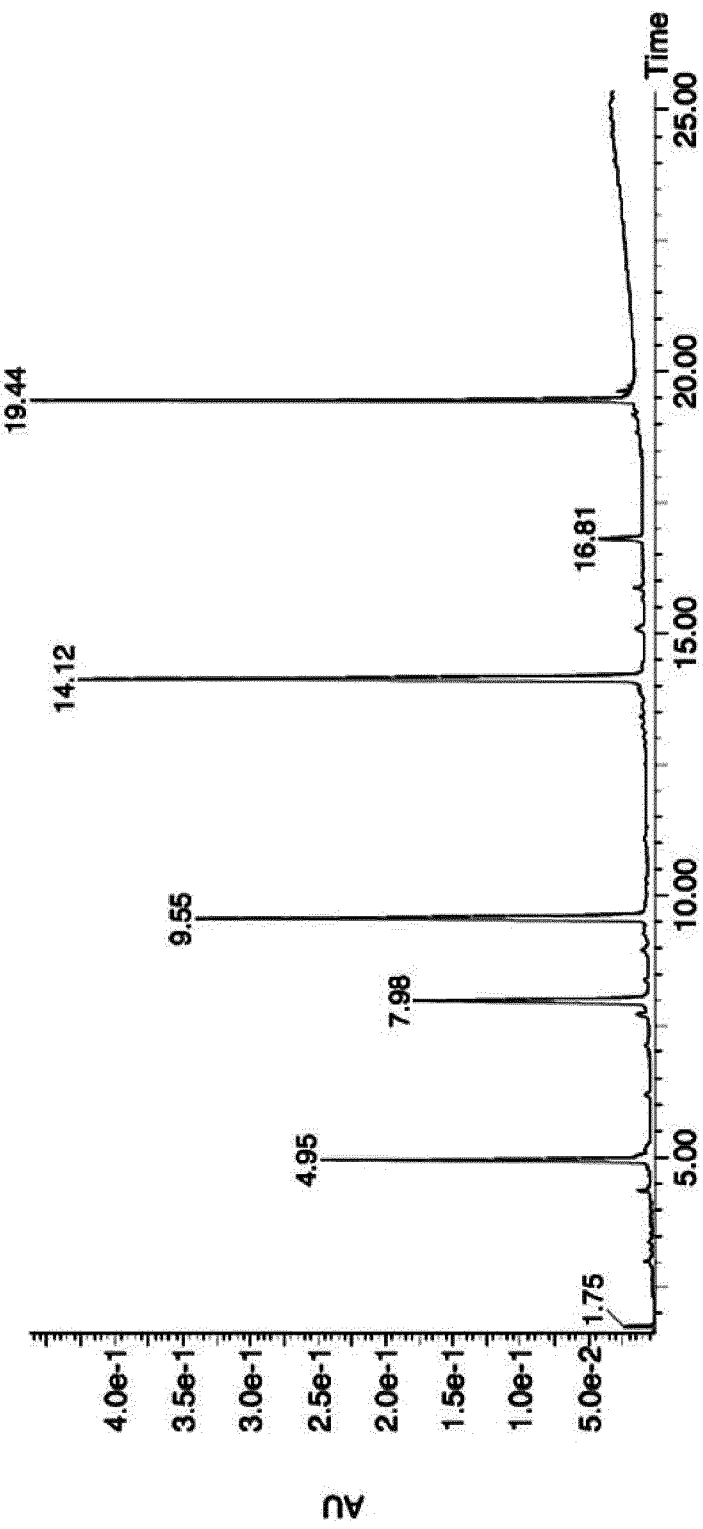

FIG. 10: UPLC chromatograms of P53 DP-5P (comprising SLPs represented by SEQ ID NO: 191, 193, 194, 201 and 203). P53 DP-5P was reconstituted with a solvent mixture containing per mL 750 µL 0.1M Citric acid in water, 62.5 µL Propylene Glycol, 125 µL Ethanol and Cremophor EL (62.5 µL). Prior to analysis, the peptides were extracted from the final product emulsion by adding an excess of the solvent mixture and forcing phase separation by centrifugation. A) P53 DP-5P (2.0 mg total peptide) dissolved in 1 mL solvent mixture comprising Cremophor EL at t=0 (immediately after vaccine preparation and extraction); B) P53 DP-5P (2.0 mg total peptide) dissolved in 1 mL solvent mixture comprising Cremophor EL at t=2 h (after 2 hours storage of the vaccine product, followed by extraction).

EXAMPLES

Example 1

Introduction

The aim of this study was to find a suitable reconstitution method for a multipeptide HPV vaccine product involving dissolution of the peptide Drug Products HPV-DP-6P and HPV-DP-7P, followed by emulsification with Montanide ISA51VG. Previous studies have shown that in DMSO/WFI formulations, peptides containing one or more cysteine residues have a strong tendency to form disulfides. To improve the chemical stability of the Drug Products and prevent disulfide formation of the peptides, a new DMSO-free reconstitution solution was developed for reconstitution of both Drug Products. This new reconstitution solution should be able to dissolve the Drug Product and result in a stable emulsion with Montanide ISA51VG. Disulfide-formation should be minimal.

The study consists of four levels of analysis:
1. Screening for a suitable solvent combination to reconstitute the Drug Products, monitoring dissolution of the peptides by visual inspection.
2. Monitoring of the emulsion stability of the Drug Product emulsion with Montanide. Stability is assessed by visual inspection and by analysis of particle size of the emulsion droplets.
3. Analysis of the chemical stability of the Drug Product after reconstitution in solvents that were successful on level 1 and 2.
4. Analysis of the chemical stability of the Drug Product after reconstitution and emulsification, using solvents that were successful in level 1, 2 and 3. For this purpose, the peptides are dissolved, emulsified with Montanide ISA 51 VG, followed by extraction from the emulsion and analysis of the peptide composition.

Materials

The following lyophilized peptide compositions were used: DP-5P comprising peptides represented herein by SEQ ID NO: 1-5 admixed at equal net weights of 0.40 mg of each peptide per vial (total amount of protein per vial being 2.00 mg) and 0.56 mg TFA per vial; DP-6P comprising peptides represented herein by SEQ ID NO: 1-6 admixed at equal net weights 0.40 mg of each peptide per vial (total amount of protein per vial being 2.40 mg) and 0.67 mg TFA per vial; and DP-7P comprising peptides represented herein by SEQ ID NO: 7-13 admixed at equal net weights of 0.40 mg of each peptide per vial (total amount of protein per vial being 2.80 mg) and 0.96 mg TFA per vial.

The following chemicals were used: Cremophor EL, (Sigma Aldrich, Kolliphor EL, C5135); Propylene Glycol or PG (≥99.5%, Sigma Aldrich, W294004) Ethanol or EtOH (Absolute, VWR Emprove® Ph Eur, BP, USP. Article #1.00986.1000); Citric acid or CA (≥99%, Sigma Aldrich C1909); MilliQ water (from EQP-063); Sterile Montanide ISA 51VG (SEPPIC, batch #14V011).

The following equipment was used: Syringe extrusion devices (Discofix-3 T-connector, B. Braun); DMSO-resistant syringes (2 mL NORM-JECT Luer Lock, Henke Sass Wolf); Waters UPLC/MS system; Malvern Mastersizer 2000; Protein Simple MFI 5200 flowcell.

Methods

Dissolution

Reconstitution composition was prepared by mixing the organic and aqueous solvents before adding them to the lyophilized Drug Product. 1 mL of various reconstitution compositions was added to the Drug Product and the mixture was allowed to stand for 5 minutes, while swirling the solution several times. Physical stability was assessed by visual inspection. Chemical stability was assessed using UPLC/MS (see below under Chemical stability of the Drug Product solution).

Emulsification with Montanide

Solvent combinations resulting in a visually clear Drug Product solution were used in emulsification experiments with Montanide ISA51 VG. Unless stated otherwise, reconstitution and emulsification was performed according to the protocol in Table 1. Where indicated, mixing of the contents of syringe A and B was performed differently. These adaptations of the procedure in Table 3 are indicated in the results section in Table 4 and Table 5.

TABLE 1

Reconstitution and emulsification of drug product (DP).

| Step | Description |
|---|---|
| 1 | At least 10 minutes and maximum 30 minutes before start formulation, thaw at room temperature 1 vial with DP, lyophilized powder for injection. Record time of removal from the freezer (hh; min). |
| 2 | Collect 1 mL reconstitution composition in a 2 mL syringe. |
| 3 | Record time of starting the reconstitution (hh; min). |
| 4 | Add the content of the syringe containing sterile reconstitution composition (1 mL) to the DP vial. Do not swirl the vial. Remove the syringe from the vial. |

TABLE 1-continued

Reconstitution and emulsification of drug product (DP).

| Step | Description |
|---|---|
| 5 | Allow the mixture to stand for 2 minutes at RT, followed by gentle swirling for 3 minutes. If the content of the vial is not completely dissolved, vortex for 30 seconds. |
| 6 | Collect the contents of the vial (1.0 mL) in a new syringe (syringe A). |
| 7 | Collect 1.0 mL Montanide ISA 51 VG in a third 2 mL syringe (syringe B). |
| 8 | Remove one of the white caps of the T-connector and firmly attach the syringe containing the peptide solution in reconstitution composition (1.0 mL) to the connector (Syringe A). |
| 9 | Remove the second white cap of the T-connector and attach the syringe containing 1.0 mL Montanide ISA 51 (Syringe B) to the connector. |
| 10 | Turn the switch-key and push the content of syringe A first slowly into syringe B and then from syringe B to A. This is 1 cycle. Start the stopwatch. Repeat the cycle in total 50 times 40-50 seconds. Record number of seconds (to be documented by second operator). |
| 11 | Collect the vaccine emulsion in one syringe. Remove the syringe from the T-connector and place a clean needle on the syringe. |

Laser Diffraction Experiments for Testing Emulsion Stability

Emulsion stability was monitored both by visual inspection and by analysis of the particle size distribution using a Malvern Mastersizer 2000.

For particle size analysis, dilution of the emulsion was performed either with water or with a 0.01 M citric acid in water solution to obtain the desired level of obscuration. Montanide was admixed with the reconstitution composition comprising reconstituted DP using a stirrer at a speed of 1750 rpm and a refractive index of 1.46 were applied. Particle size distribution was expressed in D(0.5) and D(0.9) for a volume-based distribution.

Micro Flow Imaging (MFI) for Testing Emulsion Stability

As a second technique for particle size analysis for assessing emulsion stability, Micro Flow Imaging was used. Prior to analysis, a dilution of the emulsion was prepared by adding one droplet of emulsion to 10 mL 0.01M aqueous citric acid solution and mixing until homogeneous, followed by 1:100 dilution of this solution in water. Samples were measured in a purge volume of 0.20 mL for the duration of 0.68 minutes or per 1 million particles in one single run. The results are expressed in Equivalent Circle Diameter (ECD).

Chemical Stability of the Drug Product Solution

For samples showing complete dissolution and an emulsion stability of >2 hours, the chemical stability of the Drug Product solutions (without additional dilution) was monitored with UPLC/MS on a Waters Acquity UPLC system coupled to a Waters TQD mass spectrometer using a Waters Acquity column (type: BEH130, C18, 1.7 μm, 2.1×150 mm). Data processing was performed with Masslynx 4.1 software. UV-detection was performed at 220 nm and the mobile phase was 0.05% TFA and 1% ACN in water (buffer A) and 0.05% TFA in ACN (buffer B) at a flowrate of 0.3 mL/min. The column temperature was 65° C. and the autosampler temperature was 5° C. An injection volume of 5 μL was used, and the gradient profile of Table 2 was applied.

UV-detection was performed during the full length of the gradient, and mass spectrometric analysis was performed from 2-30 min in the positive mode.

For analysis of chemical stability of the Drug Product solutions, samples were analyzed at various time points, at least up to 2 hours after dissolution.

TABLE 2

Gradient profile for UPLC/MS.

| Time (min) | Eluent A (%) | Eluent B (%) |
|---|---|---|
| 0 | 87 | 13 |
| 0.5 | 87 | 13 |
| 5.5 | 79.5 | 20.5 |
| 17.0 | 68 | 32 |
| 22.8 | 45 | 55 |
| 28.5 | 45 | 55 |
| 28.6 | 20 | 80 |
| 30.0 | 20 | 80 |
| 30.1 | 87 | 13 |
| 33.0 | 87 | 13 |

In-Use Chemical Stability of HPV-DP-6P and HPV-DP-7P Vaccine Emulsions

For samples showing complete dissolution, an emulsion stability of >2 hours, and a chemical stability of the Drug Product solutions (without additional dilution) of >2 hours, the in-use chemical stability of the vaccine emulsions with Montanide ISA 51 VG was monitored with UPLC/MS. For analysis of chemical stability of the reconstituted and emulsified Drug Products, samples were analyzed at various time points, at least up to 2 hours after dissolution. UPLC/MS analysis was performed according to the method describe above for chemical stability of the Drug Product solution, using an extra sample preparation step for extraction of the peptides from the vaccine emulsion. For sample preparation of emulsified products, the following steps were applied:

- Take 300 μL Reconstitution Solution and add this to a 15 mL Greiner tube
- Add 100 μL heptane
- Add 200 μL of the Drug Product emulsion. Pipet the solution up and down three times.
- Vortex the mixture for 30 seconds
- Centrifuge the mixture for 5 minutes at 4400 rpm to obtain a two-phase system
- With a 20-200 μL pipette, take a 100 μL sample from the bottom layer and transfer to a total recovery UPLC vial.
- Analyze with UPLC/UV/MS according to the method described for chemical stability of the Drug Product solutions.

Results
Solvent Screening for Reconstitution and Emulsification

Solvents were screened to define a reconstitution composition comprising both an aqueous and organic fraction that is suitable for reconstituting lyophilized peptides and forming a chemically and physically stable emulsion with Montanide. All experiments below were performed with DP-6P. The experiments were verified using DP-5P and DP-7P, but as data were highly comparable, only the data on DP-6P are shown here. Physical stability of the reconstituted proteins and emulsion in this screen was assessed by visual inspection.

As organic fraction, a wide variety of organic solvents was tested. The only single organic solvent capable of completely dissolving DP-6P when admixed with WFI (water for injection) was NMP (Table 3). However, no stable emulsion with Montanide could be obtained when using NMP/WFI as reconstitution composition. The use of saline instead of WFI slightly improved the emulsion stability, but still no emulsions with a stability of ≥2 h could be obtained in a reproducible manner.

TABLE 3

Solvent screening for dissolution of DP-6P.

| Aqueous | Organic 1 | Peptides solubility | Emulsion stability |
|---|---|---|---|
| 600 μL WFI | 400 μL Glycerol | Particles | NA |
| 600 μL WFI | 400 μL PG | Clear viscous solution | NA |
| 600 μL WFI | 400 μL EtOH | Particles | NA |
| WFI | 100-20% DMF | Particles | NA |
| 800 μL WFI | 200 μL NMP | Clear solution | homogeneous < 1 h |
| 800 μL WFI, 0.9% NaCl | 200 μL NMP | Clear solution | homogeneous < 2 h |

Organic Solvent Mixtures in Reconstitution

No single organic solvent was identified that in combination with WFI resulted in complete dissolution of DP-6P. Therefore, combinations of propylene glycol and other solvents were screened as organic fraction in the reconstitution composition. Physical stability was assessed by visual inspection. Chemical stability was assessed using UPLC/MS.

Although still no complete dissolution of DP-6P was observed, the most optional solvent combination identified for dissolution of DP-6P was a mixture of ethanol, propylene glycol and Cremophor EL as emulsifier with WFI (FIG. 1).

To further improve the dissolution process while limiting disulfide formation, the effect of adding several antioxidants and reducing agents to the solvent mixture (mixture of ethanol, propylene glycol, Cremophor EL and WFI) and the peptide solution was assessed. Chemical stability was analyzed with UPLC/MS to monitor the extent of disulfide formation. Addition of DTT (35 molar equivalents compared to peptide) or ascorbic acid (0.1-1% solution in WFI) did not result in a reduction of disulfide formation, whereas the addition of a 0.05-0.1 M aqueous citric acid solution to the solvent mixture resulted in both improved dissolution of DP-6P and limited disulfide formation of area % values of ≤1% per disulfide two hours after dissolution of the Drug Product. Citrate buffer at pH3 and a concentration of 0.05-0.1 M could not be used for emulsification because of poor peptide dissolution (data not shown). FIG. 2 presents chemical stability in time (t=0 and t=2 h) of DP reconstituted in a mixture of 1 mg/mL ascorbic acid in water, propylene glycol and ethanol versus a mixture of 0.1M citric acid in water, propylene glycol, ethanol, and Cremophor EL.

Testing Reconstitution Compositions after Reconstitution and after Subsequent Emulsification Cremophor EL as emulsifier is less preferred in vaccine formulations because of reported side effects at higher dosages. However, the dissolving and emulsifying properties of Tween 80, cyclodextrins, and Triton X as alternatives for Cremophor EL, were inadequate (data not shown). Upon visual inspection, promising results were obtained with a combination of propylene glycol, ethanol, citric acid in WFI and 2% Tween20. The results of emulsification experiments as summarized in Table 4 show that emulsions comprising propylene glycol and ethanol in combination with either Cremophor EL or Tween 20 result in most stable emulsions. However, it appeared that the chemical stability in solution of both DP-6P and DP-7P was significantly worse in the presence of Tween20 instead of Cremophor EL, i.e. with area % values of over 5% per disulfide two hours after dissolution of the Drug Product (see FIG. 3 for UPLC chromatograms of DP-6P; results for DP-5P and DP-7P were highly similar (data not shown).

Taken together, from the data presented in Table 4 and FIG. 3 it can be concluded that Cremophor EL is preferred as an emulsifier for DP-6P emulsions with Montanide, based on both physical and chemical stability of the product.

To demonstrate that the results obtained for chemical stability of Drug Product in solution can be translated to the in-use chemical stability of the Drug Product in the vaccine emulsion, the in-use stability of DP-6P and DP-7P vaccine emulsions was studied and results are presented in FIGS. 4 A, B, C and D. These results confirm that, after the emulsification step, the chemical stability of the Drug Products in the vaccine preparations is retained.

TABLE 4

Solvent screening with premixed organic and aqueous solvents (1 mL).

| Citric acid solution | Organic 1 | Organic 2 | Organic 3 | Peptides solubility | Physical emulsion stability |
|---|---|---|---|---|---|
| 0.1M, 800 μL | PG (3) | EtOH (2) | Cremophor EL (1) | + | − |
| 0.1M, 800 μL | PG (1) | 0 | Cremophor EL (1) | − | − |
| 0.1M, 800 μL | PG (2) | EtOH (1) | Cremophor EL (1) | + | − |
| 0.1M, 800 μL | PG (3) | EtOH (3) | Cremophor EL (2) | − | NA |
| 0.1M, 800 μL | PG (1) | EtOH (1) | Cremophor EL (2) | + | − |
| 0.1M, 775 μL | PG (2) | EtOH (1) | Cremophor EL (1) | −+ | − |

TABLE 4-continued

Solvent screening with premixed organic and aqueous solvents (1 mL).

| Citric acid solution | Organic 1 | Organic 2 | Organic 3 | Peptides solubility | Physical emulsion stability |
|---|---|---|---|---|---|
| 0.1M, 750 μL | PG (3) | EtOH (2) | Cremophor EL (1) | −+ | − |
| 0.1M, 750 μL | PG (1) | EtOH (2) | Cremophor EL (1) | −+ | + |
| 0.1M, 750 μL | 0 | EtOH (4) | Cremophor EL (1) | −+ | − |
| 0.1M, 700 μL | PG (3) | EtOH (2) | Cremophor EL (1) | − | − |
| 0.1M, 800 μL | PG (1) | EtOH (2) | Tween 20 (1) | −+ | + |
| 0.1M, 750 μL | PG (1) | EtOH (2) | Tween 20 (1) | −+ | NA |
| 0.1M, 600 μL | PG (1) | EtOH (2) | Tween 20 (1) | − | NA |
| 0.1M, 800 μL | PG (1) | EtOH (2) | Tween 20, 50% aq (1) | −+ | + |
| 0.1M, 800 μL | PG (1) | EtOH (2) | Tween 20, 25% aq (1) | −+ | + |
| 0.1M, 750 μL | PG (1) | EtOH (2) | Triton X (1) | − | NA |
| 0.1M, 600 μL | PG (1) | EtOH (2) | Triton X (1) | − | NA |
| 0.05M, 800 μL | PG (1) | EtOH (1) | Cremophor EL (2) | + | − |
| 0.05M, 775 μL | PG (2) | EtOH (1) | Cremophor EL (1) | −+ | − |
| 0.05M, 750 μL | PG (2) | EtOH (1) | Cremophor EL (1) | −+ | + |
| 0.05M, 700 μL | PG (2) | EtOH (1) | Cremophor EL (1) | − | ++ |

Fine-Tuning for Robustness in Emulsification
Peptide Solubility and Emulsion Stability A subsequent series of experiments was performed in which the ratio of PG/EtOH/Cremophor EL was varied, two different concentrations of citric acid solution were tested, different emulsification methods were applied and the ratio of organic vs. aqueous components of the mixture was varied. In general, 1 mL reconstitution composition was prepared by mixing the organic and aqueous solvents before adding them to the lyophilized Drug Product. Subsequently, an emulsion was prepared by adding 1 mL Montanide to the 1 mL of aqueous peptide solution using different mixing steps and/or connectors as indicated in Table 5 and 6.

TABLE 5

Variation in emulsification method using different reconstitution compositions:
A = 800 μL 0.05M citric acid and 200 μL PG/EtOH/Cremophor EL (1:1:2);
B = 800 μL 0.05M citric acid and 200 μL PG/EtOH/Cremophor EL (2:1:1);
C = 750 μL 0.1M citric acid and 250 μL PG/EtOH/Cremophor EL (2:1:1);
D = 750 μL 0.1M citric acid and 250 μL PG/EtOH/Cremophor EL (1:2:1); and,
E = 700 μL 0.1M citric acid and 300 μL PG/EtOH/Cremophor EL (2:1:1).

| Emulsification method | Buffer composition | Peptides solubility | Emulsion stability |
|---|---|---|---|
| 20 slow* cycles and 80 fast* cycles | A | + | − |
| 40 cycles in 40 sec | A | + | − |
| 20 slow cycles and 80 fast cycles | B | + | − |
| 10 slow cycles and 40 fast cycles | B | + | − |
| 20 slow cycles and 80 fast cycles | C | +− | + |
| 10 slow cycles and 40 fast cycles | C | +− | +− |
| 20 slow cycles and 40 fast cycles | C | +− | + |
| 40 fast cycles | C | +− | + |
| 40 fast cycles | D | +− | + |
| 20 slow cycles and 40 fast cycles | E | − | ++ |
| 40 fast cycles | E | − | ++ |

*Slow cycles: 2 seconds per cycle. Fast cycles: 1 second per cycle.

Peptide Emulsion Stability in More Detail: PSD Analysis by Laser Diffraction

For five different reconstitution compositions, the effect of different emulsification methods on particle size was analysed with laser diffraction, using a Malvern Mastersizer 2000. For all samples, 1 mL reconstitution composition was prepared by mixing the organic and aqueous solvents before adding them to the lyophilized Drug Product. Subsequently, an emulsion was prepared by adding 1 mL Montanide to the 1 mL of aqueous peptide solution. Mixing of the organic and aqueous phases was performed in three different ways:

Using the T-connector process and performing mixing cycles as indicated in Table 6;

Using an I-connector and performing mixing cycles as indicated in Table 6; or,

Adding 1 mL Montanide to the vial containing the peptide solution in reconstitution composition, and vortexing the mixture during 30 seconds.

A summary of the results is presented in Table 6. Approximate values for D(0.5) are given (volume based distribution).

TABLE 6

Emulsification of peptide formulations characteristics and average D(0.5) values using different reconstitution compositions:
A = 600 μL 0.1M citric acid and 400 μL PG/EtOH/Cremophor EL (5:4:2);
B = 750 μL 0.1M citric acid and 250 μL PG/EtOH/Cremophor EL (2:1:1);
C = 750 μL 0.1M citric acid and 250 μL PG/EtOH/Cremophor EL (1:2:1);
D = 775 μL 0.1M citric acid and 225 μL PG/EtOH/Cremophor EL (2:1:1); and,
E = 800 μL 0.1M citric acid and 200 μL PG/EtOH/Cremophor EL (2:1:1).

| Reconstitutio composition | Emulsification process | Solubility | D(0.5) | Stability |
|---|---|---|---|---|
| A | T-connector, 20 slow and 80 fast cycles | − | 3 μm | ≥3 h |
| A | Vortex 30 seconds | − | 11 μm | 3 h |
| B | T-connector, 20 slow and 80 fast cycles | +− | 5-7 μm* | ≥3 h |
| B | T-connector, 40 fast cycles | +− | 9 μm | ≥3 h |
| B | I-connector, 10 slow and 40 fast cycles | +− | 11 μm | ≥2 h |
| C | T-connector, 40 fast cycles | +− | 4 μm | ≥2 h |
| D | T-connector, 40 fast cycles | +− | 11 μm | 1 h |
| E | T-connector, 20 slow and 80 fast cycles | + | 11 μm | 1 h |
| E | I-connector, 20 slow and 80 fast cycles | + | 12 μm | 1 h |

*Variation in PSD was observed for analysis diluted in WFI or diluted in 0.01M citric acid solution Both from Table 5 and Table 6, it appears that no difference in emulsion stability was observed between the different mixing methods and/or different types of connectors used. However, vortexing the mixture instead of using a connector resulted in emulsions with a much larger particle size, which is less favorable for stability. In general emulsions with a smaller particle size are more stable.

Further, emulsion stability was improved by increasing the percentage of the organic fraction (mixture) in the total volume of reconstitution composition. However, the highest volumes of organic content tested here (300-400 μL) resulted in decreased solubility of the Drug Product. Therefore, the optimum of organic content was between 200 and 300 μL per mL (about 250 μL) reconstitution composition. In addition, variation in the concentration of the citric acid (0.05 or 0.1M) solution did not seem to affect the emulsion stability, while slightly better dissolution of DP-6P was obtained when a 0.1 M citric acid solution was used.

Particle Size Analysis using Micro Flow Imaging

To study the effect of citric acid concentration on emulsion stability and particle size of the emulsion in more detail, additional particle size analysis experiments were compared using the solvent that resulted in the smallest particle size after emulsification with 1 mL Montanide, i.e. a reconstitution composition with an organic- to aqueous-phase ratio of 1:3, wherein the organic phase contains PG, EtOH and Cremophor EL in a ratio of PG to EtOH to Cremophor EL of 1:2:1 (Table 6). Direct comparison experiments were performed, wherein the molar amount of citric acid in the aqueous phase was varied (0.05 and 0.1M citric acid, i.e. an end concentration of citric acid in reconstitution composition of 0.038 and 0.075M citric acid, respectively). DP-6P was dissolved in 1 mL of such reconstitution composition, followed by emulsification with 1 mL Montanide using a T-connector process and performing 50 fast mixing cycles. In these experiments, both dissolution of the Drug Product and particle size and emulsion stability were analyzed. As a read-out, Micro Flow Imaging (MFI) was performed using an MFI 5200 in order to visualize the particles with a camera so that irregularities can be studied visually. The PSD-comparison of 0.05 and 0.1M citric acid of citric acid reconstitution composition is shown in FIG. 5.

As can be seen in FIG. 5, the concentration of citric acid solution does not influence the PSD of the emulsion. However, dissolution of the Drug Product was slightly better when 0.1M citric acid was used. FIG. 6 presents MFI results of three independent preparations of a DP-6P emulsion (FIG. 6, panel A) or two independent preparations analyzed at two different time points after preparation (FIG. 6, panel B), wherein the Drug Product has been reconstituted using the same solvent combination (750 μL 0.05M citric acid+ 250 μL PG/EtOH/Cremophor EL 1:2:1). Very robust PSD results were obtained. In addition, the emulsions were all stable for at least 2 hours.

Application of Preferred Reconstitution Solvent and Emulsification Method on DP-6P and DP-7P Since 750 μL citric acid solution+250 μL PG/EtOH/Cremophor EL 1:2:1 was shown to give robust PSD results for DP-6P emulsions, and the use of 0.1M citric acid resulted in the best dissolution of the Drug Product, this solvent combination was tested extensively for the preparation of DP-6P and DP-7P emulsions.

DP-6P and DP-7P emulsions were prepared according to the instructions in Table 1. Briefly, 1 mL of reconstitution composition (750 μL 0.1M citric acid+250 μL PG/EtOH/Cremophor EL 1:2:1) was added to the lyophilized Drug Product, the resulting solution was mixed with 1 mL Montanide using a T-connector and applying 50 fast mixing cycles. PSD values for MFI analyses are given in ECD (equivalent circle diameter) and a number-based distribution is given. It should be noted that MFI and laser diffraction are complementary techniques. Therefore, a direct comparison of average particle size values obtained by laser diffraction and by MFI cannot be performed.

TABLE 7

DP-6P Particle size D (0.5) values in μm.

| | T = 0 | T = 1 | T = 2 | T = 3 |
|---|---|---|---|---|
| Prep 1 | 1.77 | 1.71 | 1.70 | 1.71 |
| Prep 2 | 1.73 | 1.62 | 1.69 | 1.69 |
| Prep 3 | 1.61 | 1.73 | 1.75 | 1.69 |
| Average | 1.70 | 1.69 | 1.71 | 1.70 |

TABLE 8

DP-7P Particle size D (0.5) values in μm.

|  | T = 0 | T = 1 | T = 2 | T = 3 |
|---|---|---|---|---|
| Prep 1 | 1.64 | 1.59 | 1.56 | 1.59 |
| Prep 2 | 1.59 | 1.61 | 1.61 | 1.57 |
| Prep 3 | 1.65 | 1.66 | 1.63 | 1.55 |
| Average | 1.63 | 1.62 | 1.60 | 1.57 |

Table 7 and 8 show that by using a reconstitution composition comprising 750 μL 0.1M citric acid+250 μL PG/EtOH/Cremophor EL 1:2:1 (i.e. 750 μL 0.1M Citric acid in water, 62.5 μL Propylene Glycol, 125 μL Ethanol and 62.5 μL Cremophor EL), for both DP-6P and DP-7P emulsions can be prepared that are stable for at least 3 hours.

Example 2

Introduction

Therapeutic efficacy of SLP vaccination in combination with CpG1826 has previously been demonstrated in mice carrying established TC-1 tumors, which express the oncogenic E6 and E7 proteins of HPV16 (Zwaveling et al., *J. Immunol.* (2002) 169:350-358). To assess whether SLPs retain functionality in the most optimal formulation identified in Example 1 (750 μL 0.1M citric acid+250 μL PG/EtOH/Cremophor EL 1:2:1), we therapeutically vaccinated mice carrying a TC-1 tumor with an SLP harboring the $D^b$-restricted CTL epitope RAHYNIVTF (represented herein by SEQ ID NO: 67), reconstituted either in DMSO/WFI or the novel reconstitution composition. All vaccines were subsequently emulsified in Montanide. Tumor outgrowth was monitored for 75 days. At the peak of the vaccine-induced T cell response, the percentage and phenotype of RAHYNIVTF-specific CD8+ T cells was determined in the blood. SLP reconstituted in DMSO/WFI and the novel reconstitution composition showed a similar potency in inducing TC-1 tumor regression. Mice vaccinated with the SLP reconstituted in the novel solution showed a higher percentage of RAHYNIVTF-specific CD8+ T cells in the blood.

Materials

TABLE 9

Materials applied during TC-1 tumor experiment.

| Material | Origin/supplier |
|---|---|
| C57BL/6 female mice, 6-8 weeks old | Harlan Laboratories |
| Montanide ISA VG51 | Seppic; batch 2384535/U40740; exp 13FEB17 |
| CpG ODN1826 (5 mg/ml) | Invivogen; cat no tlrl-1826 |
| DMSO | Mylan; lot nr 140706; exp JUN2017 |
| WFI | Fresenius Kabi; W005 4B03; exp 6MAR18 |
| KLRG1-PeCy7 | eBioscience; cat nr 25-5893-82 |
| CD62L-Alexa780 | eBioscience; cat nr 47-0621-82 |
| CD44-Pacific Blue | BioLegend; cat nr 103020 |
| CD127-Biotin | eBioscience; cat nr 13-1271-85 |
| CD8a-Alexa700 | eBioscience; cat nr 56-0081-82 |
| CD3-V500 | BD; cat nr 560771 |
| Streptavidin-Qdot605 | ThermoFischer; cat nr Q10101MP |
| 7-AAD viability staining | ThermoFisher, cat nr A1310; exp 22SEP16 |
| $D^b$-RAHYNIVTF tetramer | Production of LUMC |
| Trypsin | Gibco (Life Technologies) cat nr 25200-056 |
| Geneticin (G418) | Gibco (Life Technologies) cat nr 10131-027 |
| BSA | Roche Diagnostics; cat nr 10735078001 |
| Lysis buffer | LUMC Pharmacy |
| T-connector Discofix C | B Braun; 16494C |
| NORM-JECT Luer-lock 2 ml syringes | HSW; 4010-000V0 |
| NORM-JECT Luer-lock 1 ml syringes | HSW; 4010-200V0 |
| BD Microlance 3; 25G (0.5 × 16 mm) | BD; cat nr 300600 |
| Disposables | Various; LUMC |

Methods

Vaccine Preparation

The following groups of mice were included in the study:

Group 1: (n=5) 40% v/v DMSO/WFI emulsified 1:1 with Montanide ISA VG51.

Group 2: (n=5) Reconstitution composition (750 μL 0.1M Citric acid in water, 62.5 μL Propylene Glycol, 125 μL Ethanol and 62.5 μL Cremophor EL per mL) emulsified 1:1 with Montanide ISA VG51.

Group 3: (n=10) SLP GQAEPDRAHYNIVTFCCKCDSTLRLCVQSTHVDIR and 20 μg CpG ODN1826/mouse dissolved in 40% v/v DMSO/WFI, emulsified 1:1 with Montanide ISA VG51.

Group 4: (n=10) SLP GQAEPDRAHYNIVTFCCKCDSTLRLCVQSTHVDIR (SEQ ID NO: 6) and 20 μg CpG ODN1826/mouse dissolved in Reconstitution composition (750 μL 0.1M Citric acid in water, 62.5 μL Propylene Glycol, 125 μL Ethanol and 62.5 μL Cremophor EL per mL), emulsified 1:1 with Montanide ISA VG51.

For mice in Group 1, a solution was prepared by admixing and subsequently swirling 400 μL DMSO and 600 μL WFI. The solution was taken up in a 2 mL Luer-Lock syringe (Syringe A). In another 2 mL Luer-Lock syringe (Syringe B) 1 mL of Montanide ISA VG51 was taken up, after which both syringes were connected to a T-connector. An emulsion was generated by mixing the contents back and forth extensively. After mixing, the syringes were disconnected and a 25G needle was placed on the syringe containing the emulsion. Per mouse, 100 μL was injected in the left flank subcutaneously.

The vaccine prepared for Group 2 was prepared in an identical manner, only differing by the use of reconstitution composition (750 μL 0.1M citric acid in water and 250 μL PG/EtOH/Cremophor EL 1:2:1, i.e. 0.075M citric acid, 6.25% v/v propylene glycol CAS no. 57-55-6, 12.5% v/v ethanol and 6.25% v/v polyoxyethyleneglyceroltriricinoleate 35 CAS no. 61791-12-6 in water) instead of DMSO and WFI. The vaccine for Group 3 was prepared by first dissolving the contents of a vial containing 1.5 mg SLP represented herein by SEQ ID NO: 6 (GQAEPDRAHYNIVTFCCKCDSTLRLCVQSTHVDIR) in 400 μL DMSO. The SLP was produced via Fmoc solid phase peptide synthesis (*Fmoc Solid Phase Peptide Synthesis, A Practical Approach*, W. C. Chan, P. D. White Eds, Oxford Univ. Press 2000). Then, 520 μL WFI and 80 μL CpG ODN1826 (stock 5 mg/ml) were added to the peptide in DMSO. After taking up this solution in a 2 mL Luer-Lock syringe, the same vaccine preparation protocol was followed as for Group 1 by emulsifying with Montanide ISA VG51. The preparation of vaccine for Group 4 was identical to the protocol for Group 3, only differing in the first step in which the contents of a vial containing 1.5 mg SLP SEQ ID NO: 6 were dissolved in 920 μL Reconstitution composition and adding 80 μL CpG ODN1826 (stock 5 mg/ml).

Therapeutic Vaccination

TC-1 tumor cells, expressing the oncogenic E6 and E7 proteins of HPV16 were cultured in complete IMDM culture medium, supplemented with 400 μg/ml geneticin. On day 0, TC-1 cells were harvested using trypsin and washed 3 times with PBS/0.1% BSA. Directly after harvesting, 100,000 TC-1 cells were injected s.c. in the right flank of 40 female C57BL/6 mice. On day 8, all mice were s.c. vaccinated in the left flank as described in the section Vaccine preparation. The tumor size of all mice was monitored at least twice a week using a caliper up to 75 days after tumor challenge. The study was carried out as displayed in FIG. 7.

Measurement of Strength of T Cell Response in Blood

On day 9 after vaccination, blood was drawn from the tail vein of all mice. Blood samples were transferred to a 96-wells culture plate and centrifuged for 5 minutes at 1600 rpm. Erythrocytes were lysed by suspending blood cell pellets in Lysis buffer until orange coloration was observed. Subsequently, cells were washed in FACS buffer and stained with the fluorescent antibodies, the $D^b$-RAHYNIVTF-APC tetramer and 7-AAD mentioned in the Materials section above. After 30 minutes of incubation on ice, cells were washed and analyzed on a BD LSRII flow cytometer in the Leiden University Medical Center (Dept. of Rheumatology).

Results

Tumor Outgrowth Similar Between Vaccinated Groups

By monitoring the tumor size at least twice a week, a growth curve could be created for each individual mouse. In FIG. 8, the outgrowth of tumors is shown for the different groups. Tumor regression is observed in all mice vaccinated with SLP 6 and CpG1826. Tumors in the control groups receiving the vehicle only, either DMSO/WFI and Montanide or Reconstitution composition and Montanide, rapidly grow out. Besides natural variations, no clear differences are observed between both SLP-vaccinated groups. See FIG. 9A for a Kaplan-Meier survival plot, showing no differences between the vaccinated groups.

Vaccine-Induced Tetramer-Positive CD8+ T Cells

Figure 9B:
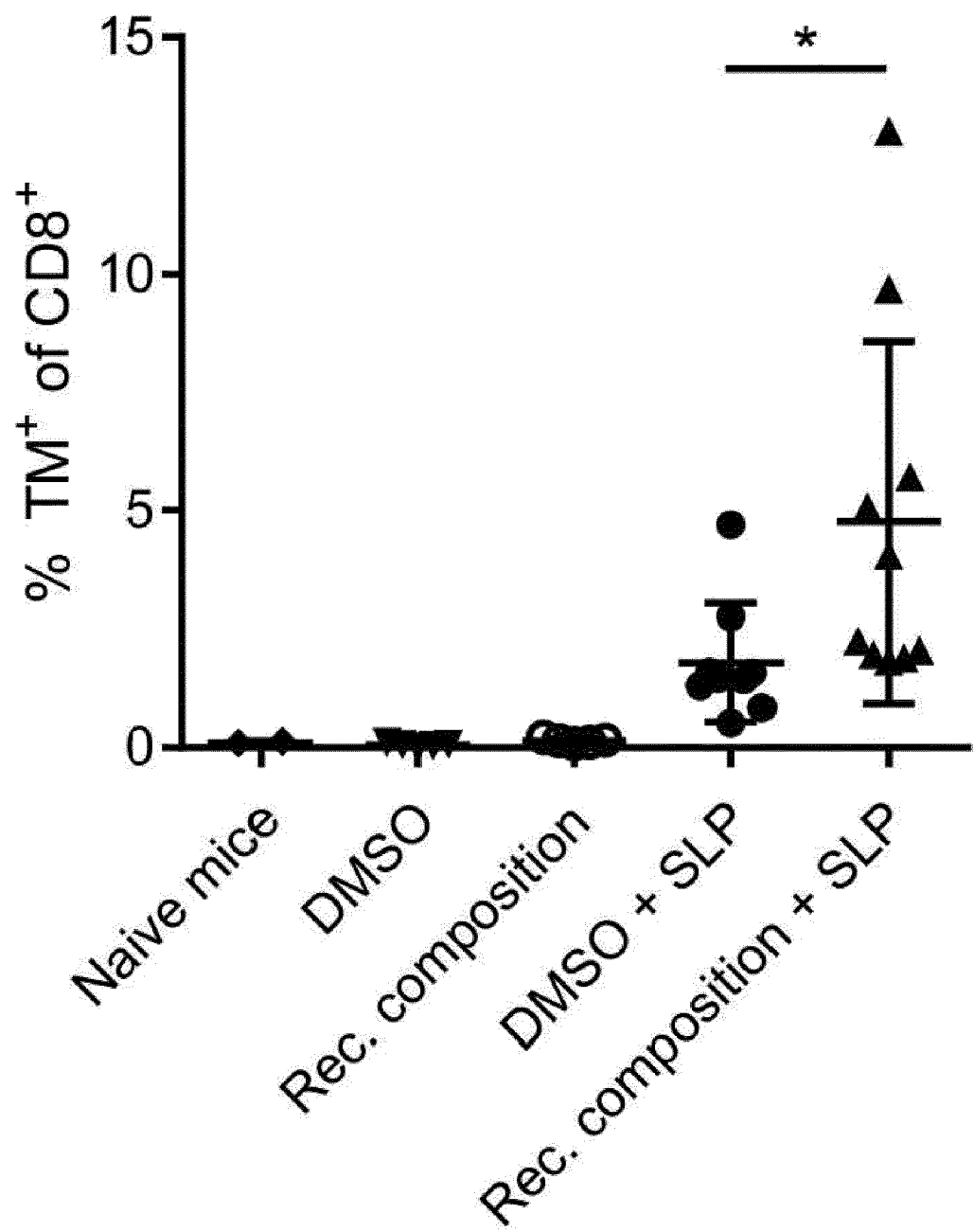

FIG. 9B shows the percentage of induced $D^b$-RAYNIVTF (tetramer) positive CD8+ T cells. Mice in group 4 (Rec. composition+SLP) show an enhanced tetramer-positive CD8+ T cell response, indicating that SLP and CpG formulated in Reconstitution composition is more effective than SLP and CpG formulated in an emulsion of DMSO/WFI and Montanide in the priming of specific murine CD8+ T cells. See Table 9 for the average percentages and standard deviations per group.

Significant differences were determined using an unpaired t-test, resulting in a p-value of p=0.022 between group 3 and 4.

Expression of KLRG1 and CD62L Indicate Favourable Antitumor Expression Profile After Vaccination with SLP 6

A study by Van Duikeren et al. (*J Immunol*, 2012; 189(7): 3397-403) aimed to identify parameters that correlated with the induction of an effective antitumor response. By identifying such biomarkers, different vaccine compositions can be tested in non-tumor bearing mice with prognostic value in tumor models. The authors found a correlation between the expression of KLRG1 and absence of CD62L expression on the one hand and effective antitumor immune responses on the other hand. We determined the percentages of KLRG1- and CD62L-expressing $D^b$-RAHYNIVTF+ CD8+ T cells in the blood of vaccinated mice on day 9 after vaccination using flow cytometry. No difference in percentage of RAHYNIVTF-specific KLRG1+ CD62L− CD8+ T cells is observed between groups 3 and 4. Not enough RAHYNIVTF-specific CD8+ T cells were detected to reliably study the expression of KLRG1 and CD62L in the groups of mice vaccinated with vehicle only (Group 1 and 2). See Table 10 for the average percentages and standard deviations per group.

TABLE 10

Average percentages and SD of tetramer+ CD8+ T cells, and averages and percentages of expression of CD62L and KLRG1 of tetramer+ CD8+ T cells in groups of mice vaccinated with SLP.

| Group | | % Tm+ of CD8 | % of TM+ CD8 T cells | |
|---|---|---|---|---|
| | | | % CD62L−  KLRG1+ | % CD62L+  KLRG1+ |
| 1 | Average | 0.1 | # | # |
|   | SD      | 0   |   |   |
| 2 | Average | 0.1 | # | # |
|   | SD      | 0.1 |   |   |
| 3 | Average | 1.4 | 51.9 | 4.0 |
|   | SD      | 1.0 | 14.9 | 3.2 |
| 4 | Average | 4.8* | 52.2 | 4.0 |
|   | SD      | 3.8  | 16.6 | 2.0 |

*indicates significant difference (p < 0.05) between groups 3 and 4 as determined by unpaired t-test.

Discussion

No differences were observed in overall tumor outgrowth between the groups of mice vaccinated with SLP 6 dissolved either in DMSO/WFI or Reconstitution composition. We did observe enhanced induction of specific CD8+ T cells in the mice vaccinated with the SLP dissolved in Reconstitution composition as compared to the group of mice vaccinated with the SLP dissolved in DMSO/WFI.

The adjuvanting properties of Montanide have been ascribed to the formation of an antigen depot and induction of local inflammation and cell death, which favors maturation of antigen-presenting cells. The enhanced induction of tetramer+ CD8+ T cells in the group of mice vaccinated with the SLP dissolved in Reconstitution composition suggests that the combination of this solution with Montanide constitutes an emulsion with beneficial antigen release properties or local stimulation of antigen-presenting cells. The favourable profile of KLRG1 expression and absence of CD62L was similar between both groups of mice vaccination with the SLP. The data demonstrate that SLPs reconstituted in the reconstitution composition of the invention maintain their immunogenic capacity as compared to the originally used reconstitution composition (DMSO/WFI).

Example 3

Material

The following lyophilized peptide composition was used: P53 DP5P: comprising peptides represented herein by SEQ ID NO: 191, 193, 194, 201 and 203.

The following chemicals were used: Cremophor EL. (Sigma Aldrich. Kolliphor EL); Propylene Glycol (≥99.5%. Sigma Aldrich); Ethanol (Absolute. VWR Emprove® Ph Eur. BP.USP); Citric acid (≥99%. Sigma Aldrich); MilliQ water; Sterile Montanide ISA 51VG (SEPPIC.)

The following equipment was used: Syringe extrusion devices (Discofix-3 T-connector. B. Braun); DMSO-resistant syringes (2 mL NORM-JECT Luer Lock. Henke Sass Wolf); Waters UPLC/MS system EQP-004; Protein Simple MFI 5200

Methods

Preparation of the vaccine emulsion and a placebo emulsion was performed as described in Table 1.

Analysis of chemical stability was performed by UPLC-MS as described in Example 1, at the section describing methods for analysis of in-use chemical stability of HPV-DP-6P and HPV-DP-7P vaccine emulsions including extraction of the peptides from the vaccine emulsion.

Particle size analysis was performed by Micro Flow Imaging. Prior to analysis a dilution of the vaccine emulsion was prepared by adding 10 μL of emulsion to 10 mL Reconstitution Solution and mixing until homogeneous, followed by 1:500 dilution of this solution in Reconstitution Solution.

Analysis settings of MFI 5200:
Method: DS500.2
Sample volume: 1 mL
Purge volume: 0.20 mL
Analysis: 0.68 min or 1.000.000 particles
Consecutive runs: 1

Results are expressed in Equivalent Circle Diameter (ECD) and a number-based distribution is given. Particles≥15 μm are filtered from the results since these are known to be artefacts rather than emulsion particles.

Results

Purity of Reconstituted Drug Product

Purity of the Drug Product at different time points was calculated as follows:

Purity (%)=100%−Sum of impurities≥0.05% area

An overview of the in-use purity of the P53-DP-5P vaccine product is given in Fout! Verwijzingsbron niet gevonden.

TABLE 11

Overview of purity of reconstituted P53-DP-5P during storage at room temperature.

| PRODUCT: | P53-DP-5P IN-USE STORAGE TIME | | | |
|---|---|---|---|---|
| TEST | t = 0 h | t = 1 h | t = 2 h | t = 3 h |
| Purity [Area %] | 93.4 | 91.6 | 90.9 | 89.8 |
| Total related substances (≥0.05%) [Area %] | 6.6 | 8.4 | 9.1 | 10.2 |

As can be seen from Fout! Verwijzingsbron niet gevonden., purity of the Drug Products slowly decreases but is still ≥90.0% two hours after vaccine preparation. Example chromatograms of UPLC analysis of the vaccine at t=0 and t=2 h are presented in FIG. 10.

Identification of main peaks and impurities with an area≥1.0% area was performed using mass spectrometry. All related substances with an area≥1.0% area are reported and identified by comparing the measure m/z values with molecular masses of the peptide sequences and their known and expected modifications. The resulting overview of related substances for an in-use storage of P53-DP-5P for up to 3 hours is given in Table 12.

TABLE 12

Overview and identification of related substances of reconstituted P53-DP-5P. In-use stability up to 3 h after reconstitution.

| | RETENTION TIME (min.) | IN-USE STORAGE TIME | | | | SEQ ID NO |
|---|---|---|---|---|---|---|
| | | t = 0 h | t = 1 h | t = 2 h | t = 3 h | |
| Peptides and related substances (≥0.05%) [Area %] | 4.97 | 13.00 | 12.02 | 11.87 | 11.63 | 194 |
| | 7.99 | 12.43 | 11.73 | 11.72 | 11.60 | 201 |
| | 9.57 | 23.90 | 22.38 | 22.31 | 22.19 | 193 |
| | 14.14 | 30.37 | 28.75 | 28.81 | 28.81 | 191 |
| | 16.82 | < | 1.05 | 1.54 | 1.87 | 203 intramolecular disulfide |
| | 19.46 | 13.73 | 16.73 | 16.21 | 15.56 | 203 |

Recovery of Drug Product from the Emulsion

The recovery of the five individual peptides present in P53-DP-5P from the emulsion was verified by comparison of emulsified and non-emulsified sample signals. An overview of the results is given in Fout! Verwijzingsbron niet gevonden.

TABLE 13

Overview of recovery by comparison of emulsified and non-emulsified sample signals.

| | IN-USE STORAGE TIME | | | | |
|---|---|---|---|---|---|
| | t = 0 h | t = 1 h | t = 2 h | t = 3 h | SEQ ID NO |
| Recovery | 97 (0.6) | 97 (0.8) | 96 (2.4) | 94 (2.3) | 194 |
| (RSD) | 101 (2.0) | 103 (3.8) | 104 (5.1) | 102 (5.1) | 201 |
| Both | 98 (0.6) | 99 (1.1) | 99 (1.9) | 98 (1.3) | 193 |
| values | 96 (0.3) | 98 (1.4) | 99 (1.7) | 98 (1.1) | 191 |
| given as % | 70 (8.6) | 92 (3.4) | 90 (4.4) | 86 (4.8) | 203 |

Physical Stability

Physical stability was analysed by particle size analysis with MFI. Results are expressed in Equivalent Circle Diameter (ECD). Mean particle size values are given in Table 14, calculated from a number-based distribution.

TABLE 14

Mean particle size (ECD in μm) of P53 DP5P vaccine emulsions

| | T = 0 h | T = 1 h | T = 2 h | T = 3 h |
|---|---|---|---|---|
| Prep 1 | 1.91 | 1.95 | 1.93 | 2.01 |
| Prep 2 | 1.85 | 1.90 | 1.92 | 1.93 |
| Average | 1.88 | 1.93 | 1.93 | 1.97 |

Conclusion

Dissolution was successfully performed for a mixture containing 5 SLPs derived from the P53 antigen (P53 DP-5P).

Both chemical and physical in-use stability of the vaccine product was studied. Analysis of related substances and calculation of purity as summarized in Table 11 for P53 DP-5P shows that the purity of the Drug Product is ≥90.0% two hours after vaccine preparation. Only one related substance with a peak area % of ≥1% was observed. MS-identification showed that this peak is the intramolecular disulfide of the peptide set forth in SEQ ID NO: 203.

Physical stability of the P53 DP-5P vaccine product was studied by monitoring its particle size with MFI. The results of the particle size analysis are summarized in Table 14 and show that the particle size does not change up to three hours after vaccine preparation. In addition, all vaccine products were monitored by visual inspection during the stability study and no phase separation was observed at any time point.

Example 4

Material and Methods

The following lyophilized peptide composition was used:
PRAME DP5P: comprising peptides represented herein by SEQ ID NO: 153, 155, 156, 160 and 166:

A set of five PRAME-derived peptides was selected based on UPLC retention times, variation in amino acid composition, and solubility in reconstitution solution as determined by visual inspection.

Other materials and methods used were the same as in Example 3.

Results

Purity of Reconstituted Drug Product

Purity of the Drug Product at different time points was calculated as follows:

Purity (%)=100%−Sum of impurities≥0.05% area

An overview of the in-use purity of the PRAME-DP-5P vaccine product is given in Table 15. It should be noted that the purity of lyophilized PRAME-DP-5P is already below 90%. Nevertheless, the very limited decrease in purity over time demonstrates good chemical stability of this reconstituted drug product.

TABLE 15

Overview of purity of reconstituted PRAME-DP-5P during storage at room temperature.

| PRODUCT: | PRAME-DP-5P | | | |
|---|---|---|---|---|
| | IN-USE STORAGE TIME | | | |
| TEST | t = 0 h | t = 1 h | t = 2 h | t = 3 h |
| Purity [Area %] | 82.9 | 83.7 | 82.5 | 82.2 |
| Total related substances (≥0.05%) [Area %] | 17.1 | 16.3 | 17.5 | 17.8 |

The low purity decrease over time indicates high chemical stability. The impurities with an area≥1.0% area in PRAME-DP-5P were already present in the mixture before reconstitution. Since no significant increase of these impurities was observed in this stability study, no identification of the impurities was performed. The resulting overview of related substances for an in-use storage of PRAME-DP-5P for up to 3 hours is given in Table 16.

TABLE 16

Overview and identification of related substances of reconstituted PRAME-DP-5P. In-use stability up to 3 h after reconstitution.

| | RETENTION TIME (min.) | IN-USE STORAGE TIME | | | | SEQ ID NO |
|---|---|---|---|---|---|---|
| | | t = 0 h | t = 1 h | t = 2 h | t = 3 h | |
| Related substances (≥0.05%) [Area %] | 10.68 | 23.35 | 22.85 | 22.65 | 22.62 | 155 |
| | 17.50 | 13.61 | 13.49 | 13.34 | 13.40 | 160 |
| | 18.91 | 13.49 | 14.15 | 13.81 | 13.59 | 166 |
| | 20.05 | 21.89 | 22.70 | 22.51 | 22.59 | 153 |
| | 21.15 | 10.56 | 10.52 | 10.17 | 9.98 | 156 |

Recovery of Drug Product from the Emulsion

The recovery of the five individual peptides present in PRAME-DP-5P from the emulsion was verified by comparison of emulsified and non-emulsified sample signals. An overview of the results is given in Table 17.

TABLE 17

Overview of recovery by comparison of emulsified and non-emulsified sample signals.

| | IN-USE STORAGE TIME | | | | |
|---|---|---|---|---|---|
| | t = 0 h | t = 1 h | t = 2 h | t = 3 h | SEQ ID NO |
| Recovery | 81 (9.8) | 87 (3.8) | 84 (2.1) | 81 (7.8) | 155 |
| (RSD) | 81 (10.4) | 87 (3.7) | 84 (0.9) | 82 (8.2) | 160 |
| Both | 74 (10.8) | 84 (3.9) | 80 (1.0) | 77 (8.1) | 166 |

TABLE 17-continued

Overview of recovery by comparison of emulsified and non-emulsified sample signals.

| | IN-USE STORAGE TIME | | | | |
|---|---|---|---|---|---|
| | t = 0 h | t = 1 h | t = 2 h | t = 3 h | SEQ ID NO |
| values | 76 (10.7) | 86 (3.3) | 83 (0.2) | 81 (8.6) | 153 |
| given as % | 78 (10.5) | 84 (3.6) | 80 (1.0) | 76 (7.8) | 156 |

Conclusion

The purity of the PRAME DP-5P was not fully satisfactory (<90%), but the decrease in purity of the reconstituted vaccine product was very limited (purity T=0 82.9%, T=3 h 82.2%) confirming the benefits of the compositions described herein.

The invention claimed is:

1. A reconstitution composition for reconstituting dried peptides, comprising: (a) about 60-80% v/v aqueous solution comprising an organic acid at a concentration of 0.05 to 0.25M, wherein the organic acid prevents intermolecular disulfide bond formation at the concentration specified, (b) about 5-10% v/v propylene glycol, (c) about 10-20% v/v lower alcohol, and (d) about 5-10% v/v non-ionic hydrophilic surfactant.

2. The reconstitution composition according to claim 1, wherein the organic acid is citric acid and wherein the citric acid is present in the aqueous solution in a concentration of about 0.05-0.1M.

3. The reconstitution composition according to claim 1, wherein the lower alcohol is ethanol.

4. The reconstitution composition according to claim 1, wherein the non-ionic hydrophilic surfactant:
   (i) is a mono-, di or triglyceride, and/or
   (ii) has a hydrophilic-lipophilic balance (HLB) value between 9 and 14.

5. The reconstitution composition according to claim 4, wherein the triglyceride is an ethoxylated triglyceride.

6. The reconstitution composition according to claim 1, wherein the non-ionic hydrophylic surfactant is ethoxylated castor oil.

7. The reconstitution composition according to claim 6, wherein the ethoxylated castor oil is polyoxyethyleneglyceroltriricinoleate 35.

8. The reconstitution composition according to claim 1, comprising:
   (a) about 75% v/v aqueous solution comprising about 0.1M citric acid,
   (b) about 6.25% v/v propylene glycol,
   (c) about 12.5% v/v ethanol, and
   (d) about 6.25% v/v polyoxyethyleneglyceroltriricinoleate 35.

9. A pharmaceutical composition comprising the reconstitution composition according to claim 1 and peptides between 15 and 100 amino acids in length.

10. The pharmaceutical composition according to claim 9, further comprising an oil-based adjuvant.

11. The pharmaceutical composition according to claim 9, wherein the peptides are derived from a Human Papilloma Virus protein antigen.

12. The pharmaceutical composition according to claim 9, wherein the composition does not comprise any peptides which fulfill both of the following properties:
    (i) the percentage of basic amino acid residues equals the percentage of acidic amino acid residues, and
    (ii) the percentage of hydrophobic amino acid residues is 48% or higher.

13. The pharmaceutical composition according to any claim 9, wherein the peptides comprise contiguous sequences within the HPV immunogenic region E6 and/or E7.

14. The pharmaceutical composition according to claim 13, wherein the contiguous amino acid sequence comprises an epitope comprising a contiguous amino acid sequence selected from the group consisting of the amino acid sequences represented by SEQ ID NO: 20-104.

15. The pharmaceutical composition according to claim 9, wherein the peptides are mixes of peptides that have: at least 2, 3, 4 or 5 of the peptides comprising the sequences selected from SEQ ID NO: 1-5; at least 2, 3, 4, 5 or 6 of the peptides comprising the sequences selected from SEQ ID NO: 1-6; or at least 2, 3, 4, 5, 6 or 7 of the peptides comprising the sequences selected from SEQ ID NO: 7-13.

16. The pharmaceutical composition according to 31, wherein the composition comprises:
    (a) about 1-2 mg/mL peptides in about 40-60% v/v of the reconstitution composition, and
    (b) about 40-60% v/v of Montanide ISA 51VG,
    wherein the peptides are a mixture of different peptides represented by SEQ ID NO: 1-5 or SEQ ID NO: 1-6 or SEQ ID NO: 7-13.

17. The pharmaceutical composition according to claim 9, wherein the peptides consist of a mixture of the 5 different peptides represented by SEQ ID NO:1-5 or a mixture of the 7 different peptides represented by SEQ ID NO:7-13.

18. The pharmaceutical composition according to claim 9, wherein the peptides:

(i) comprise an amino acid sequence selected from SEQ ID NO: 109-146, or (ii) comprise an amino acid sequence selected from SEQ ID NO: 148-167, or are a mix of at least 2, 3, 4, 5, 6, 7, 8, 9, 10, 11, 12, 13, 14, 15, 16, 17, 18, 19 or 20 different peptides selected from SEQ ID NO: 148-167, (iii) comprises a Th epitope that is selected from SEQ ID NO: 168-169, or (iv) comprise a peptide selected from SEQ ID NO: 191-211, or are a mix of at least 2, 3, 4, 5, 6, 7, 8, 9, 10, 11, 12, 13, 14, 15, 16, 17, 18, 19, 20 or 21 different peptides selected from SEQ ID NO: 191-211, or (v) comprise a peptide selected from SEQ ID NO: 213-232, or are a mix of at least 2, 3, 4, 5, 6, 7, 8, 9, 10, 11, 12, 13, 14, 15, 16, 17, 18, 19 or 20 different peptides selected from SEQ ID NO: 213-232.

19. A method for reconstituting dried, optionally lyophilized, peptides, comprising:

(a) providing a vial comprising dried, optionally lyophilized, peptides between 15 and 100 amino acids in length;

(b) thawing the peptides;

(c) adding the reconstitution composition according to claim 1 to the vial comprising the peptides;

(d) allowing to admix; and (e) swirling the admix until a clear solution is obtained.

20. A method for preparing a pharmaceutical composition, comprising:

(a) collecting reconstituted peptides obtainable by the method of claim 19 in a first syringe;

(b) connecting the first syringe of step (a) to a second syringe comprising an oil-based adjuvant using a connector;

(c) pushing and pulling the contents of the first syringe into the second syringe; and (d) repeating step (c) about 10-50 times in a total in about 10-50 seconds.

21. A kit of parts comprising:

(a) a first vial containing dried, optionally lyophilized, peptides between 15 and 100 amino acids in length;

(b) a second vial containing a composition according to claim 1; and optionally, (c) a third vial containing an oil-based adjuvant.

22. The reconstitution composition according to claim 1, wherein the organic acid has a pKa between 1 and 4.

* * * * *

SEQUENCE LISTING

```
<160> NUMBER OF SEQ ID NOS: 232

<210> SEQ ID NO 1
<211> LENGTH: 25
<212> TYPE: PRT
<213> ORGANISM: Artificial
<220> FEATURE:
<223> OTHER INFORMATION: peptide

<400> SEQUENCE: 1

Asp Lys Cys Leu Lys Phe Tyr Ser Lys Ile Ser Glu Tyr Arg His Tyr
1               5                   10                  15

Cys Tyr Ser Leu Tyr Gly Thr Thr Leu
            20                  25

<210> SEQ ID NO 2
<211> LENGTH: 35
<212> TYPE: PRT
<213> ORGANISM: Artificial
<220> FEATURE:
<223> OTHER INFORMATION: peptide

<400> SEQUENCE: 2

Leu Tyr Cys Tyr Glu Gln Leu Asn Asp Ser Ser Glu Glu Glu Asp Glu
1               5                   10                  15

Ile Asp Gly Pro Ala Gly Gln Ala Glu Pro Asp Arg Ala His Tyr Asn
            20                  25                  30

Ile Val Thr
        35

<210> SEQ ID NO 3
<211> LENGTH: 35
<212> TYPE: PRT
<213> ORGANISM: Artificial
<220> FEATURE:
<223> OTHER INFORMATION: peptide

<400> SEQUENCE: 3

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu
        35
```

```
<210> SEQ ID NO 4
<211> LENGTH: 32
<212> TYPE: PRT
<213> ORGANISM: Artificial
<220> FEATURE:
<223> OTHER INFORMATION: peptide

<400> SEQUENCE: 4

Arg Cys Ile Asn Cys Gln Lys Pro Leu Cys Pro Glu Glu Lys Gln Arg
1               5                   10                  15

His Leu Asp Lys Lys Gln Arg Phe His Asn Ile Arg Gly Arg Trp Thr
            20                  25                  30

<210> SEQ ID NO 5
<211> LENGTH: 35
<212> TYPE: PRT
<213> ORGANISM: Artificial
<220> FEATURE:
<223> OTHER INFORMATION: peptide

<400> SEQUENCE: 5

Thr Leu Arg Leu Cys Val Gln Ser Thr His Val Asp Ile Arg Thr Leu
1               5                   10                  15

Glu Asp Leu Leu Met Gly Thr Leu Gly Ile Val Cys Pro Ile Cys Ser
            20                  25                  30

Gln Lys Pro
        35

<210> SEQ ID NO 6
<211> LENGTH: 35
<212> TYPE: PRT
<213> ORGANISM: Artificial
<220> FEATURE:
<223> OTHER INFORMATION: peptide

<400> SEQUENCE: 6

Gly Gln Ala Glu Pro Asp Arg Ala His Tyr Asn Ile Val Thr Phe Cys
1               5                   10                  15

Cys Lys Cys Asp Ser Thr Leu Arg Leu Cys Val Gln Ser Thr His Val
            20                  25                  30

Asp Ile Arg
        35

<210> SEQ ID NO 7
<211> LENGTH: 32
<212> TYPE: PRT
<213> ORGANISM: Artificial
<220> FEATURE:
<223> OTHER INFORMATION: peptide

<400> SEQUENCE: 7

Asp Lys Lys Gln Arg Phe His Asn Ile Arg Gly Arg Trp Thr Gly Arg
1               5                   10                  15

Cys Met Ser Cys Cys Arg Ser Ser Arg Thr Arg Glu Thr Gln Leu
            20                  25                  30

<210> SEQ ID NO 8
<211> LENGTH: 25
<212> TYPE: PRT
<213> ORGANISM: Artificial
<220> FEATURE:
<223> OTHER INFORMATION: peptide

<400> SEQUENCE: 8
```

His Tyr Cys Tyr Ser Leu Tyr Gly Thr Thr Leu Glu Gln Gln Tyr Asn
1               5                   10                  15

Lys Pro Leu Cys Asp Leu Leu Ile Arg
            20                  25

<210> SEQ ID NO 9
<211> LENGTH: 25
<212> TYPE: PRT
<213> ORGANISM: Artificial
<220> FEATURE:
<223> OTHER INFORMATION: peptide

<400> SEQUENCE: 9

Lys Gln Gln Leu Leu Arg Arg Glu Val Tyr Asp Phe Ala Phe Arg Asp
1               5                   10                  15

Leu Cys Ile Val Tyr Arg Asp Gly Asn
            20                  25

<210> SEQ ID NO 10
<211> LENGTH: 32
<212> TYPE: PRT
<213> ORGANISM: Artificial
<220> FEATURE:
<223> OTHER INFORMATION: peptide

<400> SEQUENCE: 10

Leu Pro Gln Leu Cys Thr Glu Leu Gln Thr Thr Ile His Asp Ile Ile
1               5                   10                  15

Leu Glu Cys Val Tyr Cys Lys Gln Gln Leu Leu Arg Arg Glu Val Tyr
            20                  25                  30

<210> SEQ ID NO 11
<211> LENGTH: 32
<212> TYPE: PRT
<213> ORGANISM: Artificial
<220> FEATURE:
<223> OTHER INFORMATION: peptide

<400> SEQUENCE: 11

Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
            20                  25                  30

<210> SEQ ID NO 12
<211> LENGTH: 26
<212> TYPE: PRT
<213> ORGANISM: Artificial
<220> FEATURE:
<223> OTHER INFORMATION: peptide

<400> SEQUENCE: 12

Arg Asp Leu Cys Ile Val Tyr Arg Asp Gly Asn Pro Tyr Ala Val Cys
1               5                   10                  15

Asp Lys Cys Leu Lys Phe Tyr Ser Lys Ile
            20                  25

<210> SEQ ID NO 13
<211> LENGTH: 32
<212> TYPE: PRT
<213> ORGANISM: Artificial
<220> FEATURE:
<223> OTHER INFORMATION: peptide

<400> SEQUENCE: 13

Tyr Gly Thr Thr Leu Glu Gln Gln Tyr Asn Lys Pro Leu Cys Asp Leu
1               5                   10                  15

Leu Ile Arg Cys Ile Asn Cys Gln Lys Pro Leu Cys Pro Glu Glu Lys
            20                  25                  30

<210> SEQ ID NO 14
<211> LENGTH: 365
<212> TYPE: PRT
<213> ORGANISM: Human papillomavirus type 16

<400> SEQUENCE: 14

Met Glu Thr Leu Cys Gln Arg Leu Asn Val Cys Gln Asp Lys Ile Leu
1               5                   10                  15

Thr His Tyr Glu Asn Asp Ser Thr Asp Leu Arg Asp His Ile Asp Tyr
            20                  25                  30

Trp Lys His Met Arg Leu Glu Cys Ala Ile Tyr Tyr Lys Ala Arg Glu
        35                  40                  45

Met Gly Phe Lys His Ile Asn His Gln Val Val Pro Thr Leu Ala Val
    50                  55                  60

Ser Lys Asn Lys Ala Leu Gln Ala Ile Glu Leu Gln Leu Thr Leu Glu
65                  70                  75                  80

Thr Ile Tyr Asn Ser Gln Tyr Ser Asn Glu Lys Trp Thr Leu Gln Asp
                85                  90                  95

Val Ser Leu Glu Val Tyr Leu Thr Ala Pro Thr Gly Cys Ile Lys Lys
            100                 105                 110

His Gly Tyr Thr Val Glu Val Gln Phe Asp Gly Asp Ile Cys Asn Thr
        115                 120                 125

Met His Tyr Thr Asn Trp Thr His Ile Tyr Ile Cys Glu Glu Ala Ser
    130                 135                 140

Val Thr Val Val Glu Gly Gln Val Asp Tyr Tyr Gly Leu Tyr Tyr Val
145                 150                 155                 160

His Glu Gly Ile Arg Thr Tyr Phe Val Gln Phe Lys Asp Asp Ala Glu
                165                 170                 175

Lys Tyr Ser Lys Asn Lys Val Trp Glu Val His Ala Gly Gly Gln Val
            180                 185                 190

Ile Leu Cys Pro Thr Ser Val Phe Ser Ser Asn Glu Val Ser Ser Pro
        195                 200                 205

Glu Ile Ile Arg Gln His Leu Ala Asn His Pro Ala Ala Thr His Thr
    210                 215                 220

Lys Ala Val Ala Leu Gly Thr Glu Glu Thr Gln Thr Thr Ile Gln Arg
225                 230                 235                 240

Pro Arg Ser Glu Pro Asp Thr Gly Asn Pro Cys His Thr Thr Lys Leu
                245                 250                 255

Leu His Arg Asp Ser Val Asp Ser Ala Pro Ile Leu Thr Ala Phe Asn
            260                 265                 270

Ser Ser His Lys Gly Arg Ile Asn Cys Asn Ser Asn Thr Thr Pro Ile
        275                 280                 285

Val His Leu Lys Gly Asp Ala Asn Thr Leu Lys Cys Leu Arg Tyr Arg
    290                 295                 300

Phe Lys Lys His Cys Thr Leu Tyr Thr Ala Val Ser Ser Thr Trp His
305                 310                 315                 320

Trp Thr Gly His Asn Val Lys His Lys Ser Ala Ile Val Thr Leu Thr
                325                 330                 335

Tyr Asp Ser Glu Trp Gln Arg Asp Gln Phe Leu Ser Gln Val Lys Ile

```
                340                 345                 350
Pro Lys Thr Ile Thr Val Ser Thr Gly Phe Met Ser Ile
        355                 360                 365

<210> SEQ ID NO 15
<211> LENGTH: 158
<212> TYPE: PRT
<213> ORGANISM: Human papillomavirus type 16

<400> SEQUENCE: 15

Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
        35                  40                  45

Val Tyr Asp Phe Ala Phe Arg Asp Leu Cys Ile Val Tyr Arg Asp Gly
    50                  55                  60

Asn Pro Tyr Ala Val Cys Asp Lys Cys Leu Lys Phe Tyr Ser Lys Ile
65                  70                  75                  80

Ser Glu Tyr Arg His Tyr Cys Tyr Ser Leu Tyr Gly Thr Thr Leu Glu
                85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu Glu Lys Gln Arg His Leu Asp Lys
        115                 120                 125

Lys Gln Arg Phe His Asn Ile Arg Gly Arg Trp Thr Gly Arg Cys Met
    130                 135                 140

Ser Cys Cys Arg Ser Ser Arg Thr Arg Arg Glu Thr Gln Leu
145                 150                 155

<210> SEQ ID NO 16
<211> LENGTH: 98
<212> TYPE: PRT
<213> ORGANISM: Human papillomavirus type 16

<400> SEQUENCE: 16

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 17
<211> LENGTH: 365
<212> TYPE: PRT
<213> ORGANISM: Human papillomavirus type 18

<400> SEQUENCE: 17
```

```
Met Gln Thr Pro Lys Glu Thr Leu Ser Glu Arg Leu Ser Cys Val Gln
1               5                   10                  15

Asp Lys Ile Ile Asp His Tyr Glu Asn Asp Ser Lys Asp Ile Asp Ser
            20                  25                  30

Gln Ile Gln Tyr Trp Gln Leu Ile Arg Trp Glu Asn Ala Ile Phe Phe
        35                  40                  45

Ala Ala Arg Glu His Gly Ile Gln Thr Leu Asn His Gln Val Val Pro
    50                  55                  60

Ala Tyr Asn Ile Ser Ser Lys Ala His Lys Ala Ile Glu Leu Gln
65                  70                  75                  80

Met Ala Leu Gln Gly Leu Ala Gln Ser Ala Tyr Lys Thr Glu Asp Trp
                85                  90                  95

Thr Leu Gln Asp Thr Cys Glu Glu Leu Trp Asn Thr Glu Pro Thr His
                100                 105                 110

Cys Phe Lys Lys Gly Gly Gln Thr Val Gln Val Tyr Phe Asp Gly Asn
                115                 120                 125

Lys Asp Asn Cys Met Thr Tyr Val Ala Trp Asp Ser Val Tyr Tyr Met
        130                 135                 140

Thr Asp Ala Gly Thr Trp Asp Lys Thr Ala Thr Cys Val Ser His Arg
145                 150                 155                 160

Gly Leu Tyr Tyr Val Lys Glu Gly Tyr Asn Thr Phe Tyr Ile Glu Phe
                165                 170                 175

Lys Ser Glu Cys Glu Lys Tyr Gly Asn Thr Gly Thr Trp Glu Val His
                180                 185                 190

Phe Gly Asn Asn Val Ile Asp Cys Asn Asp Ser Met Cys Ser Thr Ser
            195                 200                 205

Asp Asp Thr Val Ser Ala Thr Gln Leu Val Lys Gln Leu Gln His Thr
        210                 215                 220

Pro Ser Pro Tyr Ser Ser Thr Val Ser Val Gly Thr Ala Lys Thr Tyr
225                 230                 235                 240

Gly Gln Thr Ser Ala Ala Thr Arg Pro Gly His Cys Gly Leu Ala Glu
                245                 250                 255

Lys Gln His Cys Gly Pro Val Asn Pro Leu Leu Gly Ala Ala Thr Pro
                260                 265                 270

Thr Gly Asn Asn Lys Arg Arg Lys Leu Cys Ser Gly Asn Thr Thr Pro
                275                 280                 285

Ile Ile His Leu Lys Gly Asp Arg Asn Ser Leu Lys Cys Leu Arg Tyr
            290                 295                 300

Arg Leu Arg Lys His Ser Asp His Tyr Arg Asp Ile Ser Ser Thr Trp
305                 310                 315                 320

His Trp Thr Gly Ala Gly Asn Glu Lys Thr Gly Ile Leu Thr Val Thr
                325                 330                 335

Tyr His Ser Glu Thr Gln Arg Thr Lys Phe Leu Asn Thr Val Ala Ile
                340                 345                 350

Pro Asp Ser Val Gln Ile Leu Val Gly Tyr Met Thr Met
            355                 360                 365

<210> SEQ ID NO 18
<211> LENGTH: 158
<212> TYPE: PRT
<213> ORGANISM: Human papillomavirus type 18

<400> SEQUENCE: 18

Met Ala Arg Phe Glu Asp Pro Thr Arg Arg Pro Tyr Lys Leu Pro Asp
1               5                   10                  15
```

```
Leu Cys Thr Glu Leu Asn Thr Ser Leu Gln Asp Ile Glu Ile Thr Cys
            20                  25                  30

Val Tyr Cys Lys Thr Val Leu Glu Leu Thr Glu Val Phe Glu Phe Ala
        35                  40                  45

Phe Lys Asp Leu Phe Val Val Tyr Arg Asp Ser Ile Pro His Ala Ala
50                  55                  60

Cys His Lys Cys Ile Asp Phe Tyr Ser Arg Ile Arg Glu Leu Arg His
65                  70                  75                  80

Tyr Ser Asp Ser Val Tyr Gly Asp Thr Leu Glu Lys Leu Thr Asn Thr
                85                  90                  95

Gly Leu Tyr Asn Leu Leu Ile Arg Cys Leu Arg Cys Gln Lys Pro Leu
            100                 105                 110

Asn Pro Ala Glu Lys Leu Arg His Leu Asn Glu Lys Arg Arg Phe His
        115                 120                 125

Asn Ile Ala Gly His Tyr Arg Gly Gln Cys His Ser Cys Cys Asn Arg
    130                 135                 140

Ala Arg Gln Glu Arg Leu Gln Arg Arg Arg Glu Thr Gln Val
145                 150                 155

<210> SEQ ID NO 19
<211> LENGTH: 105
<212> TYPE: PRT
<213> ORGANISM: Human papillomavirus type 18

<400> SEQUENCE: 19

Met His Gly Pro Lys Ala Thr Leu Gln Asp Ile Val Leu His Leu Glu
1               5                   10                  15

Pro Gln Asn Glu Ile Pro Val Asp Leu Leu Cys His Glu Gln Leu Ser
            20                  25                  30

Asp Ser Glu Glu Glu Asn Asp Glu Ile Asp Gly Val Asn His Gln His
        35                  40                  45

Leu Pro Ala Arg Arg Ala Glu Pro Gln Arg His Thr Met Leu Cys Met
50                  55                  60

Cys Cys Lys Cys Glu Ala Arg Ile Lys Leu Val Val Glu Ser Ser Ala
65                  70                  75                  80

Asp Asp Leu Arg Ala Phe Gln Gln Leu Phe Leu Asn Thr Leu Ser Phe
                85                  90                  95

Val Cys Pro Trp Cys Ala Ser Gln Gln
            100                 105

<210> SEQ ID NO 20
<211> LENGTH: 30
<212> TYPE: PRT
<213> ORGANISM: Artificial
<220> FEATURE:
<223> OTHER INFORMATION: peptide

<400> SEQUENCE: 20

Arg Pro Arg Lys Leu Pro Gln Leu Cys Thr Glu Leu Gln Thr Thr Ile
1               5                   10                  15

His Asp Ile Ile Leu Glu Cys Val Tyr Cys Lys Gln Gln Leu
            20                  25                  30

<210> SEQ ID NO 21
<211> LENGTH: 22
<212> TYPE: PRT
<213> ORGANISM: Artificial
<220> FEATURE:
```

<223> OTHER INFORMATION: peptide

<400> SEQUENCE: 21

Arg Arg Glu Val Tyr Asp Phe Ala Phe Arg Asp Leu Cys Ile Val Tyr
1               5                   10                  15

Arg Asp Gly Asn Pro Tyr
            20

<210> SEQ ID NO 22
<211> LENGTH: 29
<212> TYPE: PRT
<213> ORGANISM: Artificial
<220> FEATURE:
<223> OTHER INFORMATION: peptide

<400> SEQUENCE: 22

Ile Ser Glu Tyr Arg His Tyr Cys Tyr Ser Leu Tyr Gly Thr Thr Leu
1               5                   10                  15

Glu Gln Gln Tyr Asn Lys Pro Leu Cys Asp Leu Leu Ile
            20                  25

<210> SEQ ID NO 23
<211> LENGTH: 32
<212> TYPE: PRT
<213> ORGANISM: Artificial
<220> FEATURE:
<223> OTHER INFORMATION: peptide

<400> SEQUENCE: 23

Ile Arg Cys Ile Asn Cys Gln Lys Pro Leu Cys Pro Glu Glu Lys Gln
1               5                   10                  15

Arg His Leu Asp Lys Lys Gln Arg Phe His Asn Ile Arg Gly Arg Trp
            20                  25                  30

<210> SEQ ID NO 24
<211> LENGTH: 23
<212> TYPE: PRT
<213> ORGANISM: Artificial
<220> FEATURE:
<223> OTHER INFORMATION: peptide

<400> SEQUENCE: 24

Gly Asp Thr Pro Thr Leu His Glu Tyr Met Leu Asp Leu Gln Pro Glu
1               5                   10                  15

Thr Thr Asp Leu Tyr Cys Tyr
            20

<210> SEQ ID NO 25
<211> LENGTH: 17
<212> TYPE: PRT
<213> ORGANISM: Artificial
<220> FEATURE:
<223> OTHER INFORMATION: peptide

<400> SEQUENCE: 25

Gln Ala Glu Pro Asp Arg Ala His Tyr Asn Ile Val Thr Phe Cys Cys
1               5                   10                  15

Lys

<210> SEQ ID NO 26
<211> LENGTH: 19
<212> TYPE: PRT
<213> ORGANISM: Artificial
<220> FEATURE:

<223> OTHER INFORMATION: peptide

<400> SEQUENCE: 26

Leu Glu Asp Leu Leu Met Gly Thr Leu Gly Ile Val Cys Pro Ile Cys
1               5                   10                  15

Ser Gln Lys

<210> SEQ ID NO 27
<211> LENGTH: 8
<212> TYPE: PRT
<213> ORGANISM: Artificial
<220> FEATURE:
<223> OTHER INFORMATION: peptide

<400> SEQUENCE: 27

Arg Pro Arg Lys Leu Pro Gln Leu
1               5

<210> SEQ ID NO 28
<211> LENGTH: 9
<212> TYPE: PRT
<213> ORGANISM: Artificial
<220> FEATURE:
<223> OTHER INFORMATION: peptide

<400> SEQUENCE: 28

Lys Leu Pro Gln Leu Cys Thr Glu Leu
1               5

<210> SEQ ID NO 29
<211> LENGTH: 8
<212> TYPE: PRT
<213> ORGANISM: Artificial
<220> FEATURE:
<223> OTHER INFORMATION: peptide

<400> SEQUENCE: 29

Leu Pro Gln Leu Cys Thr Glu Leu
1               5

<210> SEQ ID NO 30
<211> LENGTH: 10
<212> TYPE: PRT
<213> ORGANISM: Artificial
<220> FEATURE:
<223> OTHER INFORMATION: peptide

<400> SEQUENCE: 30

Gln Leu Cys Thr Glu Leu Gln Thr Thr Ile
1               5                   10

<210> SEQ ID NO 31
<211> LENGTH: 10
<212> TYPE: PRT
<213> ORGANISM: Artificial
<220> FEATURE:
<223> OTHER INFORMATION: peptide

<400> SEQUENCE: 31

Thr Glu Leu Gln Thr Thr Ile His Asp Ile
1               5                   10

<210> SEQ ID NO 32
<211> LENGTH: 10
<212> TYPE: PRT
<213> ORGANISM: Artificial

```
<220> FEATURE:
<223> OTHER INFORMATION: peptide

<400> SEQUENCE: 32

Thr Ile His Asp Ile Ile Leu Arg Cys Val
1               5                   10

<210> SEQ ID NO 33
<211> LENGTH: 9
<212> TYPE: PRT
<213> ORGANISM: Artificial
<220> FEATURE:
<223> OTHER INFORMATION: peptide

<400> SEQUENCE: 33

Ile Ile Leu Glu Cys Val Tyr Cys Lys
1               5

<210> SEQ ID NO 34
<211> LENGTH: 10
<212> TYPE: PRT
<213> ORGANISM: Artificial
<220> FEATURE:
<223> OTHER INFORMATION: peptide

<400> SEQUENCE: 34

Leu Glu Cys Val Tyr Cys Lys Gln Gln Leu
1               5                   10

<210> SEQ ID NO 35
<211> LENGTH: 8
<212> TYPE: PRT
<213> ORGANISM: Artificial
<220> FEATURE:
<223> OTHER INFORMATION: peptide

<400> SEQUENCE: 35

Cys Val Tyr Cys Lys Gln Gln Leu
1               5

<210> SEQ ID NO 36
<211> LENGTH: 10
<212> TYPE: PRT
<213> ORGANISM: Artificial
<220> FEATURE:
<223> OTHER INFORMATION: peptide

<400> SEQUENCE: 36

Arg Arg Glu Val Tyr Asp Phe Ala Phe Arg
1               5                   10

<210> SEQ ID NO 37
<211> LENGTH: 9
<212> TYPE: PRT
<213> ORGANISM: Artificial
<220> FEATURE:
<223> OTHER INFORMATION: peptide

<400> SEQUENCE: 37

Val Tyr Asp Phe Ala Phe Arg Asp Leu
1               5

<210> SEQ ID NO 38
<211> LENGTH: 8
<212> TYPE: PRT
<213> ORGANISM: Artificial
<220> FEATURE:
```

```
<223> OTHER INFORMATION: peptide

<400> SEQUENCE: 38

Tyr Asp Phe Ala Phe Arg Asp Leu
1               5

<210> SEQ ID NO 39
<211> LENGTH: 9
<212> TYPE: PRT
<213> ORGANISM: Artificial
<220> FEATURE:
<223> OTHER INFORMATION: peptide

<400> SEQUENCE: 39

Phe Ala Phe Arg Asp Leu Cys Ile Val
1               5

<210> SEQ ID NO 40
<211> LENGTH: 9
<212> TYPE: PRT
<213> ORGANISM: Artificial
<220> FEATURE:
<223> OTHER INFORMATION: peptide

<400> SEQUENCE: 40

Phe Arg Asp Leu Cys Ile Val Tyr Arg
1               5

<210> SEQ ID NO 41
<211> LENGTH: 9
<212> TYPE: PRT
<213> ORGANISM: Artificial
<220> FEATURE:
<223> OTHER INFORMATION: peptide

<400> SEQUENCE: 41

Ile Val Tyr Arg Asp Gly Asn Pro Tyr
1               5

<210> SEQ ID NO 42
<211> LENGTH: 9
<212> TYPE: PRT
<213> ORGANISM: Artificial
<220> FEATURE:
<223> OTHER INFORMATION: peptide

<400> SEQUENCE: 42

Ile Ser Glu Tyr Arg His Tyr Cys Tyr
1               5

<210> SEQ ID NO 43
<211> LENGTH: 8
<212> TYPE: PRT
<213> ORGANISM: Artificial
<220> FEATURE:
<223> OTHER INFORMATION: peptide

<400> SEQUENCE: 43

Ser Glu Tyr Arg His Tyr Cys Tyr
1               5

<210> SEQ ID NO 44
<211> LENGTH: 9
<212> TYPE: PRT
<213> ORGANISM: Artificial
<220> FEATURE:
<223> OTHER INFORMATION: peptide
```

<400> SEQUENCE: 44

Cys Tyr Ser Leu Tyr Gly Thr Thr Leu
1               5

<210> SEQ ID NO 45
<211> LENGTH: 8
<212> TYPE: PRT
<213> ORGANISM: Artificial
<220> FEATURE:
<223> OTHER INFORMATION: peptide

<400> SEQUENCE: 45

Thr Leu Glu Gln Gln Tyr Asn Lys
1               5

<210> SEQ ID NO 46
<211> LENGTH: 9
<212> TYPE: PRT
<213> ORGANISM: Artificial
<220> FEATURE:
<223> OTHER INFORMATION: peptide

<400> SEQUENCE: 46

Leu Glu Gln Gln Tyr Asn Lys Pro Leu
1               5

<210> SEQ ID NO 47
<211> LENGTH: 8
<212> TYPE: PRT
<213> ORGANISM: Artificial
<220> FEATURE:
<223> OTHER INFORMATION: peptide

<400> SEQUENCE: 47

Lys Pro Leu Cys Asp Leu Leu Ile
1               5

<210> SEQ ID NO 48
<211> LENGTH: 9
<212> TYPE: PRT
<213> ORGANISM: Artificial
<220> FEATURE:
<223> OTHER INFORMATION: peptide

<400> SEQUENCE: 48

Cys Pro Glu Glu Lys Gln Arg His Leu
1               5

<210> SEQ ID NO 49
<211> LENGTH: 8
<212> TYPE: PRT
<213> ORGANISM: Artificial
<220> FEATURE:
<223> OTHER INFORMATION: peptide

<400> SEQUENCE: 49

Pro Glu Glu Lys Gln Arg His Leu
1               5

<210> SEQ ID NO 50
<211> LENGTH: 7
<212> TYPE: PRT
<213> ORGANISM: Artificial
<220> FEATURE:
<223> OTHER INFORMATION: peptide

<400> SEQUENCE: 50

Asp Lys Lys Gln Arg His Met
1               5

<210> SEQ ID NO 51
<211> LENGTH: 9
<212> TYPE: PRT
<213> ORGANISM: Artificial
<220> FEATURE:
<223> OTHER INFORMATION: peptide

<400> SEQUENCE: 51

Lys Lys Gln Arg Phe His Asn Ile Arg
1               5

<210> SEQ ID NO 52
<211> LENGTH: 10
<212> TYPE: PRT
<213> ORGANISM: Artificial
<220> FEATURE:
<223> OTHER INFORMATION: peptide

<400> SEQUENCE: 52

Gln Arg Phe His Asn Ile Arg Gly Arg Trp
1               5                   10

<210> SEQ ID NO 53
<211> LENGTH: 9
<212> TYPE: PRT
<213> ORGANISM: Artificial
<220> FEATURE:
<223> OTHER INFORMATION: peptide

<400> SEQUENCE: 53

Arg Phe His Asn Ile Arg Gly Arg Trp
1               5

<210> SEQ ID NO 54
<211> LENGTH: 9
<212> TYPE: PRT
<213> ORGANISM: Artificial
<220> FEATURE:
<223> OTHER INFORMATION: peptide

<400> SEQUENCE: 54

Gly Asp Thr Pro Thr Leu His Glu Tyr
1               5

<210> SEQ ID NO 55
<211> LENGTH: 9
<212> TYPE: PRT
<213> ORGANISM: Artificial
<220> FEATURE:
<223> OTHER INFORMATION: peptide

<400> SEQUENCE: 55

Thr Pro Thr Leu His Glu Tyr Met Leu
1               5

<210> SEQ ID NO 56
<211> LENGTH: 10
<212> TYPE: PRT
<213> ORGANISM: Artificial
<220> FEATURE:
<223> OTHER INFORMATION: peptide

<400> SEQUENCE: 56

```
Tyr Met Leu Asp Leu Gln Pro Glu Thr Thr
1               5                   10
```

<210> SEQ ID NO 57
<211> LENGTH: 9
<212> TYPE: PRT
<213> ORGANISM: Artificial
<220> FEATURE:
<223> OTHER INFORMATION: peptide

<400> SEQUENCE: 57

```
Leu Gln Pro Glu Thr Thr Asp Leu Tyr
1               5
```

<210> SEQ ID NO 58
<211> LENGTH: 10
<212> TYPE: PRT
<213> ORGANISM: Artificial
<220> FEATURE:
<223> OTHER INFORMATION: peptide

<400> SEQUENCE: 58

```
Gln Pro Glu Thr Thr Asp Leu Tyr Cys Tyr
1               5                   10
```

<210> SEQ ID NO 59
<211> LENGTH: 9
<212> TYPE: PRT
<213> ORGANISM: Artificial
<220> FEATURE:
<223> OTHER INFORMATION: peptide

<400> SEQUENCE: 59

```
Gln Ala Glu Pro Asp Arg Ala His Tyr
1               5
```

<210> SEQ ID NO 60
<211> LENGTH: 8
<212> TYPE: PRT
<213> ORGANISM: Artificial
<220> FEATURE:
<223> OTHER INFORMATION: peptide

<400> SEQUENCE: 60

```
Ala Glu Pro Asp Arg Ala His Tyr
1               5
```

<210> SEQ ID NO 61
<211> LENGTH: 10
<212> TYPE: PRT
<213> ORGANISM: Artificial
<220> FEATURE:
<223> OTHER INFORMATION: peptide

<400> SEQUENCE: 61

```
Glu Pro Asp Arg Ala His Tyr Asn Ile Val
1               5                   10
```

<210> SEQ ID NO 62
<211> LENGTH: 7
<212> TYPE: PRT
<213> ORGANISM: Artificial
<220> FEATURE:
<223> OTHER INFORMATION: peptide

<400> SEQUENCE: 62

```
Met Val Thr Phe Cys Cys Lys
1               5
```

<210> SEQ ID NO 63
<211> LENGTH: 9
<212> TYPE: PRT
<213> ORGANISM: Artificial
<220> FEATURE:
<223> OTHER INFORMATION: peptide

<400> SEQUENCE: 63

```
Leu Glu Asp Leu Leu Met Gly Thr Leu
1               5
```

<210> SEQ ID NO 64
<211> LENGTH: 9
<212> TYPE: PRT
<213> ORGANISM: Artificial
<220> FEATURE:
<223> OTHER INFORMATION: peptide

<400> SEQUENCE: 64

```
Leu Leu Met Gly Thr Leu Gly Ile Val
1               5
```

<210> SEQ ID NO 65
<211> LENGTH: 8
<212> TYPE: PRT
<213> ORGANISM: Artificial
<220> FEATURE:
<223> OTHER INFORMATION: peptide

<400> SEQUENCE: 65

```
Thr Leu Gly Ile Val Cys Pro Ile
1               5
```

<210> SEQ ID NO 66
<211> LENGTH: 9
<212> TYPE: PRT
<213> ORGANISM: Artificial
<220> FEATURE:
<223> OTHER INFORMATION: peptide

<400> SEQUENCE: 66

```
Ile Val Cys Pro Ile Cys Ser Gln Lys
1               5
```

<210> SEQ ID NO 67
<211> LENGTH: 9
<212> TYPE: PRT
<213> ORGANISM: Artificial
<220> FEATURE:
<223> OTHER INFORMATION: peptide

<400> SEQUENCE: 67

```
Arg Ala His Tyr Asn Ile Val Thr Phe
1               5
```

<210> SEQ ID NO 68
<211> LENGTH: 90
<212> TYPE: PRT
<213> ORGANISM: Artificial
<220> FEATURE:
<223> OTHER INFORMATION: peptide

<400> SEQUENCE: 68

Asp Tyr Trp Lys His Met Arg Leu Glu Cys Ala Ile Tyr Tyr Lys Ala

```
                1               5                  10                  15
            Arg Glu Met Gly Phe Lys His Ile Asn His Gln Val Val Pro Thr Leu
                            20                  25                  30

Ala Val Ser Lys Asn Lys Ala Leu Gln Ala Ile Glu Leu Gln Leu Thr
                            35                  40                  45

Leu Glu Thr Ile Tyr Asn Ser Gln Tyr Ser Asn Glu Lys Trp Thr Leu
                            50                  55                  60

Gln Asp Val Ser Leu Glu Val Tyr Leu Thr Ala Pro Thr Gly Cys Ile
            65                  70                  75                  80

Lys Lys His Gly Tyr Thr Val Glu Val Gln
                            85                  90
```

<210> SEQ ID NO 69
<211> LENGTH: 45
<212> TYPE: PRT
<213> ORGANISM: Artificial
<220> FEATURE:
<223> OTHER INFORMATION: peptide

<400> SEQUENCE: 69

```
            Gln Val Asp Tyr Tyr Gly Leu Tyr Tyr Val His Glu Gly Ile Arg Thr
            1               5                  10                  15

Tyr Phe Val Gln Phe Lys Asp Asp Ala Glu Lys Tyr Ser Lys Asn Lys
                            20                  25                  30

Val Trp Glu Val His Ala Gly Gly Gln Val Ile Leu Cys
                            35                  40                  45
```

<210> SEQ ID NO 70
<211> LENGTH: 95
<212> TYPE: PRT
<213> ORGANISM: Artificial
<220> FEATURE:
<223> OTHER INFORMATION: peptide

<400> SEQUENCE: 70

```
            Phe Asn Ser Ser His Lys Gly Arg Ile Asn Cys Asn Ser Asn Thr Thr
            1               5                  10                  15

Pro Ile Val His Leu Lys Gly Asp Ala Asn Thr Leu Lys Cys Leu Arg
                            20                  25                  30

Tyr Arg Phe Lys Lys His Cys Thr Leu Tyr Thr Ala Val Ser Ser Thr
                            35                  40                  45

Trp His Trp Thr Gly His Asn Val Lys His Lys Ser Ala Ile Val Thr
                            50                  55                  60

Leu Thr Tyr Asp Ser Glu Trp Gln Arg Asp Gln Phe Leu Ser Gln Val
            65                  70                  75                  80

Lys Ile Pro Lys Thr Ile Thr Val Ser Thr Gly Phe Met Ser Ile
                            85                  90                  95
```

<210> SEQ ID NO 71
<211> LENGTH: 78
<212> TYPE: PRT
<213> ORGANISM: Artificial
<220> FEATURE:
<223> OTHER INFORMATION: peptide

<400> SEQUENCE: 71

```
            Ser Glu Tyr Arg His Tyr Cys Tyr Ser Leu Tyr Gly Thr Thr Leu Glu
            1               5                  10                  15

Gln Gln Tyr Asn Lys Pro Leu Cys Asp Leu Leu Ile Arg Cys Ile Asn
                            20                  25                  30
```

Cys Gln Lys Pro Leu Cys Pro Glu Glu Lys Gln Arg His Leu Asp Lys
            35                  40                  45

Lys Gln Arg Phe His Asn Ile Arg Gly Arg Trp Thr Gly Arg Cys Met
    50                  55                  60

Ser Cys Cys Arg Ser Ser Arg Thr Arg Arg Glu Thr Gln Leu
65                  70                  75

<210> SEQ ID NO 72
<211> LENGTH: 47
<212> TYPE: PRT
<213> ORGANISM: Artificial
<220> FEATURE:
<223> OTHER INFORMATION: peptide

<400> SEQUENCE: 72

Ser Ser Glu Glu Glu Asp Glu Ile Asp Gly Pro Ala Gly Gln Ala Glu
1               5                   10                  15

Pro Asp Arg Ala His Tyr Asn Ile Val Thr Phe Cys Cys Lys Cys Asp
                20                  25                  30

Ser Thr Leu Arg Leu Cys Val Gln Ser Thr His Val Asp Ile Arg
            35                  40                  45

<210> SEQ ID NO 73
<211> LENGTH: 15
<212> TYPE: PRT
<213> ORGANISM: Artificial
<220> FEATURE:
<223> OTHER INFORMATION: peptide

<400> SEQUENCE: 73

Lys Ile Pro Lys Thr Ile Thr Val Ser Thr Gly Phe Met Ser Ile
1               5                   10                  15

<210> SEQ ID NO 74
<211> LENGTH: 15
<212> TYPE: PRT
<213> ORGANISM: Artificial
<220> FEATURE:
<223> OTHER INFORMATION: peptide

<400> SEQUENCE: 74

Ser Ser Thr Trp His Trp Thr Gly His Asn Val Lys His Lys Ser
1               5                   10                  15

<210> SEQ ID NO 75
<211> LENGTH: 10
<212> TYPE: PRT
<213> ORGANISM: Artificial
<220> FEATURE:
<223> OTHER INFORMATION: peptide

<400> SEQUENCE: 75

Phe Leu Ser Gln Val Lys Ile Pro Lys Thr
1               5                   10

<210> SEQ ID NO 76
<211> LENGTH: 20
<212> TYPE: PRT
<213> ORGANISM: Artificial
<220> FEATURE:
<223> OTHER INFORMATION: peptide

<400> SEQUENCE: 76

Phe Lys His Ile Asn His Gln Val Val Pro Thr Leu Ala Val Ser Lys

Asn Lys Ala Leu
            20

<210> SEQ ID NO 77
<211> LENGTH: 16
<212> TYPE: PRT
<213> ORGANISM: Artificial
<220> FEATURE:
<223> OTHER INFORMATION: peptide

<400> SEQUENCE: 77

Thr Leu Ala Val Ser Lys Asn Lys Ala Leu Gln Ala Ile Glu Leu Gln
1               5                   10                  15

<210> SEQ ID NO 78
<211> LENGTH: 15
<212> TYPE: PRT
<213> ORGANISM: Artificial
<220> FEATURE:
<223> OTHER INFORMATION: peptide

<400> SEQUENCE: 78

Leu Tyr Thr Ala Val Ser Ser Thr Trp His Trp Thr Gly His Asn
1               5                   10                  15

<210> SEQ ID NO 79
<211> LENGTH: 13
<212> TYPE: PRT
<213> ORGANISM: Artificial
<220> FEATURE:
<223> OTHER INFORMATION: peptide

<400> SEQUENCE: 79

Ala His Tyr Asn Ile Val Thr Phe Cys Cys Lys Cys Asp
1               5                   10

<210> SEQ ID NO 80
<211> LENGTH: 35
<212> TYPE: PRT
<213> ORGANISM: Artificial
<220> FEATURE:
<223> OTHER INFORMATION: peptide

<400> SEQUENCE: 80

Gly Gln Ala Glu Pro Asp Arg Ala His Tyr Asn Ile Val Thr Phe Cys
1               5                   10                  15

Cys Lys Cys Asp Ser Thr Leu Arg Leu Cys Val Gln Ser Thr His Val
            20                  25                  30

Asp Ile Arg
        35

<210> SEQ ID NO 81
<211> LENGTH: 16
<212> TYPE: PRT
<213> ORGANISM: Artificial
<220> FEATURE:
<223> OTHER INFORMATION: peptide

<400> SEQUENCE: 81

Glu Asp Glu Ile Asp Gly Pro Ala Gly Gln Ala Glu Pro Asp Arg Ala
1               5                   10                  15

<210> SEQ ID NO 82
<211> LENGTH: 16

<212> TYPE: PRT
<213> ORGANISM: Artificial
<220> FEATURE:
<223> OTHER INFORMATION: peptide

<400> SEQUENCE: 82

Asp Lys Lys Gln Arg Phe His Asn Ile Arg Gly Arg Trp Thr Gly Arg
1               5                   10                  15

<210> SEQ ID NO 83
<211> LENGTH: 22
<212> TYPE: PRT
<213> ORGANISM: Artificial
<220> FEATURE:
<223> OTHER INFORMATION: peptide

<400> SEQUENCE: 83

Asp Pro Gln Glu Arg Pro Arg Lys Leu Pro Gln Leu Cys Thr Glu Leu
1               5                   10                  15

Gln Thr Thr Ile His Asp
            20

<210> SEQ ID NO 84
<211> LENGTH: 32
<212> TYPE: PRT
<213> ORGANISM: Artificial
<220> FEATURE:
<223> OTHER INFORMATION: peptide

<400> SEQUENCE: 84

Cys Val Tyr Cys Lys Gln Gln Leu Leu Arg Arg Glu Val Tyr Asp Phe
1               5                   10                  15

Ala Phe Arg Asp Leu Cys Ile Val Tyr Arg Asp Gly Asn Pro Tyr Ala
            20                  25                  30

<210> SEQ ID NO 85
<211> LENGTH: 10
<212> TYPE: PRT
<213> ORGANISM: Artificial
<220> FEATURE:
<223> OTHER INFORMATION: peptide

<400> SEQUENCE: 85

Phe Ala Phe Arg Asp Leu Cys Ile Val Tyr
1               5                   10

<210> SEQ ID NO 86
<211> LENGTH: 32
<212> TYPE: PRT
<213> ORGANISM: Artificial
<220> FEATURE:
<223> OTHER INFORMATION: peptide

<400> SEQUENCE: 86

Arg Asp Leu Cys Ile Val Tyr Arg Asp Gly Asn Pro Tyr Ala Val Cys
1               5                   10                  15

Asp Lys Cys Leu Lys Phe Tyr Ser Lys Ile Ser Glu Tyr Arg His Tyr
            20                  25                  30

<210> SEQ ID NO 87
<211> LENGTH: 22
<212> TYPE: PRT
<213> ORGANISM: Artificial
<220> FEATURE:
<223> OTHER INFORMATION: peptide

<400> SEQUENCE: 87

Tyr Arg Asp Gly Asn Pro Tyr Ala Val Cys Asp Lys Cys Leu Lys Phe
1               5                   10                  15

Tyr Ser Lys Ile Ser Glu
            20

<210> SEQ ID NO 88
<211> LENGTH: 33
<212> TYPE: PRT
<213> ORGANISM: Artificial
<220> FEATURE:
<223> OTHER INFORMATION: peptide

<400> SEQUENCE: 88

Cys Leu Lys Phe Tyr Ser Lys Ile Ser Glu Tyr Arg His Tyr Cys Tyr
1               5                   10                  15

Ser Leu Tyr Gly Thr Thr Leu Glu Gln Gln Tyr Asn Lys Pro Leu Cys
            20                  25                  30

Asp

<210> SEQ ID NO 89
<211> LENGTH: 22
<212> TYPE: PRT
<213> ORGANISM: Artificial
<220> FEATURE:
<223> OTHER INFORMATION: peptide

<400> SEQUENCE: 89

Tyr Gly Thr Thr Leu Glu Gln Gln Tyr Asn Lys Pro Leu Cys Asp Leu
1               5                   10                  15

Leu Ile Arg Cys Ile Asn
            20

<210> SEQ ID NO 90
<211> LENGTH: 22
<212> TYPE: PRT
<213> ORGANISM: Artificial
<220> FEATURE:
<223> OTHER INFORMATION: peptide

<400> SEQUENCE: 90

Lys Pro Leu Cys Asp Leu Leu Ile Arg Cys Ile Asn Cys Gln Lys Pro
1               5                   10                  15

Leu Cys Pro Glu Glu Lys
            20

<210> SEQ ID NO 91
<211> LENGTH: 22
<212> TYPE: PRT
<213> ORGANISM: Artificial
<220> FEATURE:
<223> OTHER INFORMATION: peptide

<400> SEQUENCE: 91

Glu Lys Gln Arg His Leu Asp Lys Lys Gln Arg Phe His Asn Ile Arg
1               5                   10                  15

Gly Arg Trp Thr Gly Arg
            20

<210> SEQ ID NO 92
<211> LENGTH: 10
<212> TYPE: PRT
<213> ORGANISM: Artificial

```
<220> FEATURE:
<223> OTHER INFORMATION: peptide

<400> SEQUENCE: 92

Lys Gln Arg Phe His Asn Ile Arg Gly Arg
1               5                   10

<210> SEQ ID NO 93
<211> LENGTH: 22
<212> TYPE: PRT
<213> ORGANISM: Artificial
<220> FEATURE:
<223> OTHER INFORMATION: peptide

<400> SEQUENCE: 93

Asp Leu Tyr Cys Tyr Glu Gln Leu Asn Asp Ser Ser Glu Glu Glu Asp
1               5                   10                  15

Glu Ile Asp Gly Pro Ala
            20

<210> SEQ ID NO 94
<211> LENGTH: 22
<212> TYPE: PRT
<213> ORGANISM: Artificial
<220> FEATURE:
<223> OTHER INFORMATION: peptide

<400> SEQUENCE: 94

His Tyr Asn Ile Val Thr Phe Cys Cys Lys Cys Asp Ser Thr Leu Arg
1               5                   10                  15

Leu Cys Val Gln Ser Thr
            20

<210> SEQ ID NO 95
<211> LENGTH: 11
<212> TYPE: PRT
<213> ORGANISM: Artificial
<220> FEATURE:
<223> OTHER INFORMATION: peptide

<400> SEQUENCE: 95

Ile Arg Thr Leu Glu Asp Leu Leu Met Gly Thr
1               5                   10

<210> SEQ ID NO 96
<211> LENGTH: 22
<212> TYPE: PRT
<213> ORGANISM: Artificial
<220> FEATURE:
<223> OTHER INFORMATION: peptide

<400> SEQUENCE: 96

Arg Glu His Gly Ile Gln Thr Leu Asn His Gln Val Val Pro Ala Tyr
1               5                   10                  15

Asn Ile Ser Lys Ser Lys
            20

<210> SEQ ID NO 97
<211> LENGTH: 22
<212> TYPE: PRT
<213> ORGANISM: Artificial
<220> FEATURE:
<223> OTHER INFORMATION: peptide

<400> SEQUENCE: 97
```

```
Asp Lys Cys Leu Lys Phe Tyr Ser Lys Ile Ser Glu Tyr Arg His Tyr
1               5                   10                  15

Cys Tyr Ser Leu Tyr Gly
            20
```

<210> SEQ ID NO 98
<211> LENGTH: 32
<212> TYPE: PRT
<213> ORGANISM: Artificial
<220> FEATURE:
<223> OTHER INFORMATION: peptide

<400> SEQUENCE: 98

```
Met His Gly Pro Lys Ala Thr Leu Gln Asp Ile Val Leu His Leu Glu
1               5                   10                  15

Pro Gln Asn Glu Ile Pro Val Asp Leu Leu Cys His Glu Gln Leu Ser
            20                  25                  30
```

<210> SEQ ID NO 99
<211> LENGTH: 16
<212> TYPE: PRT
<213> ORGANISM: Artificial
<220> FEATURE:
<223> OTHER INFORMATION: peptide

<400> SEQUENCE: 99

```
Ile Pro Val Asp Leu Leu Cys His Glu Gln Leu Ser Asp Ser Glu Glu
1               5                   10                  15
```

<210> SEQ ID NO 100
<211> LENGTH: 10
<212> TYPE: PRT
<213> ORGANISM: Artificial
<220> FEATURE:
<223> OTHER INFORMATION: peptide

<400> SEQUENCE: 100

```
Gln Glu Arg Pro Arg Lys Leu Pro Gln Leu
1               5                   10
```

<210> SEQ ID NO 101
<211> LENGTH: 10
<212> TYPE: PRT
<213> ORGANISM: Artificial
<220> FEATURE:
<223> OTHER INFORMATION: peptide

<400> SEQUENCE: 101

```
Thr Ile His Asp Ile Ile Leu Glu Cys Val
1               5                   10
```

<210> SEQ ID NO 102
<211> LENGTH: 10
<212> TYPE: PRT
<213> ORGANISM: Artificial
<220> FEATURE:
<223> OTHER INFORMATION: peptide

<400> SEQUENCE: 102

```
Gly Arg Trp Thr Gly Arg Cys Met Ser Cys
1               5                   10
```

<210> SEQ ID NO 103
<211> LENGTH: 10
<212> TYPE: PRT
<213> ORGANISM: Artificial

```
<220> FEATURE:
<223> OTHER INFORMATION: peptide

<400> SEQUENCE: 103

Ser Ser Arg Thr Arg Arg Glu Thr Gln Leu
1               5                   10

<210> SEQ ID NO 104
<211> LENGTH: 9
<212> TYPE: PRT
<213> ORGANISM: Artificial
<220> FEATURE:
<223> OTHER INFORMATION: peptide

<400> SEQUENCE: 104

Ile Val Leu His Leu Glu Pro Gln Asn
1               5

<210> SEQ ID NO 105
<211> LENGTH: 845
<212> TYPE: PRT
<213> ORGANISM: Hepatitis B virus

<400> SEQUENCE: 105

Met Pro Leu Ser Tyr Gln His Phe Arg Lys Leu Leu Leu Leu Asp Asp
1               5                   10                  15

Gly Thr Glu Ala Gly Pro Leu Glu Glu Glu Leu Pro Arg Leu Ala Asp
                20                  25                  30

Ala Asp Leu His Arg Arg Val Ala Glu Asp Leu Asn Leu Gly Asn Leu
            35                  40                  45

Asn Val Ser Ile Pro Trp Thr His Lys Val Gly Asn Phe Thr Gly Leu
    50                  55                  60

Tyr Ser Ser Thr Val Pro Ile Phe Asn Pro Glu Trp Gln Thr Pro Ser
65                  70                  75                  80

Phe Pro Lys Ile His Leu Gln Glu Asp Ile Ile Asn Arg Cys Gln Gln
                85                  90                  95

Phe Val Gly Pro Leu Thr Val Asn Glu Lys Arg Arg Leu Lys Leu Ile
            100                 105                 110

Met Pro Ala Arg Phe Tyr Pro Thr His Thr Lys Tyr Leu Pro Leu Asp
        115                 120                 125

Lys Gly Ile Lys Pro Tyr Tyr Pro Asp Gln Val Val Asn His Tyr Phe
    130                 135                 140

Gln Thr Arg His Tyr Leu His Thr Leu Trp Lys Ala Gly Ile Leu Tyr
145                 150                 155                 160

Lys Arg Glu Thr Thr Arg Ser Ala Ser Phe Cys Gly Ser Pro Tyr Ser
                165                 170                 175

Trp Glu Gln Glu Leu Gln His Gly Arg Leu Val Ile Lys Thr Ser Gln
            180                 185                 190

Arg His Gly Asp Glu Ser Phe Cys Ser Gln Ser Ser Gly Ile Leu Ser
        195                 200                 205

Arg Ser Ser Val Gly Pro Cys Ile Arg Ser Gln Leu Lys Gln Ser Arg
    210                 215                 220

Leu Gly Leu Gln Pro Arg Gln Gly Arg Leu Ala Ser Ser Gln Pro Ser
225                 230                 235                 240

Arg Ser Gly Ser Ile Arg Ala Lys Ala His Pro Ser Thr Arg Arg Tyr
                245                 250                 255

Phe Gly Val Glu Pro Ser Gly Ser Gly His Ile Asp His Ser Val Asn
            260                 265                 270
```

```
Asn Ser Ser Ser Cys Leu His Gln Ser Ala Val Arg Lys Ala Ala Tyr
            275                 280                 285

Ser His Leu Ser Thr Ser Lys Arg Gln Ser Ser Gly His Ala Val
    290                 295                 300

Glu Phe His Cys Leu Pro Pro Asn Ser Ala Gly Ser Gln Ser Gln Gly
305                 310                 315                 320

Ser Val Ser Ser Cys Trp Trp Leu Gln Phe Arg Asn Ser Lys Pro Cys
                325                 330                 335

Ser Glu Tyr Cys Leu Ser His Leu Val Asn Leu Arg Glu Asp Trp Gly
            340                 345                 350

Pro Cys Asp Glu His Gly Glu His His Ile Arg Ile Pro Arg Thr Pro
                355                 360                 365

Ala Arg Val Thr Gly Gly Val Phe Leu Val Asp Lys Asn Pro His Asn
    370                 375                 380

Thr Ala Glu Ser Arg Leu Val Val Asp Phe Ser Gln Phe Ser Arg Gly
385                 390                 395                 400

Ile Ser Arg Val Ser Trp Pro Lys Phe Ala Val Pro Asn Leu Gln Ser
                405                 410                 415

Leu Thr Asn Leu Leu Ser Ser Asn Leu Ser Trp Leu Ser Leu Asp Val
            420                 425                 430

Ser Ala Ala Phe Tyr His Ile Pro Leu His Pro Ala Ala Met Pro His
        435                 440                 445

Leu Leu Ile Gly Ser Ser Gly Leu Ser Arg Tyr Val Ala Arg Leu Ser
    450                 455                 460

Ser Asn Ser Arg Ile Asn Asn Asn Gln Tyr Gly Thr Met Gln Asn Leu
465                 470                 475                 480

His Asp Ser Cys Ser Arg Gln Leu Tyr Val Ser Leu Met Leu Leu Tyr
                485                 490                 495

Lys Thr Tyr Gly Trp Lys Leu His Leu Tyr Ser His Pro Ile Val Leu
            500                 505                 510

Gly Phe Arg Lys Ile Pro Met Gly Val Gly Leu Ser Pro Phe Leu Leu
    515                 520                 525

Ala Gln Phe Thr Ser Ala Ile Cys Ser Val Val Arg Arg Ala Phe Pro
        530                 535                 540

His Cys Leu Ala Phe Ser Tyr Met Asp Asp Val Val Leu Gly Ala Lys
545                 550                 555                 560

Ser Val Gln His Arg Glu Ser Leu Tyr Thr Ala Val Thr Asn Phe Leu
                565                 570                 575

Leu Ser Leu Gly Ile His Leu Asn Pro Asn Lys Thr Lys Arg Trp Gly
            580                 585                 590

Tyr Ser Leu Asn Phe Met Gly Tyr Ile Ile Gly Ser Trp Gly Thr Leu
    595                 600                 605

Pro Gln Asp His Ile Val Gln Lys Ile Lys His Cys Phe Arg Lys Leu
610                 615                 620

Pro Val Asn Arg Pro Ile Asp Trp Lys Val Cys Gln Arg Ile Val Gly
625                 630                 635                 640

Leu Leu Gly Phe Ala Ala Pro Phe Thr Gln Cys Gly Tyr Pro Ala Leu
                645                 650                 655

Met Pro Leu Tyr Ala Cys Ile Gln Ala Lys Gln Ala Phe Thr Phe Ser
            660                 665                 670

Pro Thr Tyr Lys Ala Phe Leu Ser Lys Gln Tyr Met Asn Leu Tyr Pro
    675                 680                 685
```

```
Val Ala Arg Gln Arg Pro Gly Leu Cys Gln Val Phe Ala Asp Ala Thr
    690                 695                 700
Pro Thr Gly Trp Gly Leu Ala Ile Gly His Gln Arg Met Arg Gly Thr
705                 710                 715                 720
Phe Val Ala Pro Leu Pro Ile His Thr Ala Glu Leu Leu Ala Ala Cys
                725                 730                 735
Phe Ala Arg Ser Arg Ser Gly Ala Lys Leu Ile Gly Thr Asp Asn Ser
            740                 745                 750
Val Val Leu Ser Arg Lys Tyr Thr Ser Phe Pro Trp Leu Leu Gly Cys
        755                 760                 765
Thr Ala Asn Trp Ile Leu Arg Gly Thr Ser Phe Val Tyr Val Pro Ser
    770                 775                 780
Ala Leu Asn Pro Ala Asp Asp Pro Ser Arg Gly Arg Leu Gly Leu Ser
785                 790                 795                 800
Arg Pro Leu Leu Arg Leu Pro Phe Gln Pro Thr Thr Gly Arg Thr Ser
                805                 810                 815
Leu Tyr Ala Val Ser Pro Ser Val Pro Ser His Leu Pro Val Arg Val
            820                 825                 830
His Phe Ala Ser Pro Leu His Val Ala Trp Arg Pro Pro
        835                 840                 845

<210> SEQ ID NO 106
<211> LENGTH: 214
<212> TYPE: PRT
<213> ORGANISM: Hepatitis B virus

<400> SEQUENCE: 106

Met Gln Leu Phe His Leu Cys Leu Ile Ile Ser Cys Thr Cys Pro Thr
1               5                   10                  15
Val Gln Ala Ser Lys Leu Cys Leu Gly Trp Leu Trp Gly Met Asp Ile
            20                  25                  30
Asp Pro Tyr Lys Glu Phe Gly Ala Thr Val Glu Leu Leu Ser Phe Leu
        35                  40                  45
Pro Ser Asp Phe Phe Pro Ser Val Arg Asp Leu Leu Asp Thr Ala Ser
    50                  55                  60
Ala Leu Tyr Arg Glu Ala Leu Glu Ser Pro Glu His Cys Ser Pro His
65                  70                  75                  80
His Thr Ala Leu Arg Gln Ala Ile Leu Cys Trp Gly Glu Leu Met Thr
                85                  90                  95
Leu Ala Thr Trp Val Gly Asn Asn Leu Glu Asp Pro Ala Ser Arg Asp
            100                 105                 110
Leu Val Val Asn Tyr Val Asn Thr Asn Val Gly Leu Lys Ile Arg Gln
        115                 120                 125
Leu Leu Trp Phe His Ile Ser Cys Leu Thr Phe Gly Arg Glu Thr Val
    130                 135                 140
Leu Glu Tyr Leu Val Ser Phe Gly Val Trp Ile Arg Thr Pro Pro Ala
145                 150                 155                 160
Tyr Arg Pro Pro Asn Ala Pro Ile Leu Ser Thr Leu Pro Glu Thr Thr
                165                 170                 175
Val Val Arg Arg Arg Asp Arg Gly Arg Ser Pro Arg Arg Arg Thr Pro
            180                 185                 190
Ser Pro Arg Arg Arg Arg Ser Pro Ser Pro Arg Arg Arg Arg Ser Gln
        195                 200                 205
Ser Arg Glu Ser Gln Cys
    210
```

<210> SEQ ID NO 107
<211> LENGTH: 154
<212> TYPE: PRT
<213> ORGANISM: Hepatitis B virus

<400> SEQUENCE: 107

Met Ala Ala Arg Leu Cys Cys Gln Leu Asp Pro Ala Arg Asp Val Leu
1               5                   10                  15

Cys Leu Arg Pro Val Gly Ala Glu Ser Arg Gly Arg Pro Leu Ser Gly
            20                  25                  30

Pro Leu Gly Ala Leu Pro Ser Pro Ser Pro Ser Ala Val Pro Ala Asp
        35                  40                  45

His Gly Ala His Leu Ser Leu Arg Gly Leu Pro Val Cys Ala Phe Ser
    50                  55                  60

Ser Ala Gly Pro Cys Ala Leu Arg Phe Thr Ser Ala Arg Arg Met Glu
65                  70                  75                  80

Thr Thr Val Asn Ala His Gln Ile Leu Pro Lys Val Leu His Lys Arg
                85                  90                  95

Thr Leu Gly Leu Ser Ala Met Ser Thr Thr Asp Leu Glu Ala Tyr Phe
            100                 105                 110

Lys Asp Cys Val Phe Lys Asp Trp Glu Glu Leu Gly Glu Glu Ile Arg
        115                 120                 125

Leu Lys Val Phe Val Leu Gly Cys Arg His Lys Leu Val Cys Ser
    130                 135                 140

Pro Ala Pro Cys Asn Phe Phe Thr Ser Ala
145                 150

<210> SEQ ID NO 108
<211> LENGTH: 400
<212> TYPE: PRT
<213> ORGANISM: Hepatitis B virus

<400> SEQUENCE: 108

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Val
        35                  40                  45

Lys Asp Asp Trp Pro Ala Ala Asn Gln Val Gly Val Gly Ala Phe Gly
    50                  55                  60

Pro Arg Leu Thr Pro Pro His Gly Gly Ile Leu Gly Trp Ser Pro Gln
65                  70                  75                  80

Ala Gln Gly Ile Leu Thr Thr Val Ser Thr Ile Pro Pro Pro Ala Ser
                85                  90                  95

Thr Asn Arg Gln Ser Gly Arg Gln Pro Thr Pro Ile Ser Pro Pro Leu
            100                 105                 110

Arg Asp Ser His Pro Gln Ala Met Gln Trp Asn Ser Thr Ala Phe His
        115                 120                 125

Gln Thr Leu Gln Asp Pro Arg Val Arg Gly Leu Tyr Leu Pro Ala Gly
    130                 135                 140

Gly Ser Ser Ser Gly Thr Val Asn Pro Ala Pro Asn Ile Ala Ser His
145                 150                 155                 160

Ile Ser Ser Ile Ser Ala Arg Thr Gly Asp Pro Val Thr Asn Met Glu
                165                 170                 175

Asn Ile Thr Ser Gly Phe Leu Gly Pro Leu Val Leu Gln Ala Gly
            180                 185                 190

Phe Phe Leu Leu Thr Arg Ile Leu Thr Ile Pro Gln Ser Leu Asp Ser
        195                 200                 205

Trp Trp Thr Ser Leu Asn Phe Leu Gly Ser Pro Val Cys Leu Gly
    210                 215                 220

Gln Asn Ser Gln Ser Pro Thr Ser Asn His Ser Pro Thr Ser Cys Pro
225                 230                 235                 240

Pro Ile Cys Pro Gly Tyr Arg Trp Met Cys Leu Arg Arg Phe Ile Ile
                245                 250                 255

Phe Leu Phe Ile Leu Leu Leu Cys Leu Ile Phe Leu Leu Val Leu Leu
                260                 265                 270

Asp Tyr Gln Gly Met Leu Pro Val Cys Pro Leu Ile Pro Gly Ser Thr
            275                 280                 285

Thr Thr Ser Thr Gly Pro Cys Lys Thr Cys Thr Thr Pro Ala Gln Gly
        290                 295                 300

Asn Ser Met Phe Pro Ser Cys Cys Cys Thr Lys Pro Thr Asp Gly Asn
305                 310                 315                 320

Cys Thr Cys Ile Pro Ile Pro Ser Ser Trp Ala Phe Ala Lys Tyr Leu
                325                 330                 335

Trp Glu Trp Ala Ser Val Arg Phe Ser Trp Leu Ser Leu Leu Val Pro
                340                 345                 350

Phe Val Gln Trp Phe Val Gly Leu Ser Pro Thr Val Trp Leu Ser Ala
            355                 360                 365

Ile Trp Met Met Trp Tyr Trp Gly Pro Ser Leu Tyr Ser Ile Val Ser
        370                 375                 380

Pro Phe Ile Pro Leu Leu Pro Ile Phe Phe Cys Leu Trp Val Tyr Ile
385                 390                 395                 400

<210> SEQ ID NO 109
<211> LENGTH: 30
<212> TYPE: PRT
<213> ORGANISM: Artificial
<220> FEATURE:
<223> OTHER INFORMATION: peptide

<400> SEQUENCE: 109

Met Pro Leu Ser Tyr Gln His Phe Arg Lys Leu Leu Leu Leu Asp Asp
1               5                   10                  15

Gly Thr Glu Ala Gly Pro Leu Glu Glu Glu Leu Pro Arg Leu
            20                  25                  30

<210> SEQ ID NO 110
<211> LENGTH: 35
<212> TYPE: PRT
<213> ORGANISM: Artificial
<220> FEATURE:
<223> OTHER INFORMATION: peptide

<400> SEQUENCE: 110

Ile Pro Trp Thr His Lys Val Gly Asn Phe Thr Gly Leu Tyr Ser Ser
1               5                   10                  15

Thr Val Pro Ile Phe Asn Pro Glu Trp Gln Thr Pro Ser Phe Pro Lys
            20                  25                  30

Ile His Leu
        35

```
<210> SEQ ID NO 111
<211> LENGTH: 33
<212> TYPE: PRT
<213> ORGANISM: Artificial
<220> FEATURE:
<223> OTHER INFORMATION: peptide

<400> SEQUENCE: 111

Val Asn Glu Lys Arg Arg Leu Lys Leu Ile Met Pro Ala Arg Phe Tyr
1               5                   10                  15

Pro Thr His Thr Lys Tyr Leu Pro Leu Asp Lys Gly Ile Lys Pro Tyr
            20                  25                  30

Tyr

<210> SEQ ID NO 112
<211> LENGTH: 33
<212> TYPE: PRT
<213> ORGANISM: Artificial
<220> FEATURE:
<223> OTHER INFORMATION: peptide

<400> SEQUENCE: 112

Tyr Pro Thr His Thr Lys Tyr Leu Pro Leu Asp Lys Gly Ile Lys Pro
1               5                   10                  15

Tyr Tyr Pro Asp Gln Val Val Asn His Tyr Phe Gln Thr Arg His Tyr
            20                  25                  30

Leu

<210> SEQ ID NO 113
<211> LENGTH: 39
<212> TYPE: PRT
<213> ORGANISM: Artificial
<220> FEATURE:
<223> OTHER INFORMATION: peptide

<400> SEQUENCE: 113

Val Val Asn His Tyr Phe Gln Thr Arg His Tyr Leu His Thr Leu Trp
1               5                   10                  15

Lys Ala Gly Ile Leu Tyr Lys Arg Glu Thr Thr Arg Ser Ala Ser Phe
            20                  25                  30

Cys Gly Ser Pro Tyr Ser Trp
        35

<210> SEQ ID NO 114
<211> LENGTH: 35
<212> TYPE: PRT
<213> ORGANISM: Artificial
<220> FEATURE:
<223> OTHER INFORMATION: peptide

<400> SEQUENCE: 114

Tyr Phe Gln Thr Arg His Tyr Leu His Thr Leu Trp Lys Ala Gly Ile
1               5                   10                  15

Leu Tyr Lys Arg Glu Thr Thr Arg Ser Ala Ser Phe Cys Gly Ser Pro
            20                  25                  30

Tyr Ser Trp
        35

<210> SEQ ID NO 115
<211> LENGTH: 34
<212> TYPE: PRT
<213> ORGANISM: Artificial
<220> FEATURE:
```

<223> OTHER INFORMATION: peptide

<400> SEQUENCE: 115

Asp Gln Val Val Asn His Tyr Phe Gln Thr Arg His Tyr Leu His Thr
1               5                   10                  15

Leu Trp Lys Ala Gly Ile Leu Tyr Lys Arg Glu Thr Thr Arg Ser Ala
            20                  25                  30

Ser Phe

<210> SEQ ID NO 116
<211> LENGTH: 32
<212> TYPE: PRT
<213> ORGANISM: Artificial
<220> FEATURE:
<223> OTHER INFORMATION: peptide

<400> SEQUENCE: 116

Ser Gln Ser Gln Gly Ser Val Ser Ser Cys Trp Trp Leu Gln Phe Arg
1               5                   10                  15

Asn Ser Lys Pro Cys Ser Glu Tyr Cys Leu Ser His Leu Val Asn Leu
            20                  25                  30

<210> SEQ ID NO 117
<211> LENGTH: 33
<212> TYPE: PRT
<213> ORGANISM: Artificial
<220> FEATURE:
<223> OTHER INFORMATION: peptide

<400> SEQUENCE: 117

Thr Ala Glu Ser Arg Leu Val Val Asp Phe Ser Gln Phe Ser Arg Gly
1               5                   10                  15

Ile Ser Arg Val Ser Trp Pro Lys Phe Ala Val Pro Asn Leu Gln Ser
            20                  25                  30

Leu

<210> SEQ ID NO 118
<211> LENGTH: 38
<212> TYPE: PRT
<213> ORGANISM: Artificial
<220> FEATURE:
<223> OTHER INFORMATION: peptide

<400> SEQUENCE: 118

Asn Leu Leu Ser Ser Asn Leu Ser Trp Leu Ser Leu Asp Val Ser Ala
1               5                   10                  15

Ala Phe Tyr His Ile Pro Leu His Pro Ala Ala Met Pro His Leu Leu
            20                  25                  30

Ile Gly Ser Ser Gly Leu
        35

<210> SEQ ID NO 119
<211> LENGTH: 38
<212> TYPE: PRT
<213> ORGANISM: Artificial
<220> FEATURE:
<223> OTHER INFORMATION: peptide

<400> SEQUENCE: 119

Ser Ser Asn Leu Ser Trp Leu Ser Leu Asp Val Ser Ala Ala Phe Tyr
1               5                   10                  15

His Ile Pro Leu His Pro Ala Ala Met Pro His Leu Leu Ile Gly Ser

```
                        20                  25                  30

Ser Gly Leu Ser Arg Tyr
        35

<210> SEQ ID NO 120
<211> LENGTH: 33
<212> TYPE: PRT
<213> ORGANISM: Artificial
<220> FEATURE:
<223> OTHER INFORMATION: peptide

<400> SEQUENCE: 120

Trp Leu Ser Leu Asp Val Ser Ala Ala Phe Tyr His Ile Pro Leu His
1               5                   10                  15

Pro Ala Ala Met Pro His Leu Leu Ile Gly Ser Ser Gly Leu Ser Arg
            20                  25                  30

Tyr

<210> SEQ ID NO 121
<211> LENGTH: 34
<212> TYPE: PRT
<213> ORGANISM: Artificial
<220> FEATURE:
<223> OTHER INFORMATION: peptide

<400> SEQUENCE: 121

His Asp Ser Cys Ser Arg Gln Leu Tyr Val Ser Leu Met Leu Leu Tyr
1               5                   10                  15

Lys Thr Tyr Gly Trp Lys Leu His Leu Tyr Ser His Pro Ile Val Leu
            20                  25                  30

Gly Phe

<210> SEQ ID NO 122
<211> LENGTH: 36
<212> TYPE: PRT
<213> ORGANISM: Artificial
<220> FEATURE:
<223> OTHER INFORMATION: peptide

<400> SEQUENCE: 122

Ser Pro Phe Leu Leu Ala Gln Phe Thr Ser Ala Ile Cys Ser Val Val
1               5                   10                  15

Arg Arg Ala Phe Pro His Cys Leu Ala Phe Ser Tyr Met Asp Asp Val
            20                  25                  30

Val Leu Gly Ala
        35

<210> SEQ ID NO 123
<211> LENGTH: 34
<212> TYPE: PRT
<213> ORGANISM: Artificial
<220> FEATURE:
<223> OTHER INFORMATION: peptide

<400> SEQUENCE: 123

Phe Leu Leu Ala Gln Phe Thr Ser Ala Ile Cys Ser Val Val Arg Arg
1               5                   10                  15

Ala Phe Pro His Cys Leu Ala Phe Ser Tyr Met Asp Asp Val Val Leu
            20                  25                  30

Gly Ala
```

```
<210> SEQ ID NO 124
<211> LENGTH: 34
<212> TYPE: PRT
<213> ORGANISM: Artificial
<220> FEATURE:
<223> OTHER INFORMATION: peptide

<400> SEQUENCE: 124

Arg Glu Ser Leu Tyr Thr Ala Val Thr Asn Phe Leu Leu Ser Leu Gly
1               5                   10                  15

Ile His Leu Asn Pro Asn Lys Thr Lys Arg Trp Gly Tyr Ser Leu Asn
            20                  25                  30

Phe Met

<210> SEQ ID NO 125
<211> LENGTH: 34
<212> TYPE: PRT
<213> ORGANISM: Artificial
<220> FEATURE:
<223> OTHER INFORMATION: peptide

<400> SEQUENCE: 125

Asn Pro Asn Lys Thr Lys Arg Trp Gly Tyr Ser Leu Asn Phe Met Gly
1               5                   10                  15

Tyr Ile Ile Gly Ser Trp Gly Thr Leu Pro Gln Asp His Ile Val Gln
            20                  25                  30

Lys Ile

<210> SEQ ID NO 126
<211> LENGTH: 39
<212> TYPE: PRT
<213> ORGANISM: Artificial
<220> FEATURE:
<223> OTHER INFORMATION: peptide

<400> SEQUENCE: 126

Tyr Pro Ala Leu Met Pro Leu Tyr Ala Cys Ile Gln Ala Lys Gln Ala
1               5                   10                  15

Phe Thr Phe Ser Pro Thr Tyr Lys Ala Phe Leu Ser Lys Gln Tyr Met
            20                  25                  30

Asn Leu Tyr Pro Val Ala Arg
            35

<210> SEQ ID NO 127
<211> LENGTH: 35
<212> TYPE: PRT
<213> ORGANISM: Artificial
<220> FEATURE:
<223> OTHER INFORMATION: peptide

<400> SEQUENCE: 127

Met Pro Leu Tyr Ala Cys Ile Gln Ala Lys Gln Ala Phe Thr Phe Ser
1               5                   10                  15

Pro Thr Tyr Lys Ala Phe Leu Ser Lys Gln Tyr Met Asn Leu Tyr Pro
            20                  25                  30

Val Ala Arg
        35

<210> SEQ ID NO 128
<211> LENGTH: 32
<212> TYPE: PRT
<213> ORGANISM: Artificial
<220> FEATURE:
```

<223> OTHER INFORMATION: peptide

<400> SEQUENCE: 128

Gln Arg Met Arg Gly Thr Phe Val Ala Pro Leu Pro Ile His Thr Ala
1               5                   10                  15

Glu Leu Leu Ala Ala Cys Phe Ala Arg Ser Arg Ser Gly Ala Lys Leu
            20                  25                  30

<210> SEQ ID NO 129
<211> LENGTH: 38
<212> TYPE: PRT
<213> ORGANISM: Artificial
<220> FEATURE:
<223> OTHER INFORMATION: peptide

<400> SEQUENCE: 129

Val Leu Ser Arg Lys Tyr Thr Ser Phe Pro Trp Leu Leu Gly Cys Thr
1               5                   10                  15

Ala Asn Trp Ile Leu Arg Gly Thr Ser Phe Val Tyr Val Pro Ser Ala
            20                  25                  30

Leu Asn Pro Ala Asp Asp
        35

<210> SEQ ID NO 130
<211> LENGTH: 36
<212> TYPE: PRT
<213> ORGANISM: Artificial
<220> FEATURE:
<223> OTHER INFORMATION: peptide

<400> SEQUENCE: 130

Arg Lys Tyr Thr Ser Phe Pro Trp Leu Leu Gly Cys Thr Ala Asn Trp
1               5                   10                  15

Ile Leu Arg Gly Thr Ser Phe Val Tyr Val Pro Ser Ala Leu Asn Pro
            20                  25                  30

Ala Asp Asp Pro
        35

<210> SEQ ID NO 131
<211> LENGTH: 36
<212> TYPE: PRT
<213> ORGANISM: Artificial
<220> FEATURE:
<223> OTHER INFORMATION: peptide

<400> SEQUENCE: 131

Val Leu Ser Arg Lys Tyr Thr Ser Phe Pro Trp Leu Leu Gly Cys Thr
1               5                   10                  15

Ala Asn Trp Ile Leu Arg Gly Thr Ser Phe Val Tyr Val Pro Ser Ala
            20                  25                  30

Leu Asn Pro Ala
        35

<210> SEQ ID NO 132
<211> LENGTH: 35
<212> TYPE: PRT
<213> ORGANISM: Artificial
<220> FEATURE:
<223> OTHER INFORMATION: peptide

<400> SEQUENCE: 132

Asp Pro Ala Ser Arg Asp Leu Val Val Asn Tyr Val Asn Thr Asn Val
1               5                   10                  15

-continued

Gly Leu Lys Ile Arg Gln Leu Leu Trp Phe His Ile Ser Cys Leu Thr
            20                  25                  30

Phe Gly Arg
        35

<210> SEQ ID NO 133
<211> LENGTH: 34
<212> TYPE: PRT
<213> ORGANISM: Artificial
<220> FEATURE:
<223> OTHER INFORMATION: peptide

<400> SEQUENCE: 133

Cys Leu Thr Phe Gly Arg Glu Thr Val Leu Glu Tyr Leu Val Ser Phe
1               5                   10                  15

Gly Val Trp Ile Arg Thr Pro Pro Ala Tyr Arg Pro Pro Asn Ala Pro
            20                  25                  30

Ile Leu

<210> SEQ ID NO 134
<211> LENGTH: 33
<212> TYPE: PRT
<213> ORGANISM: Artificial
<220> FEATURE:
<223> OTHER INFORMATION: peptide

<400> SEQUENCE: 134

Ala Leu Pro Ser Pro Ser Pro Ser Ala Val Pro Ala Asp His Gly Ala
1               5                   10                  15

His Leu Ser Leu Arg Gly Leu Pro Val Cys Ala Phe Ser Ser Ala Gly
            20                  25                  30

Pro

<210> SEQ ID NO 135
<211> LENGTH: 35
<212> TYPE: PRT
<213> ORGANISM: Artificial
<220> FEATURE:
<223> OTHER INFORMATION: peptide

<400> SEQUENCE: 135

Cys Ala Phe Ser Ser Ala Gly Pro Cys Ala Leu Arg Phe Thr Ser Ala
1               5                   10                  15

Arg Arg Met Glu Thr Thr Val Asn Ala His Gln Ile Leu Pro Lys Val
            20                  25                  30

Leu His Lys
        35

<210> SEQ ID NO 136
<211> LENGTH: 35
<212> TYPE: PRT
<213> ORGANISM: Artificial
<220> FEATURE:
<223> OTHER INFORMATION: peptide

<400> SEQUENCE: 136

His Gln Ile Leu Pro Lys Val Leu His Lys Arg Thr Leu Gly Leu Ser
1               5                   10                  15

Ala Met Ser Thr Thr Asp Leu Glu Ala Tyr Phe Lys Asp Cys Val Phe
            20                  25                  30

Lys Asp Trp

```
<210> SEQ ID NO 137
<211> LENGTH: 34
<212> TYPE: PRT
<213> ORGANISM: Artificial
<220> FEATURE:
<223> OTHER INFORMATION: peptide

<400> SEQUENCE: 137

Leu Glu Ala Tyr Phe Lys Asp Cys Val Phe Lys Asp Trp Glu Glu Leu
1               5                   10                  15

Gly Glu Glu Ile Arg Leu Lys Val Phe Val Leu Gly Gly Cys Arg His
            20                  25                  30

Lys Leu

<210> SEQ ID NO 138
<211> LENGTH: 36
<212> TYPE: PRT
<213> ORGANISM: Artificial
<220> FEATURE:
<223> OTHER INFORMATION: peptide

<400> SEQUENCE: 138

Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp
        35

<210> SEQ ID NO 139
<211> LENGTH: 36
<212> TYPE: PRT
<213> ORGANISM: Artificial
<220> FEATURE:
<223> OTHER INFORMATION: peptide

<400> SEQUENCE: 139

Cys Pro Pro Ile Cys Pro Gly Tyr Arg Trp Met Cys Leu Arg Arg Phe
1               5                   10                  15

Ile Ile Phe Leu Phe Ile Leu Leu Leu Cys Leu Ile Phe Leu Leu Val
            20                  25                  30

Leu Leu Asp Tyr
        35

<210> SEQ ID NO 140
<211> LENGTH: 36
<212> TYPE: PRT
<213> ORGANISM: Artificial
<220> FEATURE:
<223> OTHER INFORMATION: peptide

<400> SEQUENCE: 140

Cys Ile Pro Ile Pro Ser Ser Trp Ala Phe Ala Lys Tyr Leu Trp Glu
1               5                   10                  15

Trp Ala Ser Val Arg Phe Ser Trp Leu Ser Leu Leu Val Pro Phe Val
            20                  25                  30

Gln Trp Phe Val
        35

<210> SEQ ID NO 141
```

```
<211> LENGTH: 32
<212> TYPE: PRT
<213> ORGANISM: Artificial
<220> FEATURE:
<223> OTHER INFORMATION: peptide

<400> SEQUENCE: 141

Pro Ser Ser Trp Ala Phe Ala Lys Tyr Leu Trp Glu Trp Ala Ser Val
1               5                   10                  15

Arg Phe Ser Trp Leu Ser Leu Leu Val Pro Phe Val Gln Trp Phe Val
            20                  25                  30

<210> SEQ ID NO 142
<211> LENGTH: 31
<212> TYPE: PRT
<213> ORGANISM: Artificial
<220> FEATURE:
<223> OTHER INFORMATION: peptide

<400> SEQUENCE: 142

Ser Ser Trp Ala Phe Ala Lys Tyr Leu Trp Glu Trp Ala Ser Val Arg
1               5                   10                  15

Phe Ser Trp Leu Ser Leu Leu Val Pro Phe Val Gln Trp Phe Val
            20                  25                  30

<210> SEQ ID NO 143
<211> LENGTH: 36
<212> TYPE: PRT
<213> ORGANISM: Artificial
<220> FEATURE:
<223> OTHER INFORMATION: peptide

<400> SEQUENCE: 143

Trp Leu Ser Ala Ile Trp Met Met Trp Tyr Trp Gly Pro Ser Leu Tyr
1               5                   10                  15

Ser Ile Val Ser Pro Phe Ile Pro Leu Leu Pro Ile Phe Phe Cys Leu
            20                  25                  30

Trp Val Tyr Ile
            35

<210> SEQ ID NO 144
<211> LENGTH: 30
<212> TYPE: PRT
<213> ORGANISM: Artificial
<220> FEATURE:
<223> OTHER INFORMATION: peptide

<400> SEQUENCE: 144

Met Met Trp Tyr Trp Gly Pro Ser Leu Tyr Ser Ile Val Ser Pro Phe
1               5                   10                  15

Ile Pro Leu Leu Pro Ile Phe Phe Cys Leu Trp Val Tyr Ile
            20                  25                  30

<210> SEQ ID NO 145
<211> LENGTH: 31
<212> TYPE: PRT
<213> ORGANISM: Artificial
<220> FEATURE:
<223> OTHER INFORMATION: peptide

<400> SEQUENCE: 145

Trp Met Met Trp Tyr Trp Gly Pro Ser Leu Tyr Ser Ile Val Ser Pro
1               5                   10                  15

Phe Ile Pro Leu Leu Pro Ile Phe Phe Cys Leu Trp Val Tyr Ile
```

<210> SEQ ID NO 146
<211> LENGTH: 37
<212> TYPE: PRT
<213> ORGANISM: Artificial
<220> FEATURE:
<223> OTHER INFORMATION: peptide

<400> SEQUENCE: 146

Met Gln Leu Phe His Leu Cys Leu Ile Ile Ser Cys Thr Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu
        35

<210> SEQ ID NO 147
<211> LENGTH: 509
<212> TYPE: PRT
<213> ORGANISM: Homo sapiens

<400> SEQUENCE: 147

Met Glu Arg Arg Arg Leu Trp Gly Ser Ile Gln Ser Arg Tyr Ile Ser
1               5                   10                  15

Met Ser Val Trp Thr Ser Pro Arg Arg Leu Val Glu Leu Ala Gly Gln
            20                  25                  30

Ser Leu Leu Lys Asp Glu Ala Leu Ala Ile Ala Ala Leu Glu Leu Leu
        35                  40                  45

Pro Arg Glu Leu Phe Pro Pro Leu Phe Met Ala Ala Phe Asp Gly Arg
    50                  55                  60

His Ser Gln Thr Leu Lys Ala Met Val Gln Ala Trp Pro Phe Thr Cys
65                  70                  75                  80

Leu Pro Leu Gly Val Leu Met Lys Gly Gln His Leu His Leu Glu Thr
                85                  90                  95

Phe Lys Ala Val Leu Asp Gly Leu Asp Val Leu Leu Ala Gln Glu Val
            100                 105                 110

Arg Pro Arg Arg Trp Lys Leu Gln Val Leu Asp Leu Arg Lys Asn Ser
        115                 120                 125

His Gln Asp Phe Trp Thr Val Trp Ser Gly Asn Arg Ala Ser Leu Tyr
    130                 135                 140

Ser Phe Pro Glu Pro Glu Ala Ala Gln Pro Met Thr Lys Lys Arg Lys
145                 150                 155                 160

Val Asp Gly Leu Ser Thr Glu Ala Glu Gln Pro Phe Ile Pro Val Glu
                165                 170                 175

Val Leu Val Asp Leu Phe Leu Lys Glu Gly Ala Cys Asp Glu Leu Phe
            180                 185                 190

Ser Tyr Leu Ile Glu Lys Val Lys Arg Lys Lys Asn Val Leu Arg Leu
        195                 200                 205

Cys Cys Lys Lys Leu Lys Ile Phe Ala Met Pro Met Gln Asp Ile Lys
    210                 215                 220

Met Ile Leu Lys Met Val Gln Leu Asp Ser Ile Glu Asp Leu Glu Val
225                 230                 235                 240

Thr Cys Thr Trp Lys Leu Pro Thr Leu Ala Lys Phe Ser Pro Tyr Leu
                245                 250                 255

Gly Gln Met Ile Asn Leu Arg Arg Leu Leu Leu Ser His Ile His Ala
            260                 265                 270

```
Ser Tyr Ile Ser Pro Glu Lys Glu Gln Tyr Ile Ala Gln Phe
    275                 280                 285

Thr Ser Gln Phe Leu Ser Leu Gln Cys Leu Gln Ala Leu Tyr Val Asp
290                 295                 300

Ser Leu Phe Phe Leu Arg Gly Arg Leu Asp Gln Leu Leu Arg His Val
305                 310                 315                 320

Met Asn Pro Leu Glu Thr Leu Ser Ile Thr Asn Cys Arg Leu Ser Glu
                325                 330                 335

Gly Asp Val Met His Leu Ser Gln Ser Pro Ser Val Ser Gln Leu Ser
                340                 345                 350

Val Leu Ser Leu Ser Gly Val Met Leu Thr Asp Val Ser Pro Glu Pro
                355                 360                 365

Leu Gln Ala Leu Leu Glu Arg Ala Ser Ala Thr Leu Gln Asp Leu Val
                370                 375                 380

Phe Asp Glu Cys Gly Ile Thr Asp Asp Gln Leu Leu Ala Leu Leu Pro
385                 390                 395                 400

Ser Leu Ser His Cys Ser Gln Leu Thr Thr Leu Ser Phe Tyr Gly Asn
                405                 410                 415

Ser Ile Ser Ile Ser Ala Leu Gln Ser Leu Leu Gln His Leu Ile Gly
                420                 425                 430

Leu Ser Asn Leu Thr His Val Leu Tyr Pro Val Pro Leu Glu Ser Tyr
                435                 440                 445

Glu Asp Ile His Gly Thr Leu His Leu Glu Arg Leu Ala Tyr Leu His
                450                 455                 460

Ala Arg Leu Arg Glu Leu Leu Cys Glu Leu Gly Arg Pro Ser Met Val
465                 470                 475                 480

Trp Leu Ser Ala Asn Pro Cys Pro His Cys Gly Asp Arg Thr Phe Tyr
                485                 490                 495

Asp Pro Glu Pro Ile Leu Cys Pro Cys Phe Met Pro Asn
                500                 505

<210> SEQ ID NO 148
<211> LENGTH: 33
<212> TYPE: PRT
<213> ORGANISM: Artificial
<220> FEATURE:
<223> OTHER INFORMATION: peptide

<400> SEQUENCE: 148

Met Glu Arg Arg Arg Leu Trp Gly Ser Ile Gln Ser Arg Tyr Ile Ser
1               5                   10                  15

Met Ser Val Trp Thr Ser Pro Arg Arg Leu Val Glu Leu Ala Gly Gln
            20                  25                  30

Ser

<210> SEQ ID NO 149
<211> LENGTH: 35
<212> TYPE: PRT
<213> ORGANISM: Artificial
<220> FEATURE:
<223> OTHER INFORMATION: peptide

<400> SEQUENCE: 149

Val Trp Thr Ser Pro Arg Arg Leu Val Glu Leu Ala Gly Gln Ser Leu
1               5                   10                  15

Leu Lys Asp Glu Ala Leu Ala Ile Ala Ala Leu Glu Leu Leu Pro Arg
            20                  25                  30
```

Glu Leu Phe
        35

<210> SEQ ID NO 150
<211> LENGTH: 40
<212> TYPE: PRT
<213> ORGANISM: Artificial
<220> FEATURE:
<223> OTHER INFORMATION: peptide

<400> SEQUENCE: 150

Pro Glu Pro Thr Ile Asp Glu Leu Leu Pro Arg Glu Leu Phe Pro Pro
1               5                   10                  15

Leu Phe Met Ala Ala Phe Asp Gly Arg His Ser Gln Thr Leu Lys Ala
            20                  25                  30

Met Val Gln Ala Trp Pro Phe Thr
        35                  40

<210> SEQ ID NO 151
<211> LENGTH: 33
<212> TYPE: PRT
<213> ORGANISM: Artificial
<220> FEATURE:
<223> OTHER INFORMATION: peptide

<400> SEQUENCE: 151

Leu Lys Ala Met Val Gln Ala Trp Pro Phe Thr Cys Leu Pro Leu Gly
1               5                   10                  15

Val Leu Met Lys Gly Gln His Leu His Leu Glu Thr Phe Lys Ala Val
            20                  25                  30

Leu

<210> SEQ ID NO 152
<211> LENGTH: 35
<212> TYPE: PRT
<213> ORGANISM: Artificial
<220> FEATURE:
<223> OTHER INFORMATION: peptide

<400> SEQUENCE: 152

Cys Leu Pro Leu Gly Val Leu Met Lys Gly Gln His Leu His Leu Glu
1               5                   10                  15

Thr Phe Lys Ala Val Leu Asp Gly Leu Asp Val Leu Leu Ala Gln Glu
            20                  25                  30

Val Arg Pro
        35

<210> SEQ ID NO 153
<211> LENGTH: 33
<212> TYPE: PRT
<213> ORGANISM: Artificial
<220> FEATURE:
<223> OTHER INFORMATION: peptide

<400> SEQUENCE: 153

Leu Glu Thr Phe Lys Ala Val Leu Asp Gly Leu Asp Val Leu Leu Ala
1               5                   10                  15

Gln Glu Val Arg Pro Arg Arg Trp Lys Leu Gln Val Leu Asp Leu Arg
            20                  25                  30

Lys

```
<210> SEQ ID NO 154
<211> LENGTH: 33
<212> TYPE: PRT
<213> ORGANISM: Artificial
<220> FEATURE:
<223> OTHER INFORMATION: peptide

<400> SEQUENCE: 154

Val Arg Pro Arg Arg Trp Lys Leu Gln Val Leu Asp Leu Arg Lys Asn
1               5                   10                  15

Ser His Gln Asp Phe Trp Thr Val Trp Ser Gly Asn Arg Ala Ser Leu
            20                  25                  30

Tyr

<210> SEQ ID NO 155
<211> LENGTH: 34
<212> TYPE: PRT
<213> ORGANISM: Artificial
<220> FEATURE:
<223> OTHER INFORMATION: peptide

<400> SEQUENCE: 155

Trp Thr Val Trp Ser Gly Asn Arg Ala Ser Leu Tyr Ser Phe Pro Glu
1               5                   10                  15

Pro Glu Ala Ala Gln Pro Met Thr Lys Lys Arg Lys Val Asp Gly Leu
            20                  25                  30

Ser Thr

<210> SEQ ID NO 156
<211> LENGTH: 35
<212> TYPE: PRT
<213> ORGANISM: Artificial
<220> FEATURE:
<223> OTHER INFORMATION: peptide

<400> SEQUENCE: 156

Ile Pro Val Glu Val Leu Val Asp Leu Phe Leu Lys Glu Gly Ala Cys
1               5                   10                  15

Asp Glu Leu Phe Ser Tyr Leu Ile Glu Lys Val Lys Arg Lys Lys Asn
            20                  25                  30

Val Leu Arg
        35

<210> SEQ ID NO 157
<211> LENGTH: 34
<212> TYPE: PRT
<213> ORGANISM: Artificial
<220> FEATURE:
<223> OTHER INFORMATION: peptide

<400> SEQUENCE: 157

Glu Leu Phe Ser Tyr Leu Ile Glu Lys Val Lys Arg Lys Lys Asn Val
1               5                   10                  15

Leu Arg Leu Cys Cys Lys Lys Leu Lys Ile Phe Ala Met Pro Met Gln
            20                  25                  30

Asp Ile

<210> SEQ ID NO 158
<211> LENGTH: 35
<212> TYPE: PRT
<213> ORGANISM: Artificial
<220> FEATURE:
<223> OTHER INFORMATION: peptide
```

<400> SEQUENCE: 158

Ser Ile Glu Asp Leu Glu Val Thr Cys Thr Trp Lys Leu Pro Thr Leu
1               5                   10                  15

Ala Lys Phe Ser Pro Tyr Leu Gly Gln Met Ile Asn Leu Arg Arg Leu
            20                  25                  30

Leu Leu Ser
        35

<210> SEQ ID NO 159
<211> LENGTH: 33
<212> TYPE: PRT
<213> ORGANISM: Artificial
<220> FEATURE:
<223> OTHER INFORMATION: peptide

<400> SEQUENCE: 159

Pro Thr Leu Ala Lys Phe Ser Pro Tyr Leu Gly Gln Met Ile Asn Leu
1               5                   10                  15

Arg Arg Leu Leu Leu Ser His Ile His Ala Ser Ser Tyr Ile Ser Pro
            20                  25                  30

Glu

<210> SEQ ID NO 160
<211> LENGTH: 33
<212> TYPE: PRT
<213> ORGANISM: Artificial
<220> FEATURE:
<223> OTHER INFORMATION: peptide

<400> SEQUENCE: 160

Leu Arg Arg Leu Leu Leu Ser His Ile His Ala Ser Ser Tyr Ile Ser
1               5                   10                  15

Pro Glu Lys Glu Glu Gln Tyr Ile Ala Gln Phe Thr Ser Gln Phe Leu
            20                  25                  30

Ser

<210> SEQ ID NO 161
<211> LENGTH: 33
<212> TYPE: PRT
<213> ORGANISM: Artificial
<220> FEATURE:
<223> OTHER INFORMATION: peptide

<400> SEQUENCE: 161

Tyr Ile Ala Gln Phe Thr Ser Gln Phe Leu Ser Leu Gln Cys Leu Gln
1               5                   10                  15

Ala Leu Tyr Val Asp Ser Leu Phe Phe Leu Arg Gly Arg Leu Asp Gln
            20                  25                  30

Leu

<210> SEQ ID NO 162
<211> LENGTH: 33
<212> TYPE: PRT
<213> ORGANISM: Artificial
<220> FEATURE:
<223> OTHER INFORMATION: peptide

<400> SEQUENCE: 162

Leu Gln Cys Leu Gln Ala Leu Tyr Val Asp Ser Leu Phe Phe Leu Arg
1               5                   10                  15

```
Gly Arg Leu Asp Gln Leu Leu Arg His Val Met Asn Pro Leu Glu Thr
            20                  25                  30
Leu

<210> SEQ ID NO 163
<211> LENGTH: 35
<212> TYPE: PRT
<213> ORGANISM: Artificial
<220> FEATURE:
<223> OTHER INFORMATION: peptide

<400> SEQUENCE: 163

Val Leu Ser Leu Ser Gly Val Met Leu Thr Asp Val Ser Pro Glu Pro
1               5                   10                  15

Leu Gln Ala Leu Leu Glu Arg Ala Ser Ala Thr Leu Gln Asp Leu Val
            20                  25                  30

Phe Asp Glu
        35

<210> SEQ ID NO 164
<211> LENGTH: 33
<212> TYPE: PRT
<213> ORGANISM: Artificial
<220> FEATURE:
<223> OTHER INFORMATION: peptide

<400> SEQUENCE: 164

Leu Pro Ser Leu Ser His Cys Ser Gln Leu Thr Thr Leu Ser Phe Tyr
1               5                   10                  15

Gly Asn Ser Ile Ser Ile Ser Ala Leu Gln Ser Leu Leu Gln His Leu
            20                  25                  30

Ile

<210> SEQ ID NO 165
<211> LENGTH: 34
<212> TYPE: PRT
<213> ORGANISM: Artificial
<220> FEATURE:
<223> OTHER INFORMATION: peptide

<400> SEQUENCE: 165

Ser Ile Ser Ile Ser Ala Leu Gln Ser Leu Leu Gln His Leu Ile Gly
1               5                   10                  15

Leu Ser Asn Leu Thr His Val Leu Tyr Pro Val Pro Leu Glu Ser Tyr
            20                  25                  30

Glu Asp

<210> SEQ ID NO 166
<211> LENGTH: 34
<212> TYPE: PRT
<213> ORGANISM: Artificial
<220> FEATURE:
<223> OTHER INFORMATION: peptide

<400> SEQUENCE: 166

Ser Tyr Glu Asp Ile His Gly Thr Leu His Leu Glu Arg Leu Ala Tyr
1               5                   10                  15

Leu His Ala Arg Leu Arg Glu Leu Leu Cys Glu Leu Gly Arg Pro Ser
            20                  25                  30

Met Val
```

```
<210> SEQ ID NO 167
<211> LENGTH: 33
<212> TYPE: PRT
<213> ORGANISM: Artificial
<220> FEATURE:
<223> OTHER INFORMATION: peptide

<400> SEQUENCE: 167

Pro Ser Met Val Trp Leu Ser Ala Asn Pro Cys Pro His Cys Gly Asp
1               5                   10                  15

Arg Thr Phe Tyr Asp Pro Glu Pro Ile Leu Cys Pro Cys Phe Met Pro
            20                  25                  30

Asn

<210> SEQ ID NO 168
<211> LENGTH: 27
<212> TYPE: PRT
<213> ORGANISM: Artificial
<220> FEATURE:
<223> OTHER INFORMATION: peptide

<400> SEQUENCE: 168

Met Glu Arg Arg Arg Leu Trp Gly Ser Ile Gln Ser Arg Tyr Ile Ser
1               5                   10                  15

Met Ser Val Trp Thr Ser Pro Arg Arg Leu Val
            20                  25

<210> SEQ ID NO 169
<211> LENGTH: 27
<212> TYPE: PRT
<213> ORGANISM: Artificial
<220> FEATURE:
<223> OTHER INFORMATION: peptide

<400> SEQUENCE: 169

Val Trp Thr Ser Pro Arg Arg Leu Val Glu Leu Ala Gly Gln Ser Leu
1               5                   10                  15

Leu Lys Asp Glu Ala Leu Ala Ile Ala Ala Leu
            20                  25

<210> SEQ ID NO 170
<211> LENGTH: 22
<212> TYPE: PRT
<213> ORGANISM: Artificial
<220> FEATURE:
<223> OTHER INFORMATION: peptide

<400> SEQUENCE: 170

Leu Pro Arg Glu Leu Phe Pro Pro Leu Phe Met Ala Ala Phe Asp Gly
1               5                   10                  15

Arg His Ser Gln Thr Leu
            20

<210> SEQ ID NO 171
<211> LENGTH: 27
<212> TYPE: PRT
<213> ORGANISM: Artificial
<220> FEATURE:
<223> OTHER INFORMATION: peptide

<400> SEQUENCE: 171

Phe Pro Pro Leu Phe Met Ala Ala Phe Asp Gly Arg His Ser Gln Thr
1               5                   10                  15

Leu Lys Ala Met Val Gln Ala Trp Pro Phe Thr
```

```
                20                  25

<210> SEQ ID NO 172
<211> LENGTH: 26
<212> TYPE: PRT
<213> ORGANISM: Artificial
<220> FEATURE:
<223> OTHER INFORMATION: peptide

<400> SEQUENCE: 172

Lys Ala Met Val Gln Ala Trp Pro Phe Thr Cys Leu Pro Leu Gly Val
1               5                   10                  15

Leu Met Lys Gly Gln His Leu His Leu Glu
            20                  25

<210> SEQ ID NO 173
<211> LENGTH: 27
<212> TYPE: PRT
<213> ORGANISM: Artificial
<220> FEATURE:
<223> OTHER INFORMATION: peptide

<400> SEQUENCE: 173

Gly Val Leu Met Lys Gly Gln His Leu His Leu Glu Thr Phe Lys Ala
1               5                   10                  15

Val Leu Asp Gly Leu Asp Val Leu Leu Ala Gln
            20                  25

<210> SEQ ID NO 174
<211> LENGTH: 27
<212> TYPE: PRT
<213> ORGANISM: Artificial
<220> FEATURE:
<223> OTHER INFORMATION: peptide

<400> SEQUENCE: 174

Lys Ala Val Leu Asp Gly Leu Asp Val Leu Leu Ala Gln Glu Val Arg
1               5                   10                  15

Pro Arg Arg Trp Lys Leu Gln Val Leu Asp Leu
            20                  25

<210> SEQ ID NO 175
<211> LENGTH: 27
<212> TYPE: PRT
<213> ORGANISM: Artificial
<220> FEATURE:
<223> OTHER INFORMATION: peptide

<400> SEQUENCE: 175

Arg Trp Lys Leu Gln Val Leu Asp Leu Arg Lys Asn Ser His Gln Asp
1               5                   10                  15

Phe Trp Thr Val Trp Ser Gly Asn Arg Ala Ser
            20                  25

<210> SEQ ID NO 176
<211> LENGTH: 27
<212> TYPE: PRT
<213> ORGANISM: Artificial
<220> FEATURE:
<223> OTHER INFORMATION: peptide

<400> SEQUENCE: 176

Trp Thr Val Trp Ser Gly Asn Arg Ala Ser Leu Tyr Ser Phe Pro Glu
1               5                   10                  15
```

```
Pro Glu Ala Ala Gln Pro Met Thr Lys Lys Arg
            20                  25

<210> SEQ ID NO 177
<211> LENGTH: 27
<212> TYPE: PRT
<213> ORGANISM: Artificial
<220> FEATURE:
<223> OTHER INFORMATION: peptide

<400> SEQUENCE: 177

Leu Phe Leu Lys Glu Gly Ala Cys Asp Glu Leu Phe Ser Tyr Leu Ile
1               5                   10                  15

Glu Lys Val Lys Arg Lys Lys Asn Val Leu Arg
            20                  25

<210> SEQ ID NO 178
<211> LENGTH: 27
<212> TYPE: PRT
<213> ORGANISM: Artificial
<220> FEATURE:
<223> OTHER INFORMATION: peptide

<400> SEQUENCE: 178

Tyr Leu Ile Glu Lys Val Lys Arg Lys Lys Asn Val Leu Arg Leu Cys
1               5                   10                  15

Cys Lys Lys Leu Lys Ile Phe Ala Met Pro Met
            20                  25

<210> SEQ ID NO 179
<211> LENGTH: 22
<212> TYPE: PRT
<213> ORGANISM: Artificial
<220> FEATURE:
<223> OTHER INFORMATION: peptide

<400> SEQUENCE: 179

Ser Ile Glu Asp Leu Glu Val Thr Cys Thr Trp Lys Leu Pro Thr Leu
1               5                   10                  15

Ala Lys Phe Ser Pro Tyr
            20

<210> SEQ ID NO 180
<211> LENGTH: 27
<212> TYPE: PRT
<213> ORGANISM: Artificial
<220> FEATURE:
<223> OTHER INFORMATION: peptide

<400> SEQUENCE: 180

Pro Thr Leu Ala Lys Phe Ser Pro Tyr Leu Gly Gln Met Ile Asn Leu
1               5                   10                  15

Arg Arg Leu Leu Leu Ser His Ile His Ala Ser
            20                  25

<210> SEQ ID NO 181
<211> LENGTH: 22
<212> TYPE: PRT
<213> ORGANISM: Artificial
<220> FEATURE:
<223> OTHER INFORMATION: peptide

<400> SEQUENCE: 181

Leu Gly Gln Met Ile Asn Leu Arg Arg Leu Leu Leu Ser His Ile His
1               5                   10                  15
```

Ala Ser Ser Tyr Ile Ser
            20

<210> SEQ ID NO 182
<211> LENGTH: 27
<212> TYPE: PRT
<213> ORGANISM: Artificial
<220> FEATURE:
<223> OTHER INFORMATION: peptide

<400> SEQUENCE: 182

Leu Arg Arg Leu Leu Leu Ser His Ile His Ala Ser Ser Tyr Ile Ser
1               5                   10                  15

Pro Glu Lys Glu Glu Gln Tyr Ile Ala Gln Phe
            20                  25

<210> SEQ ID NO 183
<211> LENGTH: 27
<212> TYPE: PRT
<213> ORGANISM: Artificial
<220> FEATURE:
<223> OTHER INFORMATION: peptide

<400> SEQUENCE: 183

Ser Gln Phe Leu Ser Leu Gln Cys Leu Gln Ala Leu Tyr Val Asp Ser
1               5                   10                  15

Leu Phe Phe Leu Arg Gly Arg Leu Asp Gln Leu
            20                  25

<210> SEQ ID NO 184
<211> LENGTH: 27
<212> TYPE: PRT
<213> ORGANISM: Artificial
<220> FEATURE:
<223> OTHER INFORMATION: peptide

<400> SEQUENCE: 184

Ala Leu Tyr Val Asp Ser Leu Phe Phe Leu Arg Gly Arg Leu Asp Gln
1               5                   10                  15

Leu Leu Arg His Val Met Asn Pro Leu Glu Thr
            20                  25

<210> SEQ ID NO 185
<211> LENGTH: 27
<212> TYPE: PRT
<213> ORGANISM: Artificial
<220> FEATURE:
<223> OTHER INFORMATION: peptide

<400> SEQUENCE: 185

Val Leu Ser Leu Ser Gly Val Met Leu Thr Asp Val Ser Pro Glu Pro
1               5                   10                  15

Leu Gln Ala Leu Leu Glu Arg Ala Ser Ala Thr
            20                  25

<210> SEQ ID NO 186
<211> LENGTH: 27
<212> TYPE: PRT
<213> ORGANISM: Artificial
<220> FEATURE:
<223> OTHER INFORMATION: peptide

<400> SEQUENCE: 186

Leu Pro Ser Leu Ser His Cys Ser Gln Leu Thr Thr Leu Ser Phe Tyr

```
                1               5                   10                  15
Gly Asn Ser Ile Ser Ile Ser Ala Leu Gln Ser
                20                  25
```

<210> SEQ ID NO 187
<211> LENGTH: 27
<212> TYPE: PRT
<213> ORGANISM: Artificial
<220> FEATURE:
<223> OTHER INFORMATION: peptide

<400> SEQUENCE: 187

```
Gln Ser Leu Leu Gln His Leu Ile Gly Leu Ser Asn Leu Thr His Val
1               5                   10                  15

Leu Tyr Pro Val Pro Leu Glu Ser Tyr Glu Asp
                20                  25
```

<210> SEQ ID NO 188
<211> LENGTH: 27
<212> TYPE: PRT
<213> ORGANISM: Artificial
<220> FEATURE:
<223> OTHER INFORMATION: peptide

<400> SEQUENCE: 188

```
Ser Tyr Glu Asp Ile His Gly Thr Leu His Leu Glu Arg Leu Ala Tyr
1               5                   10                  15

Leu His Ala Arg Leu Arg Glu Leu Leu Cys Glu
                20                  25
```

<210> SEQ ID NO 189
<211> LENGTH: 27
<212> TYPE: PRT
<213> ORGANISM: Artificial
<220> FEATURE:
<223> OTHER INFORMATION: peptide

<400> SEQUENCE: 189

```
Ser Ala Asn Pro Cys Pro His Cys Gly Asp Arg Thr Phe Tyr Asp Pro
1               5                   10                  15

Glu Pro Ile Leu Cys Pro Cys Phe Met Pro Asn
                20                  25
```

<210> SEQ ID NO 190
<211> LENGTH: 393
<212> TYPE: PRT
<213> ORGANISM: Homo sapiens

<400> SEQUENCE: 190

```
Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
                20                  25                  30

Ser Pro Leu Pro Ser Gln Ala Met Asp Asp Leu Met Leu Ser Pro Asp
            35                  40                  45

Asp Ile Glu Gln Trp Phe Thr Glu Asp Pro Gly Pro Asp Glu Ala Pro
        50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95
```

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
            115                 120                 125

Ala Leu Asn Lys Met Phe Cys Gln Leu Ala Lys Thr Cys Pro Val Gln
            130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Arg Cys
            165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
            195                 200                 205

Arg Asn Thr Phe Arg His Ser Val Val Val Pro Tyr Glu Pro Pro Glu
            210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
            245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Asn
            275                 280                 285

Leu Arg Lys Lys Gly Glu Pro His His Glu Leu Pro Pro Gly Ser Thr
290                 295                 300

Lys Arg Ala Leu Pro Asn Asn Thr Ser Ser Pro Gln Pro Lys Lys
305                 310                 315                 320

Lys Pro Leu Asp Gly Glu Tyr Phe Thr Leu Gln Ile Arg Gly Arg Glu
            325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
            355                 360                 365

Leu Lys Ser Lys Lys Gly Gln Ser Thr Ser Arg His Lys Lys Leu Met
370                 375                 380

Phe Lys Thr Glu Gly Pro Asp Ser Asp
385                 390

<210> SEQ ID NO 191
<211> LENGTH: 30
<212> TYPE: PRT
<213> ORGANISM: Artificial
<220> FEATURE:
<223> OTHER INFORMATION: peptide

<400> SEQUENCE: 191

Ala Pro Ala Pro Ser Trp Pro Leu Ser Ser Val Pro Ser Gln Lys
1               5                   10                  15

Thr Tyr Gln Gly Ser Tyr Gly Phe Arg Leu Gly Phe Leu His
            20                  25                  30

<210> SEQ ID NO 192
<211> LENGTH: 30
<212> TYPE: PRT
<213> ORGANISM: Artificial
<220> FEATURE:

<223> OTHER INFORMATION: peptide

<400> SEQUENCE: 192

Thr Tyr Gln Gly Ser Tyr Gly Phe Arg Leu Gly Phe Leu His Ser Gly
1               5                   10                  15
Thr Ala Lys Ser Val Thr Cys Thr Tyr Ser Pro Ala Leu Asn
            20                  25                  30

<210> SEQ ID NO 193
<211> LENGTH: 30
<212> TYPE: PRT
<213> ORGANISM: Artificial
<220> FEATURE:
<223> OTHER INFORMATION: peptide

<400> SEQUENCE: 193

Pro Val Gln Leu Trp Val Asp Ser Thr Pro Pro Gly Thr Arg Val
1               5                   10                  15
Arg Ala Met Ala Ile Tyr Lys Gln Ser Gln His Met Thr Glu
            20                  25                  30

<210> SEQ ID NO 194
<211> LENGTH: 30
<212> TYPE: PRT
<213> ORGANISM: Artificial
<220> FEATURE:
<223> OTHER INFORMATION: peptide

<400> SEQUENCE: 194

Val Arg Ala Met Ala Ile Tyr Lys Gln Ser Gln His Met Thr Glu Val
1               5                   10                  15
Val Arg Arg Cys Pro His His Glu Arg Cys Ser Asp Ser Asp
            20                  25                  30

<210> SEQ ID NO 195
<211> LENGTH: 30
<212> TYPE: PRT
<213> ORGANISM: Artificial
<220> FEATURE:
<223> OTHER INFORMATION: peptide

<400> SEQUENCE: 195

Pro Pro Gln His Leu Ile Arg Val Glu Gly Asn Leu Arg Val Glu Tyr
1               5                   10                  15
Leu Asp Asp Arg Asn Thr Phe Arg His Ser Val Val Val Pro
            20                  25                  30

<210> SEQ ID NO 196
<211> LENGTH: 25
<212> TYPE: PRT
<213> ORGANISM: Artificial
<220> FEATURE:
<223> OTHER INFORMATION: peptide

<400> SEQUENCE: 196

Glu Val Gly Ser Asp Cys Thr Thr Ile His Tyr Asn Tyr Met Cys Asn
1               5                   10                  15
Ser Ser Cys Met Gly Gly Met Asn Arg
            20                  25

<210> SEQ ID NO 197
<211> LENGTH: 30
<212> TYPE: PRT
<213> ORGANISM: Artificial

<220> FEATURE:
<223> OTHER INFORMATION: peptide

<400> SEQUENCE: 197

Val Gly Ser Asp Cys Thr Thr Ile His Tyr Asn Tyr Met Cys Asn Ser
1               5                   10                  15

Ser Cys Met Gly Gly Met Asn Arg Arg Pro Ile Leu Thr Ile
            20                  25                  30

<210> SEQ ID NO 198
<211> LENGTH: 30
<212> TYPE: PRT
<213> ORGANISM: Artificial
<220> FEATURE:
<223> OTHER INFORMATION: peptide

<400> SEQUENCE: 198

Leu Glu Asp Ser Ser Gly Asn Leu Leu Gly Arg Asn Ser Phe Glu Val
1               5                   10                  15

Arg Val Cys Ala Cys Pro Gly Arg Asp Arg Arg Thr Glu Glu
            20                  25                  30

<210> SEQ ID NO 199
<211> LENGTH: 30
<212> TYPE: PRT
<213> ORGANISM: Artificial
<220> FEATURE:
<223> OTHER INFORMATION: peptide

<400> SEQUENCE: 199

Arg Val Cys Ala Cys Pro Gly Arg Asp Arg Arg Thr Glu Glu Glu Asn
1               5                   10                  15

Leu Arg Lys Lys Gly Glu Pro His His Glu Leu Pro Pro Gly
            20                  25                  30

<210> SEQ ID NO 200
<211> LENGTH: 30
<212> TYPE: PRT
<213> ORGANISM: Artificial
<220> FEATURE:
<223> OTHER INFORMATION: peptide

<400> SEQUENCE: 200

Leu Asp Asp Arg Asn Thr Phe Arg His Ser Val Val Val Pro Tyr Glu
1               5                   10                  15

Pro Pro Glu Val Gly Ser Asp Cys Thr Thr Ile His Tyr Asn
            20                  25                  30

<210> SEQ ID NO 201
<211> LENGTH: 30
<212> TYPE: PRT
<213> ORGANISM: Artificial
<220> FEATURE:
<223> OTHER INFORMATION: peptide

<400> SEQUENCE: 201

Arg Arg Cys Pro His His Glu Arg Cys Ser Asp Ser Asp Gly Leu Ala
1               5                   10                  15

Pro Pro Gln His Leu Ile Arg Val Glu Gly Asn Leu Arg Val
            20                  25                  30

<210> SEQ ID NO 202
<211> LENGTH: 30
<212> TYPE: PRT

```
<213> ORGANISM: Artificial
<220> FEATURE:
<223> OTHER INFORMATION: peptide

<400> SEQUENCE: 202

Ser Cys Met Gly Gly Met Asn Arg Arg Pro Ile Leu Thr Ile Ile Thr
1               5                   10                  15

Leu Glu Asp Ser Ser Gly Asn Leu Leu Gly Arg Asn Ser Phe
            20                  25                  30

<210> SEQ ID NO 203
<211> LENGTH: 30
<212> TYPE: PRT
<213> ORGANISM: Artificial
<220> FEATURE:
<223> OTHER INFORMATION: peptide

<400> SEQUENCE: 203

Tyr Ser Pro Ala Leu Asn Lys Met Phe Cys Gln Leu Ala Lys Thr Cys
1               5                   10                  15

Pro Val Gln Leu Trp Val Asp Ser Thr Pro Pro Pro Gly Thr
            20                  25                  30

<210> SEQ ID NO 204
<211> LENGTH: 30
<212> TYPE: PRT
<213> ORGANISM: Artificial
<220> FEATURE:
<223> OTHER INFORMATION: peptide

<400> SEQUENCE: 204

Ala Pro Pro Val Ala Pro Ala Pro Ala Ala Pro Thr Pro Ala Ala Pro
1               5                   10                  15

Ala Pro Ala Pro Ser Trp Pro Leu Ser Ser Ser Val Pro Ser
            20                  25                  30

<210> SEQ ID NO 205
<211> LENGTH: 30
<212> TYPE: PRT
<213> ORGANISM: Artificial
<220> FEATURE:
<223> OTHER INFORMATION: peptide

<400> SEQUENCE: 205

Ile Tyr Lys Gln Ser Gln His Met Thr Glu Val Val Arg Arg Cys Pro
1               5                   10                  15

His His Glu Arg Cys Ser Asp Ser Asp Gly Leu Ala Pro Pro
            20                  25                  30

<210> SEQ ID NO 206
<211> LENGTH: 30
<212> TYPE: PRT
<213> ORGANISM: Artificial
<220> FEATURE:
<223> OTHER INFORMATION: peptide

<400> SEQUENCE: 206

Lys Arg Ala Leu Pro Asn Asn Thr Ser Ser Ser Pro Gln Pro Lys Lys
1               5                   10                  15

Lys Pro Leu Asp Gly Glu Tyr Phe Thr Leu Gln Ile Arg Gly
            20                  25                  30

<210> SEQ ID NO 207
<211> LENGTH: 30
```

<212> TYPE: PRT
<213> ORGANISM: Artificial
<220> FEATURE:
<223> OTHER INFORMATION: peptide

<400> SEQUENCE: 207

Ala Gln Ala Gly Lys Glu Pro Gly Gly Ser Arg Ala His Ser His
1               5                   10                  15

Leu Lys Ser Lys Lys Gly Gln Ser Thr Ser Arg His Lys Lys
            20                  25                  30

<210> SEQ ID NO 208
<211> LENGTH: 25
<212> TYPE: PRT
<213> ORGANISM: Artificial
<220> FEATURE:
<223> OTHER INFORMATION: peptide

<400> SEQUENCE: 208

Leu Lys Ser Lys Lys Gly Gln Ser Thr Ser Arg His Lys Lys Leu Met
1               5                   10                  15

Phe Lys Thr Glu Gly Pro Asp Ser Asp
            20                  25

<210> SEQ ID NO 209
<211> LENGTH: 30
<212> TYPE: PRT
<213> ORGANISM: Artificial
<220> FEATURE:
<223> OTHER INFORMATION: peptide

<400> SEQUENCE: 209

Leu Arg Lys Lys Gly Glu Pro His His Glu Leu Pro Pro Gly Ser Thr
1               5                   10                  15

Lys Arg Ala Leu Pro Asn Asn Thr Ser Ser Ser Pro Gln Pro
            20                  25                  30

<210> SEQ ID NO 210
<211> LENGTH: 30
<212> TYPE: PRT
<213> ORGANISM: Artificial
<220> FEATURE:
<223> OTHER INFORMATION: peptide

<400> SEQUENCE: 210

Lys Pro Leu Asp Gly Glu Tyr Phe Thr Leu Gln Ile Arg Gly Arg Glu
1               5                   10                  15

Arg Phe Glu Met Phe Arg Glu Leu Asn Glu Ala Leu Glu Leu
            20                  25                  30

<210> SEQ ID NO 211
<211> LENGTH: 30
<212> TYPE: PRT
<213> ORGANISM: Artificial
<220> FEATURE:
<223> OTHER INFORMATION: peptide

<400> SEQUENCE: 211

Arg Phe Glu Met Phe Arg Glu Leu Asn Glu Ala Leu Glu Leu Lys Asp
1               5                   10                  15

Ala Gln Ala Gly Lys Glu Pro Gly Gly Ser Arg Ala His Ser
            20                  25                  30

<210> SEQ ID NO 212

```
<211> LENGTH: 720
<212> TYPE: PRT
<213> ORGANISM: Homo sapiens

<400> SEQUENCE: 212

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
        35                  40                  45

Ala Thr Asn Ile Thr Pro Lys His Asn Met Lys Ala Phe Leu Asp Glu
    50                  55                  60

Leu Lys Ala Glu Asn Ile Lys Lys Phe Leu Tyr Asn Phe Thr Gln Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
    130                 135                 140

Glu Pro Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
        195                 200                 205

Phe Arg Gly Asn Lys Val Lys Asn Ala Gln Leu Ala Gly Ala Lys Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Val Gln Arg Gly
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
        275                 280                 285

Leu Pro Ser Ile Pro Val His Pro Ile Gly Tyr Tyr Asp Ala Gln Lys
    290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
        355                 360                 365

Asp Arg Tyr Val Ile Leu Gly Gly His Arg Asp Ser Trp Val Phe Gly
    370                 375                 380

Gly Ile Asp Pro Gln Ser Gly Ala Ala Val Val His Glu Ile Val Arg
```

```
            385                 390                 395                 400
        Ser Phe Gly Thr Leu Lys Lys Glu Gly Trp Arg Pro Arg Arg Thr Ile
                        405                 410                 415

Leu Phe Ala Ser Trp Asp Ala Glu Phe Gly Leu Leu Gly Ser Thr
                        420                 425                 430

Glu Trp Ala Glu Glu Asn Ser Arg Leu Leu Gln Glu Arg Gly Val Ala
                        435                 440                 445

Tyr Ile Asn Ala Asp Ser Ser Ile Glu Gly Asn Tyr Thr Leu Arg Val
                450                 455                 460

Asp Cys Thr Pro Leu Met Tyr Ser Leu Val His Asn Leu Thr Lys Glu
        465                 470                 475                 480

Leu Lys Ser Pro Asp Glu Gly Phe Glu Gly Lys Ser Leu Tyr Glu Ser
                        485                 490                 495

Trp Thr Lys Lys Ser Pro Ser Pro Glu Phe Ser Gly Met Pro Arg Ile
                        500                 505                 510

Ser Lys Leu Gly Ser Gly Asn Asp Phe Glu Val Phe Phe Gln Arg Leu
                        515                 520                 525

Gly Ile Ala Ser Gly Arg Ala Arg Tyr Thr Lys Asn Trp Glu Thr Asn
                530                 535                 540

Lys Phe Ser Gly Tyr Pro Leu Tyr His Ser Val Tyr Glu Thr Tyr Glu
        545                 550                 555                 560

Leu Val Glu Lys Phe Tyr Asp Pro Met Phe Lys Tyr His Leu Thr Val
                        565                 570                 575

Ala Gln Val Arg Gly Gly Met Val Phe Glu Leu Ala Asn Ser Ile Val
                        580                 585                 590

Leu Pro Phe Asp Cys Arg Asp Tyr Ala Val Val Leu Arg Lys Tyr Ala
                        595                 600                 605

Asp Lys Ile Tyr Ser Ile Ser Met Lys His Pro Gln Glu Met Lys Thr
                610                 615                 620

Tyr Ser Val Ser Phe Asp Ser Leu Phe Ser Ala Val Lys Asn Phe Thr
        625                 630                 635                 640

Glu Ile Ala Ser Lys Phe Ser Glu Arg Leu Gln Asp Phe Asp Lys Ser
                        645                 650                 655

Asn Pro Ile Val Leu Arg Met Met Asn Asp Gln Leu Met Phe Leu Glu
                        660                 665                 670

Arg Ala Phe Ile Asp Pro Leu Gly Leu Pro Asp Arg Pro Phe Tyr Arg
                        675                 680                 685

His Val Ile Tyr Ala Pro Ser Ser His Asn Lys Tyr Ala Gly Glu Ser
                690                 695                 700

Phe Pro Gly Ile Tyr Asp Ala Leu Phe Asp Ile Glu Ser Lys Val Asp
        705                 710                 715                 720

<210> SEQ ID NO 213
<211> LENGTH: 33
<212> TYPE: PRT
<213> ORGANISM: Artificial
<220> FEATURE:
<223> OTHER INFORMATION: peptide

<400> SEQUENCE: 213

Asn Leu Leu His Glu Thr Asp Ser Ala Val Ala Thr Ala Arg Arg Pro
1               5                   10                  15

Arg Trp Leu Cys Ala Gly Ala Leu Val Leu Ala Gly Gly Phe Phe Leu
                20                  25                  30

Leu
```

<210> SEQ ID NO 214
<211> LENGTH: 35
<212> TYPE: PRT
<213> ORGANISM: Artificial
<220> FEATURE:
<223> OTHER INFORMATION: peptide

<400> SEQUENCE: 214

Gly Phe Phe Leu Leu Gly Phe Leu Phe Gly Trp Phe Ile Lys Ser Ser
1               5                   10                  15

Asn Glu Ala Thr Asn Ile Thr Pro Lys His Asn Met Lys Ala Phe Leu
            20                  25                  30

Asp Glu Leu
        35

<210> SEQ ID NO 215
<211> LENGTH: 36
<212> TYPE: PRT
<213> ORGANISM: Artificial
<220> FEATURE:
<223> OTHER INFORMATION: peptide

<400> SEQUENCE: 215

Thr Pro Lys His Asn Met Lys Ala Phe Leu Asp Glu Leu Lys Ala Glu
1               5                   10                  15

Asn Ile Lys Lys Phe Leu Tyr Asn Phe Thr Gln Ile Pro His Leu Ala
            20                  25                  30

Gly Thr Glu Gln
        35

<210> SEQ ID NO 216
<211> LENGTH: 37
<212> TYPE: PRT
<213> ORGANISM: Artificial
<220> FEATURE:
<223> OTHER INFORMATION: peptide

<400> SEQUENCE: 216

Lys Gln Ile Gln Ser Gln Trp Lys Glu Phe Gly Leu Asp Ser Val Glu
1               5                   10                  15

Leu Ala His Tyr Asp Val Leu Leu Ser Tyr Pro Asn Lys Thr His Pro
            20                  25                  30

Asn Tyr Ile Ser Ile
        35

<210> SEQ ID NO 217
<211> LENGTH: 33
<212> TYPE: PRT
<213> ORGANISM: Artificial
<220> FEATURE:
<223> OTHER INFORMATION: peptide

<400> SEQUENCE: 217

Asp Ile Val Pro Pro Phe Ser Ala Phe Ser Pro Gln Gly Met Pro Glu
1               5                   10                  15

Gly Asp Leu Val Tyr Val Asn Tyr Ala Arg Thr Glu Asp Phe Phe Lys
            20                  25                  30

Leu

<210> SEQ ID NO 218
<211> LENGTH: 36

```
<212> TYPE: PRT
<213> ORGANISM: Artificial
<220> FEATURE:
<223> OTHER INFORMATION: peptide

<400> SEQUENCE: 218

Lys Val Phe Arg Gly Asn Lys Val Lys Asn Ala Gln Leu Ala Gly Ala
1               5                   10                  15

Lys Gly Val Ile Leu Tyr Ser Asp Pro Ala Asp Tyr Phe Ala Pro Gly
            20                  25                  30

Val Lys Ser Tyr
        35

<210> SEQ ID NO 219
<211> LENGTH: 37
<212> TYPE: PRT
<213> ORGANISM: Artificial
<220> FEATURE:
<223> OTHER INFORMATION: peptide

<400> SEQUENCE: 219

Val Gln Arg Gly Asn Ile Leu Asn Leu Asn Gly Ala Gly Asp Pro Leu
1               5                   10                  15

Thr Pro Gly Tyr Pro Ala Asn Glu Tyr Ala Tyr Arg Arg Gly Ile Ala
            20                  25                  30

Glu Ala Val Gly Leu
        35

<210> SEQ ID NO 220
<211> LENGTH: 32
<212> TYPE: PRT
<213> ORGANISM: Artificial
<220> FEATURE:
<223> OTHER INFORMATION: peptide

<400> SEQUENCE: 220

Ala Gln Lys Leu Leu Glu Lys Met Gly Gly Ser Ala Pro Pro Asp Ser
1               5                   10                  15

Ser Trp Arg Gly Ser Leu Lys Val Pro Tyr Asn Val Gly Pro Gly Phe
            20                  25                  30

<210> SEQ ID NO 221
<211> LENGTH: 31
<212> TYPE: PRT
<213> ORGANISM: Artificial
<220> FEATURE:
<223> OTHER INFORMATION: peptide

<400> SEQUENCE: 221

Lys Val Lys Met His Ile His Ser Thr Asn Glu Val Thr Arg Ile Tyr
1               5                   10                  15

Asn Val Ile Gly Thr Leu Arg Gly Ala Val Glu Pro Asp Arg Tyr
            20                  25                  30

<210> SEQ ID NO 222
<211> LENGTH: 34
<212> TYPE: PRT
<213> ORGANISM: Artificial
<220> FEATURE:
<223> OTHER INFORMATION: peptide

<400> SEQUENCE: 222

Ala Val Val His Glu Ile Val Arg Ser Phe Gly Thr Leu Lys Lys Glu
1               5                   10                  15
```

Gly Trp Arg Pro Arg Arg Thr Ile Leu Phe Ala Ser Trp Asp Ala Glu
            20                  25                  30

Glu Phe

<210> SEQ ID NO 223
<211> LENGTH: 33
<212> TYPE: PRT
<213> ORGANISM: Artificial
<220> FEATURE:
<223> OTHER INFORMATION: peptide

<400> SEQUENCE: 223

Thr Glu Trp Ala Glu Glu Asn Ser Arg Leu Leu Gln Glu Arg Gly Val
1               5                   10                  15

Ala Tyr Ile Asn Ala Asp Ser Ser Ile Glu Gly Asn Tyr Thr Leu Arg
            20                  25                  30

Val

<210> SEQ ID NO 224
<211> LENGTH: 35
<212> TYPE: PRT
<213> ORGANISM: Artificial
<220> FEATURE:
<223> OTHER INFORMATION: peptide

<400> SEQUENCE: 224

Asn Ala Asp Ser Ser Ile Glu Gly Asn Tyr Thr Leu Arg Val Asp Cys
1               5                   10                  15

Thr Pro Leu Met Tyr Ser Leu Val His Asn Leu Thr Lys Glu Leu Lys
            20                  25                  30

Ser Pro Asp
        35

<210> SEQ ID NO 225
<211> LENGTH: 32
<212> TYPE: PRT
<213> ORGANISM: Artificial
<220> FEATURE:
<223> OTHER INFORMATION: peptide

<400> SEQUENCE: 225

Leu Met Tyr Ser Leu Val His Asn Leu Thr Lys Glu Leu Lys Ser Pro
1               5                   10                  15

Asp Glu Gly Phe Glu Gly Lys Ser Leu Tyr Glu Ser Trp Thr Lys Lys
            20                  25                  30

<210> SEQ ID NO 226
<211> LENGTH: 33
<212> TYPE: PRT
<213> ORGANISM: Artificial
<220> FEATURE:
<223> OTHER INFORMATION: peptide

<400> SEQUENCE: 226

Ser Gly Met Pro Arg Ile Ser Lys Leu Gly Ser Gly Asn Asp Phe Glu
1               5                   10                  15

Val Phe Phe Gln Arg Leu Gly Ile Ala Ser Gly Arg Ala Arg Tyr Thr
            20                  25                  30

Lys

<210> SEQ ID NO 227

```
<211> LENGTH: 33
<212> TYPE: PRT
<213> ORGANISM: Artificial
<220> FEATURE:
<223> OTHER INFORMATION: peptide

<400> SEQUENCE: 227

Ser Gly Tyr Pro Leu Tyr His Ser Val Tyr Glu Thr Tyr Glu Leu Val
1               5                   10                  15

Glu Lys Phe Tyr Asp Pro Met Phe Lys Tyr His Leu Thr Val Ala Gln
            20                  25                  30

Val

<210> SEQ ID NO 228
<211> LENGTH: 36
<212> TYPE: PRT
<213> ORGANISM: Artificial
<220> FEATURE:
<223> OTHER INFORMATION: peptide

<400> SEQUENCE: 228

Phe Tyr Asp Pro Met Phe Lys Tyr His Leu Thr Val Ala Gln Val Arg
1               5                   10                  15

Gly Gly Met Val Phe Glu Leu Ala Asn Ser Ile Val Leu Pro Phe Asp
            20                  25                  30

Cys Arg Asp Tyr
        35

<210> SEQ ID NO 229
<211> LENGTH: 34
<212> TYPE: PRT
<213> ORGANISM: Artificial
<220> FEATURE:
<223> OTHER INFORMATION: peptide

<400> SEQUENCE: 229

Val Leu Arg Lys Tyr Ala Asp Lys Ile Tyr Ser Ile Ser Met Lys His
1               5                   10                  15

Pro Gln Glu Met Lys Thr Tyr Ser Val Ser Phe Asp Ser Leu Phe Ser
            20                  25                  30

Ala Val

<210> SEQ ID NO 230
<211> LENGTH: 34
<212> TYPE: PRT
<213> ORGANISM: Artificial
<220> FEATURE:
<223> OTHER INFORMATION: peptide

<400> SEQUENCE: 230

Glu Arg Leu Gln Asp Phe Asp Lys Ser Asn Pro Ile Val Leu Arg Met
1               5                   10                  15

Met Asn Asp Gln Leu Met Phe Leu Glu Arg Ala Phe Ile Asp Pro Leu
            20                  25                  30

Gly Leu

<210> SEQ ID NO 231
<211> LENGTH: 35
<212> TYPE: PRT
<213> ORGANISM: Artificial
<220> FEATURE:
<223> OTHER INFORMATION: peptide
```

```
<400> SEQUENCE: 231

Leu Gly Leu Pro Asp Arg Pro Phe Tyr Arg His Val Ile Tyr Ala Pro
1               5                   10                  15

Ser Ser His Asn Lys Tyr Ala Gly Glu Ser Phe Pro Gly Ile Tyr Asp
                20                  25                  30

Ala Leu Phe
        35

<210> SEQ ID NO 232
<211> LENGTH: 34
<212> TYPE: PRT
<213> ORGANISM: Artificial
<220> FEATURE:
<223> OTHER INFORMATION: peptide

<400> SEQUENCE: 232

Glu Ser Lys Val Asp Pro Ser Lys Ala Trp Gly Glu Val Lys Arg Gln
1               5                   10                  15

Ile Tyr Val Ala Ala Phe Thr Val Gln Ala Ala Ala Glu Thr Leu Ser
                20                  25                  30

Glu Val
```